United States Patent
Braun et al.

(10) Patent No.: US 10,385,395 B2
(45) Date of Patent: Aug. 20, 2019

(54) DIAGNOSTIC TOOLS FOR RESPONSE TO 6-THIOPURINE THERAPY

(71) Applicant: THE REGENTS OF THE UNIVERSITY OF CALIFORNIA, Oakland, CA (US)

(72) Inventors: Jonathan Braun, Tarzana, CA (US); Lin Lin, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 746 days.

(21) Appl. No.: 14/391,814

(22) PCT Filed: Apr. 11, 2013

(86) PCT No.: PCT/US2013/036241
§ 371 (c)(1),
(2) Date: Oct. 10, 2014

(87) PCT Pub. No.: WO2013/155346
PCT Pub. Date: Oct. 17, 2013

(65) Prior Publication Data
US 2015/0079116 A1    Mar. 19, 2015

Related U.S. Application Data

(60) Provisional application No. 61/622,797, filed on Apr. 11, 2012.

(51) Int. Cl.
C12Q 1/6883 (2018.01)
G01N 33/68 (2006.01)

(52) U.S. Cl.
CPC ....... C12Q 1/6883 (2013.01); G01N 33/6893 (2013.01); C12Q 2600/106 (2013.01); C12Q 2600/172 (2013.01); G01N 2800/065 (2013.01)

(58) Field of Classification Search
CPC ............ C12Q 1/6883; C12Q 2600/106; C12Q 2600/172
See application file for complete search history.

(56) References Cited

U.S. PATENT DOCUMENTS

| 3,691,016 A | 9/1972 | Patel |
| 3,773,919 A | 11/1973 | Boswell et al. |
| 3,969,287 A | 7/1976 | Jaworek et al. |
| 4,179,337 A | 12/1979 | Davis et al. |

(Continued)

FOREIGN PATENT DOCUMENTS

| EP | 2322557 | 5/2011 |
| WO | WO 1987/005330 | 9/1987 |

(Continued)

OTHER PUBLICATIONS

Houtchens, K.A. et al. Immunogenetics 59:525 (2007).*
(Continued)

Primary Examiner — Diana B Johannsen
(74) Attorney, Agent, or Firm — Morgan, Lewis & Bockius LLP; Jeffry S. Mann; Louis T. Nguyen

(57) ABSTRACT

NK cell licensing predisposes patients to chronic inflammatory disease. Methods and kits to diagnose and treat chronic inflammatory disease based on genetic haplotype and cytokine profile are described herein.

4 Claims, 29 Drawing Sheets

(56) References Cited

U.S. PATENT DOCUMENTS

| | | | |
|---|---|---|---|
| 4,195,128 | A | 3/1980 | Hildebrand et al. |
| 4,229,537 | A | 10/1980 | Hodgins et al. |
| 4,247,642 | A | 1/1981 | Hirohara et al. |
| 4,301,144 | A | 11/1981 | Iwashita et al. |
| 4,330,440 | A | 5/1982 | Ayers et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 5,530,101 | A | 6/1996 | Queen et al. |
| 5,585,089 | A | 12/1996 | Queen et al. |
| 5,693,761 | A | 12/1997 | Queen et al. |
| 5,693,762 | A | 12/1997 | Queen et al. |
| 5,821,337 | A | 10/1998 | Carter et al. |
| 5,859,205 | A | 1/1999 | Adair et al. |
| 6,054,297 | A | 4/2000 | Carter et al. |
| 6,086,875 | A | 7/2000 | Blumberg et al. |
| 6,147,060 | A | 11/2000 | Zasloff |
| 6,180,370 | B1 | 1/2001 | Queen et al. |
| 6,407,213 | B1 | 6/2002 | Carter et al. |
| 6,602,684 | B1 | 8/2003 | Umaña et al. |
| 6,737,056 | B1 | 5/2004 | Presta |
| 7,317,091 | B2 | 1/2008 | Lazar et al. |
| 7,401,284 | B2 | 7/2008 | Bollano et al. |
| 7,521,541 | B2 | 4/2009 | Eigenbrot et al. |
| 7,610,156 | B2 | 10/2009 | Desjarlais et al. |
| 7,657,380 | B2 | 2/2010 | Lazar et al. |
| 7,670,600 | B2 | 3/2010 | Dall'Acqua et al. |
| 8,084,582 | B2 | 12/2011 | Dahiyat et al. |
| 8,163,551 | B2 | 4/2012 | Alley et al. |
| 8,188,231 | B2 | 5/2012 | Lazar et al. |
| 8,318,906 | B2 | 11/2012 | Braun et al. |
| 8,367,805 | B2 | 2/2013 | Chamberlain et al. |
| 8,937,158 | B2 | 1/2015 | Lazar et al. |
| 2001/0035606 | A1 | 11/2001 | Schoen |
| 2003/0003097 | A1 | 1/2003 | Reff et al. |
| 2003/0157108 | A1 | 8/2003 | Presta |
| 2004/0013210 | A1 | 1/2004 | Bollano et al. |
| 2005/0054832 | A1 | 3/2005 | Lazar et al. |
| 2005/0114037 | A1 | 5/2005 | Desjarlais et al. |
| 2006/0008883 | A1 | 1/2006 | Lazar et al. |
| 2006/0024298 | A1 | 2/2006 | Lazar et al. |
| 2006/0121032 | A1 | 6/2006 | Dahiyat et al. |
| 2006/0198840 | A1 | 9/2006 | Dall'Acqua et al. |
| 2006/0235208 | A1 | 10/2006 | Lazar et al. |
| 2007/0148170 | A1 | 6/2007 | Desjarlais et al. |
| 2008/0154025 | A1 | 6/2008 | Lazar et al. |
| 2009/0123439 | A1 | 5/2009 | Yun et al. |
| 2009/0163699 | A1 | 6/2009 | Chamberlain et al. |
| 2009/0317869 | A1 | 12/2009 | Alley et al. |
| 2010/0272732 | A1 | 10/2010 | Braun et al. |
| 2014/0234308 | A1 | 8/2014 | Braun et al. |
| 2015/0079089 | A1 | 3/2015 | Wadehra et al. |
| 2015/0079116 | A1 | 3/2015 | Lin et al. |
| 2015/0329621 | A1 | 11/2015 | Wadehra et al. |

FOREIGN PATENT DOCUMENTS

| | | |
|---|---|---|
| WO | WO 1992/011018 | 7/1992 |
| WO | WO 2000/061739 | 10/2000 |
| WO | WO 2001/029246 | 4/2001 |
| WO | WO 2002/030954 | 4/2002 |
| WO | WO 2002/031140 | 4/2002 |
| WO | WO 2006/094014 | 9/2006 |
| WO | WO 2006/108763 | 10/2006 |
| WO | WO 2009/048980 | 4/2009 |
| WO | WO 2010/053363 | 5/2010 |
| WO | WO 2011/103599 | 8/2011 |
| WO | WO 2011/112953 | 9/2011 |
| WO | WO 2011/146985 | 12/2011 |
| WO | WO 2013/056248 | 4/2013 |
| WO | WO 2013/119693 | 8/2013 |
| WO | WO 2013/148263 | 10/2013 |
| WO | WO 2013/155346 | 10/2013 |

OTHER PUBLICATIONS

Cu et al., ARVO Annual Meeting Abstract, Expression of Epithelial Membrane Protein 2 (EMP2) in Stem Cells (2011).
Gu et al., Cancer Science, 102(3): 557-564 (2011).
Kamat et al., Clin. Cancer Res. 13(24): p. 7487-7495 (2007).
Morii and Ikeda, Markers for Tumor-Initiating Cells, Kenbikyo, vol. 46, No. 2, pp. 85-88 (2011).
Zagouri et al., Obstetrics and Gynecology International, vol. 2010, Article ID 749579, p. 1-11 (2010).
Database GenBank, CAA64393 Epithelial Membrane Protein (2008).
Abad et al., Invest Opthalmol Vis Sci (2008).
Abrami et al., J Biol Chem 276:30729-36 (2001).
Acosta-Rodriguez et al., Nat Immunol 8, 942 (2007).
Adamis et al., Arch. Opthalmol. 114:66-71 (1996).
Al-Ejeh et al., Carcinogenesis. 32(5):650-658 (2011).
Al-Hajj et al., PNAS, 100:3983-3988 (2003).
Al Saleh et al., Int J Oncol. 38(5):1197-1217 (2011).
Altschul et al., J. Mol. Biol. 215:403-410 (1990).
Anfossi et al., Immunity 25, 331 (2006).
Aplin et al., J. Biol. Chem. 274,31223-31228 (1999).
Aplin and Wriston, Jr., CRC Crit. Rev. Biochem., pp. 259-306 (1981).
Arnaoutova and Kleinman, Nat. Protocols 5, 628-635 (2010).
Assarsson et al., J Immunol 173, 174 (2004).
Baca et al., J. Biol. Chem. 272(16):10678-10684 (1997).
Barbas, III et al., Proc. Nat. Acad. Sci, USA 91:3809-3813 (1994).
Barnett et al., Biochem J 385,399-408, (2005).
Bashirova et al., Annu Rev Immunol 29, 295 (2011).
Bates et al., Clin Sci (London) 110, 575-585 (2006).
Berkman et al., J Clin Invest 91:153-159 (1993).
Biassoni et al., J. Cell. Mol. Med., 7(4):376-387 (2003).
Biddle et al., Cancer Research, 71:5317-26 (2011).
Borgström et al., Cancer Res. 56:4032-4039 (1996).
Bouma and Strober, Nat Rev Immunol 3, 521 (2003).
Brodin et al., J Immunol 188, 2218 (2012).
Brogan et al., J Clin Immunol 5, 204 (1985).
Brown et al., Human Pathol. 26:86-91 (1995).
Brown et al., Cancer Res. 53:4727-4735 (1993).
Carmeliet et al., Nature 380:435-439 (1996).
Carter et al., Proc Natl Acad Sci USA 89:4285-9 (1992).
Cébe-Suarez et al., Cellular and Molecular Life Sciences 63, 601-615 (2006).
Cerweknka and Lanier, Nat. Rev. Immunol. 1:41-49 (2001).
Chan et al., Arthritis Rheum 52, 3586 (2005).
Charafe-Jauffret et al., Cancer Research, 69:1302-13 (2009).
Cho and Gregersen, N Engl J Med 365, 1612 (2011).
Chu et al., Clin. Cancer Res., 14(14): pp. 4484-4490 (2008).
Claas et al., J Biol Chem 276:7974-84 (2001).
Colman, Research in Immunology, 145: pp. 33-36 (1994).
Conley et al., PNAS, 109(8):2784-2789 (2012).
Cotspas et al., PLoS Genet 7, el 002254 (2011).
Croker and Allan, Breast Cancer Research and Treatment, 133:75-87 (2012).
Dahlin et al., Am J Respir Cell Mol Biol. 31(3):309-316 (2004).
Davies et al., Biotechnol Bioeng 74:288-294 (2001).
De Pascalis et al., J. Immunol. 169:3076-3084 (2002).
Dick, J.E., "Breast cancer stem cells revealed," PNAS, 100:3547-9 (2003).
Du et al., Immunogenetics 59, 1 (2007).
Duskin et al, J. Biol. Chem. 257:3105 (1982).
Dvorak et al., Am J. Pathol. 146:1029-1039 (1995).
Dvorak et al., Journal of Clinical Oncology 20, 4368-4380, (2002).
Edge et al., Anal. Biochem. 118:131 (1981).
Elias, A.D., Am J Clin Oncol. 33(6):637-645 (2010).
Elliot and Yokoyama, Trends Immunol 32, 364 (2011).
Engleman and Small, Jr., Semin Oncol 30:80-94 (2003).
Etzioni et al., Nature, 3(4): pp. 243-252 (2003).
Farag et al., Expert Opin. Biol. Ther., 3(2):237-250 (2003).
Fauriat et al., Blood 115, 1166 (2010).
Fauriat et al., Blood 115, 2167 (2010).
Ferrara and Davis-Smyth, Endocrine Rev. 18:4-25 (1997).
Ferrara, J. Mol. Med. 77:527-543 (1999).

(56) References Cited

OTHER PUBLICATIONS

Ferrara et al., Nature 380:439-442 (1996).
Ferrara et al., Nature Med. 4:336-340 (1998).
Ferrara, Nat Rev Cancer 2, 795-803 (2002).
Ferrara et al., Nat Rev Drug Discov 3,391-400 (2004).
Folkman, Nature Medicine, 1(1): pp. 27-31 (1995).
Fort et al., J Immunol 161, 3256 (1998).
Foulkes and Smith, N Engl J Med. 363(20):1938-1948 (2010).
Fu et al., Clin Cancer Res. 16(15):3954-3963 (2010).
Fu et al., PLoS One 6, e 19945 (2011).
Galbiati et al., Cell 106:403-11 (2001).
Gerber et al., Nature Med. 5:623-628 (1999).
Gorman et al., Proc. Natl. Acad. Sci. USA 88:4181-4185 (1991).
Gossett et al., Int J Gynecol Cancer 14:145-51 (2004).
Gruenberg and Maxfield., Curr Opin Cell Biol 7: 552-63 (1995).
Guerrin et al., J. Cell Physiol. 164:385-394 (1995).
Guia et al., Sci Signal 4, ra21 (2011).
Habeeb et al., Cancer. 116(20):4718-4726 (2010).
Hakamori, FEBS Lett. 584(9):1901-1906 (2010).
Hanna et al., J Olin Invest 114, 1612 (2004).
Harborth et al., Antisense Nucleic Acid Drug Dev. 13(2):83-105 (2003).
Hasse et al., J Neurosci Res 69:227-32 (2002).
Hawkins et al., J. Mol. Biol. 226:889-896 (1992).
He et al., J. Immunol. 160: 1029-1035 (1998).
Hecht et al., J Clin Oncol 24:4783-91 (2006).
Helguera and Penichet, Methods Mol Med. 109:347-374 (2005).
Hochgräfe et al., Cancer Res. 70(22):9391-9401 (2010).
Hollenbach et al., Immunogenetics 61, 663 (2009).
Hollenbach et al.. Immunogenetics 64, 719 (2012).
Holliger et al., Proc. Natl. Acad. Sci. U.S.A. 90:6444-6448 (1993).
Hu et al., Am J Cancer Res, 2(3):340-356 (2012).
Hu et al., Cancer Res. 56:3055-3061 (1996).
Huston et al., Proc. Natl. Acad. Sci. U.S.A. 85:5879-5883 (1988).
Hyde and Benbrook, Am. J. Pharmcol. Toxicol. 1(4):83-86 (2006).
Inoue et al., Cancer Cell 1, 193-202 (2002).
Jackson et al., J. Immunol. 154(7):3310-9 (1995).
Jones et al., Nature 321:522-525 (1986).
Jones et al., Genes Immun 7, 576 (2006).
Kadenhe-Chiweshe et al., Molecular Cancer Research 6, 1-9 (2008).
Kao et al., PLoS One. 4(7):e6146 (2009).
Kelloff et al., Clin Cancer Res 12:3661-97 (2006).
Khvorova et al., Cell. 115(2):209-16 (2003).
Khakoo and Carrington, Immunol Rev 214, 186 (2006).
Kilarski et al., Nat Med 15,657-664, (2009).
Kim et al., Nature 362:841-844 (1993).
Kim et al., Proc Natl Acad Sci U S A 105, 3053 (2008).
Konecny et al., British Journal of Cancer, 98: pp. 1076-1084 (2008).
Kornberg, Head Neck 20:634-639 (1998).
Krauss et al., Protein Engineering 16(10):753-759 (2003).
Kreike et al., Breast Cancer Research, 9: R65 (2007).
Lanier, L., Annual review of immunology 23, 225 (2005).
Lapidot et al., Nature, 367:645-648 (1994).
Leite De Oliveira et al., Molecular Aspects of Medicine 32, 71-87 (2011).
Leitinger and Hogg, J Cell Sci 115:963-72 (2002).
Li et al., Journal of the National Cancer Institute, 100:672-9 (2008).
Liu and Wicha, Journal of Clinical Oncology 28:4006-12 (2010).
Lobo et al., Annual Review of Cell and Developmental Biology. 23:675-99 (2007).
Lopez et al., Invest. Ophthalmo. Vis. Sci. 37:855-868 (1996).
Lorentzen et al., Ann Neurol 65, 658 (2009).
Lu et al., Cancer Res 69, 6889-6898, (2009).
MacCallum et al., J. Mol. Biol., 262, pp. 732-745 (1996).
Mah et al., Cancer. Res. 67(21):10484-10490 (2007).
Mahimainathan et al., American Journal of Physiology—Renal Physiology 289, F72-F82, (2005).
Mancuso et al., The Journal of Clinical Investigation 116, 2610-2621 (2006).
Markman, Semin Oncol 33: S33-8 (2006).
Marks et al., Biotechnology 10:779-783 (1992).
Martin et al., J Immunol 169, 2818 (2002).
Martin-Fontecha et al., Nat Immunol 5, 1260 (2004).
Mattern et al., Brit. J. Cancer. 73:931-934 (1996).
McGeachy, Immunity 28, 445 (2008).
Melnyk et al., Cancer Res. 56:921-924 (1996).
Mehers et al., Diabetologia 54, 3062 (2011).
Mercer, Immunol. Ser., 53: pp. 39-54 (1990).
Merdzhanova et al., Oncogene 29,5392-5403 (2010).
Moesta and Parham, Front Immunol 3, 336 (2012).
Moffett et al., J Biol Chem 275:2191-8 (2000).
Moodie et al., Eur J Immunogenet 29, 287 (2002).
Morales et al., Invest Ophthalmol Vis Sci. 50(10):4949-4956 (2009).
Morales et al. Exp Eye Res.85(6):790-798 (2007).
Morrison et al., Ann N Y Acad Sci. 507:187-198 (1987).
Narni-Mancinelli et al., Science 335, 344 (2012).
Neurath et al., Nat Med 8, 567 (2002).
Öberg-Welsh et al., Mol. Cell. Endocrinol. 126:125-132 (1997).
Obermayr et al., BMC Cancer.10:666 (2010).
O'Connor et al., Protein Eng 11:321-8 (1998).
Osborne and Schiff, Annu Rev Med. 62:233-247 (2011).
Owens et al., Cancer Res., 55:2752-2755 (1995).
Oza et al., Journal of Clinical Oncology 26(26): pp. 4319-4325 (2008).
Paik et al., N Engl J Med. 358(13):1409-1411 (2008).
Pal et al., Breast Cancer Res Treat. 125(3):627-636 (2011).
Paul, Fundamental Immunology, 3rd Edition, pp. 292-295 (1993).
Park et al., Mol. Biol. Cell 4, 1317-1326 (1993).
Park et al., Mol Ther. 17:219-230 (2009).
Parham, P., Nat Rev Immunol 5, 201 (2005).
Pectasides et al., Gynecol Oncol., 109: pp. 250-254 (2008).
Presson et al., BMC Cancer. 11:230 (2011).
Presta et al., Cancer Res. 57(20):4593-9 (1997).
Pylayeva et al., J Clin Invest. 119(2):252-266 (2009).
Qin et al., Journal of Biol. Chem. 289(20):13974-13985 (2014).
Qu et al., Methods. 36(1):84-95 (2005).
Queen et al., Proc Natl Acad Sci, USA 86:10029-33 (1989).
Radaev and Sun, Annu. Rev. Biophys. Biomol. Struct., 32:93-114 (2003).
Rader et al., Proc. Natl. Acad. Sci. USA 95: 8910-8915 (1998).
Rakha et al., Cancer. 109(1):25-32 (2007).
Raue et al., Immunity 38, 131 (2013).
Reiter et al., Nature Biotech. 14:1239-1245 (1996).
Reynolds et al., Nat Biotechnol. 22(3):326-30 (2004).
Rich and Bao, Cell Stem Cell, 1:353-5 (2007).
Richer et al., Immunity 38, 140 (2013).
Riechmann et al., Nature 332:323-329 (1988).
Rivera and Gomez, Breast Cancer Res.12 Suppl 2:S2 (2010).
Robinson and Stringer, J Cell Sci 114,853-865 (2001).
Roguska et al., Proc. Natl. Acad. Sci. USA 91:969-973 (1994).
Roque et al., Biotechnol. Prog. 20:639-654 (2004).
Rosok et al., J. Biol. Chem. 271(37): 22611-22618 (1996).
Rudikoff et al., Proc. Natl. Acad. Sci. USA, 79(6): pp. 1979-1983 (1982).
Schaller et al., Proc. Natl. Acad. Sci. USA 89:5192-5196 (1992).
Schaller and Frisch, Cancer Biol Ther. 9(10):791-793 (2010).
Schier et al., Gene 169:147-155 (1995).
Schönberg et al., Blood, 117(1): 98-107 (2011).
Shastry et al., International Journal of Immunogenetics 35, 439 (2008).
Shen et al., Hum Pathol. 37(12):1583-1591 (2006).
Sherman, Mod Pathol 13:295-308 (2000).
Shi and Van Kaer, Nat Rev Immunol 6, 751 (2006).
Shields et al., J Biol Chem 277:26733-26740 (2002).
Shimazaki et al., Clin Cancer Res. 14(22):7367-7377 (2008).
Shimazaki et al., Microbes Infect. 9(8):1003-1010 (2007).
Shimazaki et al., FEMS Immunol Med Microbiol. 55(2):240-249 (2009).
Shinkawa et al., J Biol Chem 278:3466-3473 (2003).
Siemeister et al., Cancer Metastasis Rev. 17:241-248 (1998).
Sojar and Bahl, Arch. Biochem. Biophys. 259:52 (1987).
Sondell et al., J. Neurosci. 19:5731-5740 (1999).
Sorosky, Obstet Gynecol 111:436-47 (2008).

(56) References Cited

OTHER PUBLICATIONS

Subik et al., Breast Cancer (Auckl). 4:35-41 (2010).
Takahashi et al., International Journal of Oncology, 35: pp. 725-729 (2009).
Tan et al., J. Immunol. 169:1119-1125 (2002).
Tanei et al., Clinical Cancer Research, 15:4234-41 (2009).
Tang et al., Cancer Cell 6, 485-495 (2004).
Tavassoli, Ed., World Health Organization Classification of Tumors: Tumors of the Breast and Female Genital Tract, Lyon: IARC Press, p. 221-57 (2003).
Teml et al., Clin. Pharmacokinet, 46(3):187-208 (2007).
Thotakura and Bahl, Meth. Enzymol. 138:350 (1987).
Tomlinson and Holliger, Methods Enzymol. 326:461-479 (2000).
Trachtenberg, E.A., Ann Neurol 65, 626 (2009).
Travasso et al., PLoS One 6, e19989 (2011).
Tsurushita and Vasquez, Humanization of Monoclonal Antibodies, Molecular Biology of B Cells, 533-545, Elsevier Science (USA) (2004).
Ui-Tei et al., Nucleic Acids Res. 32(3):936-48 (2004).
Umaña et al., Nat Biotechnol 17:176-180 (1999).
Valiante et al., Immunity 7, 739 (1997).
Van Der Slik et al., Diabetes 52, 2639 (2003).
Van't Veer et al., Nature. 415(6871):530-536 (2002).
Verhoeyen et al., Science 239:1534-1536 (1988).
Vivanco and Sawyers, Nat Rev Cancer 2,489-501 (2002).
Vivier et al., Nat Immunol 9, 503 (2008).
Wadehra et al., Biotechniques 32, 242-247 (2002).
Wadehra et al., J. Bio. Chem., 277, 41094-41100 (2002).
Wadehra et al., Clin Immunol 107:129-136 (2003).
Wadehra et al., Exp Mol Pathol 74:106-12 (2003).
Wadehra et al., Mol Biol Cell 15:2073-2083 (2004).
Wadehra et al., Dev Biol 287:336-45 (2005).
Wadehra et al., Reprod Biol Endocrinol 6:15 (2008).
Wadehra et al., Dev.Biol. 292,430-441 (2006).
Wadehra et al., Cancer Research, 73(8), Supp. 1, Abstract No. 240 (2013).
Wadehra et al., Journal of Clinical Oncology, 31(5), Supp. 1, Abstract No. 3080 (2013).
Wang et al., Cancer Res 66, 7864-7869, (2006).
Wang and Mu, Bioinformatics 20:11 1818-1820 (2004).
Warren et al., J. Clin. Invest. 95:1789-1797 (1995).
Warren et al., British J. Haematology, 121:793-804 (2003).
Wei et al., Int J Cancer. 81(5):748-754 (1999).
Weigelt, et al., Nat Rev Cancer. 5(8):591-602 (2005).
Weiner et al., Lancet 342:1024-1025 (1993).
Wilson et al., Nat Immunol 8, 950 (2007).
Wilson et al., Hum Immunol 71, 293 (2010).
Wright et al., Anticancer Research, 27(5B): 3525-3528 (2007).
Wu et al., J. Mol. Biol. 294:151-162 (1999).
Xuan et al., Blood. 115(14):2864-2871 (2010).
Yamaji et al., J Immunol 188, 2524 (2012).
Yawata et al., J Exp Med 203, 633 (2006).
Yelton et al., J. Immunol. 155:1994-2004 (1995).
Yokoyama and Kim, Immunity 24, 249 (2006).
Yoon et al., BMC Cancer. 10:335 (2010).
Yoon et al., Hum Pathol. 41(12):1794-1801 (2010).
Yoon et al., Cancer Biomark. 5(4):215-224 (2009).
Yorishima et al., Hiroshima J. Med. Sci., 46(1): Abstract (1997).
Zagzag et al., Lab Invest 86, 1221-1232 (2006).
Zerefos et al., Proteomics 6, 4346-4355, (2006).
Zhi et al., Diabetes Metab Res Rev 27, 872 (2011).
Zingoni et al., J Immunol 173, 3716 (2004).

\* cited by examiner

Figure 15

A. Total MS Patients

| No. | C1C1 | C1C2 | C2C2 | Total |
|---|---|---|---|---|
| Bw6/6 | 12 | 9 | 2 | 23 |
| Bw4/6 | 1 | 18 | 2 | 21 |
| Bw4/4 | 0 | 2 | 4 | 6 |
| Total | 13 | 29 | 8 | 50 |

B. AA haplotype MS Patients

| No. | C1C1 | C1C2 | C2C2 | Total |
|---|---|---|---|---|
| Bw6/6 | 2 | 4 | 0 | 6 |
| Bw4/6 | 0 | 10 | 0 | 10 |
| Bw4/4 | 0 | 0 | 1 | 1 |
| Total | 2 | 14 | 1 | 17 |

A.

B.

A.

B.

DIAGNOSTIC TOOLS FOR RESPONSE TO 6-THIOPURINE THERAPY

CROSS REFERENCE TO RELATED APPLICATIONS

This application claims the benefit under 35 U.S.C. § 119(e) to U.S. Application No. 61/622,797 filed Apr. 11, 2012, the disclosure of which is incorporated by reference in its entirety.

STATEMENT AS TO GOVERNMENT SUPPORT

This invention was made with Government support under Grant No. DK046763, awarded by the National Institutes of Health. The Government has certain rights in the invention.

FIELD OF THE INVENTION

This invention relates to the discovery that KIR gene licensing, or education, induces a unique cytokine program in human natural killer cells that stimulates $CD4^+$ T cell activation and TH17 differentiation, providing a mechanistic basis for KIR association in Crohn's Disease and other chronic inflammatory conditions.

BACKGROUND

Chronic inflammatory disease is characterized by chronic, or persistent, inflammation. Chronic inflammatory disease encompasses a large number of diseases, many of which comprise a genetic component. Specifically, many chronic inflammatory diseases are caused by a subject's genetic predisposition for developing the disease. Furthermore, the predisposition for developing certain chronic inflammatory diseases is caused by interaction and/or expression of multiple genes.

Chronic inflammatory disease can develop as a result of a patient's exposure to harmful stimuli. For example, exposure to certain foods and environmental factors may trigger the development of chronic inflammatory disease. Chronic inflammatory disease can result in pain, fatigue, and digestive problems. Furthermore, the chronic nature of the inflammation may lead to tissue damage which can lead to a variety of additional problems. For example, chronic inflammation in the liver and digestive tract can lead to neurological changes such as fatigue and changes in personality. Chronic inflammation can also alter normal function of organs which can cause systemic disease and disorders in afflicted patients.

Examples of chronic inflammatory disease include celiac disease, vasculitis, lupus, chronic obstructive pulmonary disease (COPD), inflammatory bowel disease, atherosclerosis, arthritis, and psoriasis. Specifically, inflammatory bowel disease is a broad class of chronic inflammatory diseases. Examples of inflammatory bowel diseases are Crohn's disease, ulcerative colitis, collagenous colitis, lymphocytic colitis, ischaemic colitis, diversion colitis, Behcet's disease, indeterminate colitis. While many of these diseases have genetic components, the specific triggers and underlying biochemical causes for the onset of the diseases remain unknown. Furthermore, because the triggers and underlying biochemical causes of the diseases remain largely unknown, treatment regimes merely target reducing the symptoms without eliminating the disease or the chronic inflammation entirely.

Because the inflammation is not easily controlled, constant medication is often administered to lessen the symptoms and side effects of the inflammation. The medications often include antibiotics, aminosalicylates, corticosteroids, immune modifiers, and biologic therapies. However, the medication will often lead additional pain such as aching joints and headache, fatigue, digestive problems, fever, skin irritation and sensitivity, stomach pain and irritation, dizziness, increased blood pressure, fluid retention, cataracts, glaucoma, high blood sugar, increased risk of infection, osteoporosis, weak bones, suppressed adrenal gland hormone production, and increased risk of bruising and bleeding. Accordingly, even though the inflammation may lessen and worsen throughout the course of the chronic disease with the aid of medical therapies, it is often very difficult to treat and persists with most known treatment regimes.

Recently, genetic studies have begun to elucidate factors contributing to chronic inflammatory disorders. For example, mucosal innate lymphocyte subsets have emerged as an important new factor in multiple chronic inflammatory disorders, including Crohn's Disease (CD). Furthermore, a recent genetic study identified the killer cell immunoglobulin-like receptor (KIR) gene KIR2DL2/3 of natural killer (NK) cells in the context of its ligand human leukocyte antigen (HLA)-C1 as a risk factor for CD. However, the cellular mechanism of this genetic contribution is unknown. Accordingly, without knowing the cellular mechanism of the genetic contribution of the KIR genes, the ability to customize therapies to such chronic inflammatory diseases and predict the effectiveness of a therapy remains unknown. Furthermore, without customized therapies and predicted efficacy of the therapies is known, constant medication (e.g., antibiotics, aminosalicylates, corticosteroids, immune modifiers, and biologic therapies) remains a necessity and negative side effects of the medications will continue to be problematic for patients.

This invention describes the 'licensing' of natural killer (NK) cells by specific genetic combinations of KIR and HLA genes results in their functional reprogramming, and permits them to promote $CD4^+$ T cell activation and TH17 differentiation ex vivo. Multiplexed bulk and single cell analysis of cytokine profile established that genetically licensed NK cells had a distinct cytokine profile from unlicensed NK cells, including polarized production of interferon (IFN)-y, tumor necrosis factor (TNF)-α, chemokine (C—C motif) ligand (CCL)-5, and macrophage inflammatory protein (MIP)-1β. These functional attributes of licensed NK cells were genetically rather than disease-defined, as they were observed in genetically licensed cohorts of healthy subjects, CD patients, and multiple sclerosis (MS) patients. Licensed NK cytokines augmented $CD4^+$ T cell proliferation and interleukin (IL)-17A/IL-22 production. Antibody blocking indicated a primary role for IFN-y, TNF-α, and IL-6 in the augmented T cell proliferative response. Thus, NK licensing mediated by KIR2DL2/3 and HLA-C1 elicits a novel NK cytokine program that activates and induces pro-inflammatory $CD4^+$ T cells, thereby providing a biologic mechanism for KIR-associated susceptibility to CD and other chronic inflammatory diseases.

BRIEF SUMMARY OF THE INVENTION

Two classes of measurements can be used to identify the level of educated NK cells, and therefore can be used to identify patients who have sufficient licensed NK cells to respond to 6-thiopuring therapy (e.g., 6-thioguanine therapy). The first type of measurement is the genetic identification of patients responsive to 6-thioguanine and 6-thiopurine therapy.

The genetic definition of patients responsive to 6-thioguanine and 6-thiopurine agents is achieved by identifying patients genetically capable of forming educated NK cells. This is achieved by measuring the combined presence of KIR (Killer cell immunoglobulin-like receptor) genes that confer strong NK education, and the presence of HLA (human leukocyte antigen) genes that represent their cognate ligands.

Accordingly, in some embodiments a kit is provided that encompasses a first and a second solid support and a manual, wherein the first solid support encompasses capture probes selective for KIR2DL3, KIR2DL1, KIR2DL4, KIR3DL1, KIR3DL2, KIR3DL3, KIR2DS4, KIR2DP1, KIR3DP1, KIR2DL5, KIR3DL3, KIR2DS1, KIR2DS2, KIR2DS3, DIR2DS4, KIR2DS5, and KIR3DS1, while the second solid encompasses capture probes selective for HLA, encompassing HLA-C1, HLA-C2, HLA-Bw4 and HLA-Bw6 and the manual encompasses a manual with (a) a genetic table that allows the input of 21 KIR genes, HLA class I ligands, including HLA-C1, HLA-C2, HLA-Bw4, and HLA-Bw6; (b) an easy-to-follow instruction or algorithm for genetic table interpretation with respect to level of educated NK cells, and likelihood of responding to 6-thioguanine therapy.

In other embodiments the kit further provides a manual with instructions encompassing the following:
1) For AA haplotype individuals (present of KIR2DL3, KIR2DL1, KIR2DL4, KIR3DL1, KIR3DL2, KIR3DL3, KIR2DS4, KIR2DP1, KIR3DP1, and absent of KIR2DL5, KIR3DL3, KIR2DS1, KIR2DS2, KIR2DS3, DIR2DS4, KIR2DS5, KIR3DS1 in their genome): (a) the homozygosity of HLA-C1 in combination with the presence of Bw6 predicts high likelihood of 6-thiopurine responsiveness; (b) homozygosity of Bw4 predicts moderate level of responsiveness; (c) heterozygosity of HLA-C1/HLA-C2 or homozygosity of HLA-C2 predicts low likelihood of responsiveness.
2) For non-AA haplotype individuals (any possible combination of KIR genes other than AA haplotype): (a) in the presence of KIR2DL2, the homozygosity of HLA-C1 or the heterozygosity of HLA-C1/HLA-C2 predicts high likelihood of 6-thiopurine responsiveness; (b) in the presence of KIR2DL2, the homozygosity of HLA-C2/HLA-C2 predicts low likelihood of 6-thiopurine responsiveness; (c) in the absence of KIR2DL2, homozygosity of HLA-C1 predicts high likelihood of responsiveness; (d) in the absence of KIR2DL2, heterozygosity of HLA-C1/HLA-C2 or homozygosity of HLA-C2 predicts low likelihood of responsiveness.

In other embodiments a method is provided, the method encompassing providing a biological sample, obtaining nucleic acid from the sample and hybridizing synthetic nucleic acid probes to the sample, wherein the probes specifically hybridize with KIR2DL3, KIR2DL1, KIR2DL4, KIR3DL1, KIR3DL2, KIR3DL3, KIR2DS4, KIR2DP1, KIR3DP1, KIR2DL5, KIR3DL3, KIR2DS1, KIR2DS2, KIR2DS3, DIR2DS4, KIR2DS5, KIR3DS1, HLA-C1, HLA-C2, HLA-Bw4 and HLA-Bw6.

The flow cytometry definition of patients responsive to 6-thiopurine agents is achieved by identifying patients bearing educated NK cells and/or enumerating the level of educated NK cells, above a basal level. Educated NK cells are identified, for example, as CD3-CD56+ that are positive for intracellular TNF-alpha, IL-6, and IFN-gamma.

Accordingly, in some embodiments a kit encompassing antibodies, a detectable label and instructions are provided, wherein the antibodies specifically recognize the markers CD3, CD56, TNF-α, IL-6 and IFN-γ.

In other embodiments a method is provided, wherein the method encompasses providing a biological sample and contacting said biological sample with antibodies that specifically recognize the markers CD3, CD56, TNF-α, IL-6 and IFN-γ.

In some embodiments the biological sample is a blood sample.

In a specific embodiment, this invention provides a method for determining the likelihood that a subject with chronic inflammatory disease will respond to therapy comprising. In certain embodiments, the method includes a step of providing a biological sample from a patient. In certain embodiments, the method includes a step of obtaining nucleic acid from the sample. In certain embodiments, the method includes a step of hybridizing a synthetic nucleic acid probe to the nucleic acid, wherein a first synthetic probe specifically binds to a member selected from the group consisting of KIR2DL3, KIR2DL1, KIR2DL4, KIR3DL1, KIR3DL2, KIR3DL3, KIR2DS4, KIR2DP1, KIR3DP1, KIR2DL5, KIR3DL3, KIR2DS1, KIR2DS2, KIR2DS3, DIR2DS4, KIR2DS5, KIR3DS1 and a second synthetic probe that specifically binds to a member selected from the group consisting of HLA-C1, HLA-C2, HLA-Bw4 and HLA-Bw6. In certain embodiments, the method includes a step of determining the KIR/HLA haplotype of the patient and thereby determining the likelihood the patient will respond to therapy. In certain embodiments, the method includes a step of administering a treatment regimen to the patients that are likely to respond to the therapy.

In certain embodiments, biological sample is a blood sample. In certain embodiments, patient is a human.

In certain embodiments, patient is a human. In certain embodiments, the homozygosity of HLA-C1 in combination with the presence of Bw6 predicts high likelihood of 6-thiopurine responsiveness. In certain embodiments, the homozygosity of Bw4 predicts moderate level of 6-thipurine responsiveness. In certain embodiments, the heterozygosity of HLA-C1/HLA-C2 or homozygosity of HLA-C2 predicts low likelihood of responsiveness.

In certain embodiments, the patient has a non-AA haplotype.

In certain embodiments, in the presence of KIR2DL2, the homozygosity of HLA-C1 or the heterozygosity of HLA-C1/HLA-C2 predicts high likelihood of 6-thiopurine responsiveness in a patient. In certain embodiments, in the presence of KIR2DL2, the homozygosity of HLA-C2/HLA-C2 predicts low likelihood of 6-thiopurine responsiveness. In certain embodiments, in the absence of KIR2DL2, homozygosity of HLA-C1 predicts high likelihood of responsiveness. In certain embodiments, in the absence of KIR2DL2, heterozygosity of HLA-C1/HLA-C2 or homozygosity of HLA-C2 predicts low likelihood of responsiveness.

In certain embodiments, the therapy comprises a 6-thiopurine or 6-thioguanine therapy. In certain embodiments, the treatment regimen comprises a 6-thiopurine or 6-thioguanine therapy. In certain embodiments, the treatment regimen comprises a 6-thiopurine or 6-thioguanine therapy. In certain embodiments, the treatment regimen does not comprise a 6-thiopurine or 6-thioguanine therapy.

In certain embodiments, the treatment regimen comprises antibiotic(s), anti-inflammatory(ies), anti-diarrheals, laxatives, pain relievers, iron supplements, aminosalicylate(s), steroids, corticosteroid(s), immune modifier(s), immunosupressor(s), anti-CD52 agents, biologic therapy(ies), vitamin B-12 shots, surgery, and nutritional plans. In certain embodiments, the anti-inflammatory(ies) is selected from a group comprising sufasalazine, mesalamine, NSAIDs, ImSAIDs, and corticosteroids. In certain embodiments, the immunosupressor(s) is selected from a group comprising zathioprine, mercaptopurine, infliximab, adalimumab, certolizumab pegol, methodtrexate, cyclosporine, natalizumab, cyclosporine, and tacrolimus. In certain embodiments, the antibiotic(s) is selected from a group comprising metronidazol and ciprofloxacin. In certain embodiments, the anti-CD52 agent is alemtuzumab.

In certain embodiments, the patient has predisposition for a chronic inflammatory disease.

In specific embodiments, the invention comprises a kit.

In certain embodiments, the kit comprises a first solid support comprising synthetic capture probes selective for KIR2DL3, KIR2DL1, KIR2DL4, KIR3DL1, KIR3DL2, KIR3DL3, KIR3DS4, KIR2DP1, KIR3DP1, KIR2DL5, KIR3DL3, KIR3DS1, KIR2DS2, KIR2DS3, DIR2DS4, KIR2DS5, and KIR3DS1. In certain embodiments, the kit comprises a second solid support comprising capture probes selective for HLA-C1, HLA-C2, HLA-Bw4 and HLA-Bw6. In certain embodiments, the kit comprises instructions.

In certain embodiments, the instructions are for AA haplotypes. In certain embodiments, the instructions for AA haplotypes comprise AA haplotype patients: (a) the homozygosity of HLA-C1 in combination with the presence of Bw6 predicts high likelihood of 6-thiopurine responsiveness; (b) homozygosity of Bw4 predicts moderate level of responsiveness; (c) heterozygosity of HLA-C1/HLA-C2 or homozygosity of HLA-C2 predicts low likelihood of responsiveness.

In certain embodiments, the instructions are for non-AA haplotypes. In certain embodiments, the instructions for non-AA haplotypes, wherein a non-AA haplotype is any possible combination of KIR genes other than AA haplotype: (a) in the presence of KIR2DL2, the homozygosity of HLA-C1 or the heterozygosity of HLA-C1/HLA-C2 predicts high likelihood of 6-thiopurine responsiveness; (b) in the presence of KIR2DL2, the homozygosity of HLA-C2/HLA-C2 predicts low likelihood of 6-thiopurine responsiveness; (c) in the absence of KIR2DL2, homozygosity of HLA-C1 predicts high likelihood of responsiveness; (d) in the absence of KIR2DL2, heterozygosity of HLA-C1/HLA-C2 or homozygosity of HLA-C2 predicts low likelihood of responsiveness.

In certain embodiments, the patient intended for the kit is a human.

In specific embodiments, this invention provides a method for determining the likelihood that a subject with chronic inflammatory disease will respond to therapy. In certain embodiments the method includes the step of providing a biological sample from a patient. In certain embodiments the method includes the step of contacting said biological sample from a patient with antibodies that specifically recognize the markers CD3, CD56, TNF-α, IL-6 and IFN-γ. In certain embodiments the method includes the step of determining the KIR/HLA haplotype of the patient and thereby determining the likelihood the patient will respond to therapy. In certain embodiments the method includes the step of administering a treatment regimen to the patients that are likely to respond to the therapy.

In certain embodiments, the haplotype of the patient is determined using an ELISA assay or Flow Cytometry.

In certain embodiments, the recognition of TNF-α, IL-6 and IFN-γ indicates the patient's likelihood of responding to therapy. In certain embodiments, the therapy is 6-thiopurine or 6-thioguanine therapy.

In certain embodiments, the treatment regime comprises a 6-thiopurine or 6-thioguanine therapy.

In certain embodiments, the treatment regimen comprises antibiotic(s), anti-inflammatory(ies), anti-diarrheals, laxatives, pain relievers, iron supplements, aminosalicylate(s), steroids, corticosteroid(s), immune modifier(s), immunosupressor(s), anti-CD52 agents, biologic therapy(ies), vitamin B-12 shots, surgery, and nutritional plans. In certain embodiments, the anti-inflammatory(ies) is selected from a group comprising sufasalazine, mesalamine, NSAIDs, ImSAIDs, and corticosteroids. In certain embodiments, the immunosupressor(s) is selected from a group comprising zathioprine, mercaptopurine, infliximab, adalimumab, certolizumab pegol, methodtrexate, cyclosporine, natalizumab, cyclosporine, and tacrolimus. In certain embodiments, the antibiotic(s) is selected from a group comprising metronidazol and ciprofloxacin. In certain embodiments, the anti-CD52 agent is alemtuzumab.

In specific embodiments, this invention provides a kit with antibodies, a detectable label, and instructions for treating and detecting chronic inflammatory disease. In certain embodiments, the antibodies specifically recognize the markers CD3, CD56, TNF-α, IL-6 and IFN-γ. In certain embodiments, the instructions comprise a table of ranges of licensed NK cells. In certain embodiments, the recognition of TNF-α, IL-6 and IFN-γ indicates the NK cell is a licensed NK cell.

These and other embodiments, features and potential advantages will become apparent with reference to the following description and drawings.

BRIEF DESCRIPTION OF THE DRAWINGS

FIG. 15 depicts a table of HLA allotype distribution in total and AA haplotype MS patients. (A) depicts the total MS patients and (B) depicts the AA haplotype MS patients. Values in each cell indicate the absolute number of patients.

DETAILED DESCRIPTION

Overview

Figure 1:
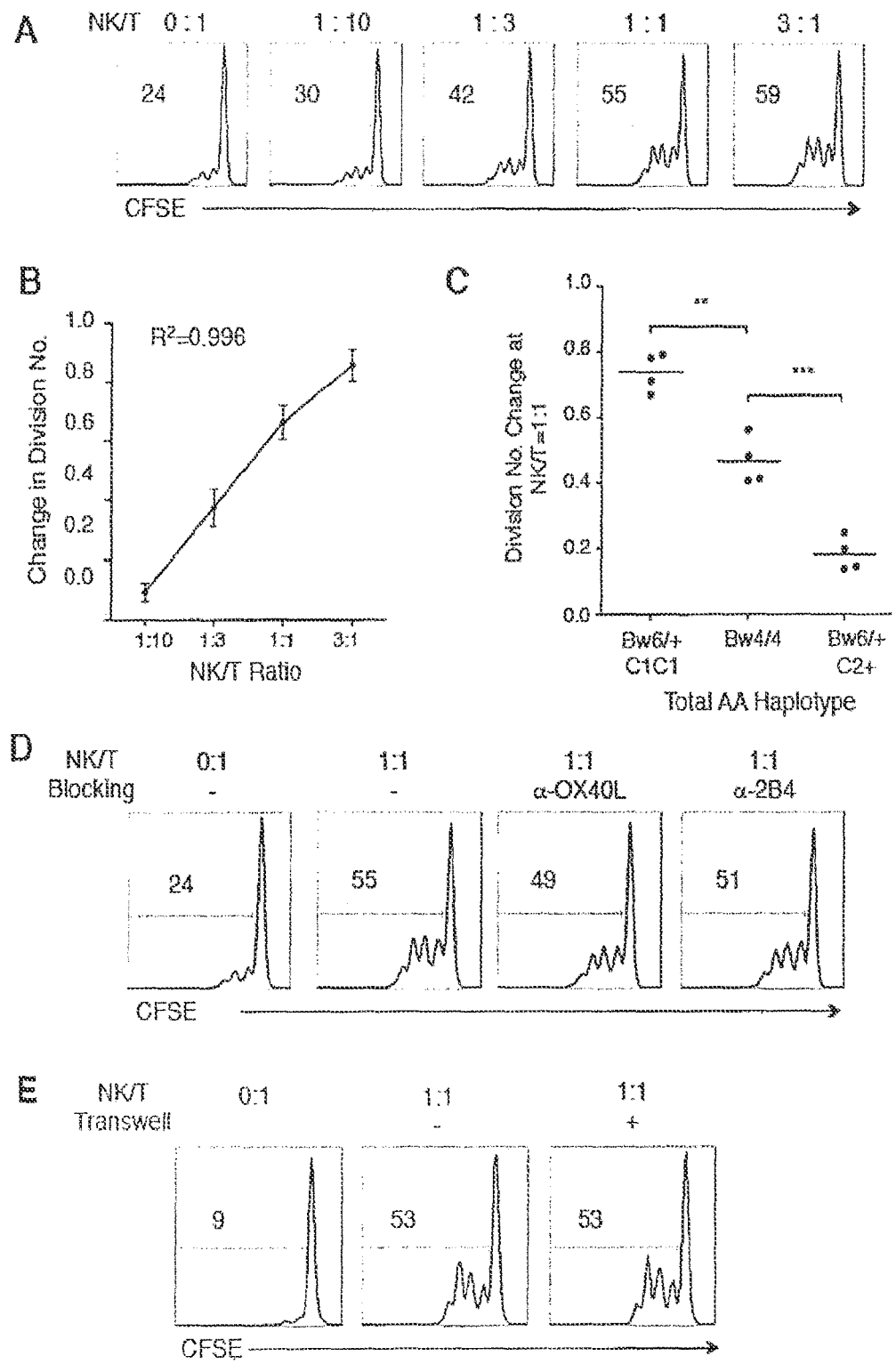
FIG. 1 depicts NK cells from genetically licensed CD patient strongly augment autologous CD4$^+$ T cell proliferation. NK cells and autologous T cells were isolated from AA haplotype CD patient peripheral blood, stimulated with 1.5 ug mL$^{-1}$ immobilized anti-CD3 anti-CD28, and co-cultured in 2 ng mL$^{-1}$ (26 I.U) IL-2 for three days. (A) Histograms of CD4$^+$ T cell CFSE dilution after co-culturing with NK cells at the NK/T ratios labeled above each plot, for a representative C1C1 CD patient. The number within each graph indicates the percentage of cells proliferated. (B) Correlation between NK/T ratio and change in CD4$^+$ T cell division number in log scale, calculated as mean CFSE intensity at co-culture/mean CFSE intensity of T cell alone. (C) Comparison of change in CD4$^+$ T cells division number at NK/T=1:1, among C1C1Bw6/+, Bw4/Bw4, and C2$^+$Bw6/$^+$ AA haplotype patients. (n=4, student t test, two-tailed. $p<0.005$; *$p<0.0005$). (D) Histograms of CD4$^+$ T cell CFSE dilution in the absence of (left two) or in the presence (right two) of the indicated blocking antibodies at 10 ug mL$^{-1}$. (E) Histograms of CD4$^+$ T cell CFSE dilution at the indicated NK/T ratio without physical separation of NK cells and T cells (left two) or with separation in 1.0 um pore size transwells (right one). The numbers in each histogram indicates the percentage of cells proliferated.

This invention is based on new findings, revealing that the immunologic function of NK cells differs depending on genetics that permits or prevents a functional state termed NK licensing (J. M. Elliott, W. M. Yokoyama, Unifying concepts of MHC-dependent natural killer cell education. Trends Immunol 32, 364 (August, 2011)). In individuals with select combination of gene alleles that permit licensing, NK cells acquire a number of functional properties that augment chronic inflammatory cellular immunity, and promote the chronic inflammatory disease state. Conversely, in individuals without such a genetic composition, their NK cells are in an unlicensed state, and do not promote the chronic inflammatory disease state. This discovery was demonstrated for patients with two disparate chronic inflammatory diseases (Crohn's disease and multiple sclerosis). Notably recent genetic work had revealed a relationship of these genes to various chronic inflammatory diseases (P. Parham, MHC class I molecules and KIRs in human history, health and survival. Nat Rev Immunol 5, 201 (March, 2005); J. A. Hollenbach et al., Susceptibility to Crohn's disease is mediated by KIR2DL2/KIR2DL3 heterozygosity and the HLA-C ligand. Immunogenetics 61, 663 (Sep. 30, 2009); E. A. Trachtenberg, Understanding the role of natural killer cell receptors and their human leukocyte antigen ligands in multiple sclerosis. Ann Neurol 65, 626 (June, 2009)), but the mechanism of this relationship was unknown, and hence these prior observations did not instruct how to apply these genetic findings to choice of therapy.

The present invention teaches that detection of licensed NK cells in patients may be detected by either by the presence of select combinations of genetic alleles, or by NK cytokine production characteristic of licensed NK cells. It also teaches that only chronic inflammatory disease patients with licensed NK cells are likely to benefit from therapies targeting NK cells. Such chronic inflammatory diseases include (but are not limited to) multiple sclerosis, Crohn's disease, ulcerative colitis, rheumatoid arthritis, organ transplant rejection, neuromyelitis optica, myasthenia gravis, psoriasis, systemic sclerosis, and Type 1 diabetes. NK targeting therapies include agents that selectively target NK cells (6-thioguanines, antibodies or other agents inhibiting IL-15 or IL15 receptor; blocking antibodies for KIRs, NKG2, or HLA), and other immune modulators that include targeting of NK cells (anti-CD52, such as alemtuzumab; steroids; cyclosporine; tacrolimus; glucocorticoids; and methotrexate).

There have been great strides in identifying genetic susceptibility loci for chronic inflammatory and autoimmune diseases, but a significant task remains to identify the functional consequences of these disease-associated variants (J. H. Cho, P. K. Gregersen, Genomics and the multifactorial nature of human autoimmune disease. *N Engl J Med* 365, 1612 (Oct. 27, 2011)). This task is framed by the functional networks emerging in disease-associated genes and the combinatorial features of these networks in the host phenotype (C. Cotsapas et al., Pervasive sharing of genetic effects in autoimmune disease. *PLoS Genet* 7, e1002254 (August, 2011)).

One important example is the genetic combination of killer immunoglobulin-like receptors (KIR) with their respective HLA class I ligands, that has been associated with multiple autoimmune disorders, infectious diseases, and cancers (A. A. Bashirova, R. Thomas, M. Carrington, HLA/KIR restraint of HIV: surviving the fittest. *Annu Rev Immunol* 29, 295 (2011); S. I. Khakoo, M. Carrington, KIR and disease: a model system or system of models? *Immunol Rev* 214, 186 (December, 2006)). However, the functional mechanisms accounting for these disease associations, particularly for the inhibitory class of KIRs, are poorly understood.

One challenge is that the KIR gene family cannot be systemically studied in model systems, as they are not present in the rodent genome. Another challenge is that the HLA and KIR gene families are functionally polymorphic, and each KIR has a selective affinity for specific alleles of individual class I HLA genes.

The KIR gene family is encoded in a 100-200 kb region of leukocyte receptor complex (LRC) on chromosome 19q13.4, comprised of 14 functional genes (seven activating, six inhibitory, one bi-functional) and 2 pseudogenes (Z. Du, D. W. Gjertson, E. F. Reed, R. Rajalingam, Receptor-ligand analyses define minimal killer cell Ig-like receptor (KIR) in humans. *Immunogenetics* 59, 1 (January, 2007)). The KIR locus exhibits haplotypes with extensive variations in number and types of KIR genes. Among the inhibitory KIRs, KIR2DL1 recognizes HLA-C2 allotypes, KIR2DL2 and KIR2DL3 recognize HLA-C1 allotypes, KIR3DL1 recognizes HLA-B allotypes with the serologically defined Bw4 motif; and some KIRs (2DL4 and 3DL3) lack known ligands (A. A. Bashirova, R. Thomas, M. Carrington, HLA/KIR restraint of HIV: surviving the fittest. *Annu Rev Immunol* 29, 295 (2011); Z. Du, D. W. Gjertson, E. F. Reed, R. Rajalingam, Receptor-ligand analyses define minimal killer cell Ig-like receptor (KIR) in humans. *Immunogenetics* 59, 1 (January, 2007)). Accordingly, the representation of individual HLA and KIR genes in an individual haplotype is quite heterogeneous for functional pairings of cognate HLA and KIR genes, which confounds studies of their biologic function.

KIR genes are predominantly expressed by NK cells, and are one element of a repertoire of cell surface receptors controlling NK cell activation, proliferation, and effector functions that mediate surveillance and host defense for microbial infection and malignancy (L. L. Lanier, NK cell recognition. *Annual review of immunology* 23, 225 (2005); C. Fauriat, M. A. Ivarsson, H. G. Ljunggren, K. J. Malmberg, J. Michaelsson, Education of human natural killer cells by activating killer cell immunoglobulin-like receptors. *Blood* 115, 1166 (Feb. 11, 2010)). The involvement of NK cells in various chronic inflammatory diseases has also been reported, but their roles are less well understood (A. A. Bashirova, R. Thomas, M. Carrington, HLA/KIR restraint of HIV: surviving the fittest. *Annu Rev Immunol* 29, 295 (2011); A. R. van der Slik et al., KIR in type 1 diabetes: disparate distribution of activating and inhibitory natural killer cell receptors in patients versus HLA-matched control subjects. *Diabetes* 52, 2639 (October, 2003); P. Parham, MHC class I molecules and KIRs in human history, health and survival. *Nat Rev Immunol* 5, 201 (March, 2005); E. A. Trachtenberg, Understanding the role of natural killer cell receptors and their human leukocyte antigen ligands in multiple sclerosis. *Ann Neurol* 65, 626 (June, 2009); A. R. Lorentzen et al., Killer immunoglobulin-like receptor ligand HLA-Bw4 protects against multiple sclerosis. *Ann Neurol* 65, 658 (June, 2009)). For example, there is evidence for NK cells either elevating or attenuating disease penetrance in different murine models of immune colitis (M. M. Fort, M. W. Leach, D. M. Rennick, A role for NK cells as regulators of CD4+ T cells in a transfer model of colitis. *J Immunol* 161, 3256 (1998); O. Yamaji et al., The development of colitogenic CD4(+) T cells is regulated by IL-7 in collaboration with NK cell function in a murine model of colitis. *J Immunol* 188, 2524 (Mar. 15, 2012)). Thus, the present study was prompted by the elevated genetic susceptibility for Crohn's disease in patients bearing the inhibitory KIR2DL2 and KIR2DL3 with its cognate ligand HLA-C1 (J. A. Hollenbach et al., Susceptibility to Crohn's disease is mediated by KIR2DL2/KIR2DL3 heterozygosity and the HLA-C ligand. *Immunogenetics* 61, 663 (Sep. 30, 2009); T. J. Wilson et al., Study of killer immunoglobulin-like receptor genes and human leukocyte antigens class I ligands in a Caucasian Brazilian population with Crohn's disease and ulcerative colitis. *Hum Immunol* 71, 293 (March, 2010); D. C. Jones et al., Killer Ig-like receptor (KIR) genotype and HLA ligand combinations in ulcerative colitis susceptibility. *Genes Immun* 7, 576 (October, 2006)).

The association of KIR2DL2/KIR2DL3 and HLA-C ligand is surprising, since NK-target interaction via inhibitory KIR ligation and self-MHC signals an immunoreceptor tyrosine-based inhibitory motif (ITIM)-mediated suppression of NK effector function that averts auto-aggressive tissue destruction (J. M. Elliott, W. M. Yokoyama, Unifying concepts of MHC-dependent natural killer cell education. *Trends Immunol* 32, 364 (August, 2011); W. M. Yokoyama, S. Kim, How do natural killer cells find self to achieve tolerance? *Immunity* 24, 249 (March, 2006)). One potential explanation of this association is that a decreased NK-dependent immune response to intestinal microbes may contribute to the microbial dysbiosis involved in Crohn's disease pathogenesis. However, thus far no such role for NK cells has been uncovered. A second explanation is the paradoxical function of inhibitory KIRs during NK differentiation: inhibitory KIR ligation induces NK cell licensing, a maturational process resulting in the acquisition of efficient target killing and IFN-γ-induction proficiencies (W. M. Yokoyama, S. Kim, How do natural killer cells find self to achieve tolerance? *Immunity* 24, 249 (March, 2006); N. Anfossi et al., Human NK cell education by inhibitory receptors for MHC class I. *Immunity* 25, 331 (August, 2006)). The influence of NK licensing on other aspects of NK cell function remains largely unknown, including its role in chronic inflammatory settings, its impact on adaptive immune response, and the scope of licensing-related cytokine and chemokine production (C. Fauriat, E. O. Long, H. G. Ljunggren, Y. T. Bryceson, Regulation of human NK-cell cytokine and chemokine production by target cell recognition. *Blood* 115, 2167 (Mar. 18, 2010)).

Therefore, this invention aims to elucidate the association between NK licensing and Crohn's disease susceptibility. As described herein, NK cells from genetically licensed healthy subjects and CD patients efficiently augment antigenic CD4+ T cell proliferation, and this augmentation is mediated by soluble molecules secreted by licensed NK cells. Licensed NK cell supernatant also dramatically promotes TH17 cells, a signature CD4+ T helper subset in CD. Multiplexed cytokine study of two independent CD and MS disease cohorts demonstrated that genetically licensed and unlicensed NK cells exhibit consistent and distinct cytokine profiles, with licensed NK cells distinguished by high-output, pro-inflammatory, poly-cytokine expression. Selected cytokines among this output account for the unique capacity of licensed NK cells to efficiently augment antigenic CD4+ T cell proliferation and TH17 polarization.

Accordingly, this invention discloses novel methods and kits for detecting the predisposition to chronic inflammatory diseases. This invention further discloses methods of treating of treating and predicting the efficacy of treatment of chronic inflammatory diseases.

Furthermore, this invention represents a significant advancement in the prediction of thiopurine therapy responsiveness relative to other available tools in several ways. For example, it is the first method to predict treatment efficacy based on its immunological mechanism, the first method to relate genetically-coded natural killer cell functionality to treatment efficacy, and it is a minimally invasive sample collection method (i.e., a small amount of blood such as 5 mL blood).

This invention also teaches that DNA can be used to detect the genetic loci for 21 KIR genes and 4 HLA genes.

This invention also teaches flow cytometric methods for screening blood leucocytes as described herein.

This invention also discloses the methods and kit for genetic tests. The genetic test methods and kits may include a user-friendly manual that contains (a) a genetic table that allows the input of 21 KIR genes, HLA class I ligands, including HLA-C1, HLA-C2, HLA-Bw4, and HLA-Bw6; (b) a clear and easy-to-follow instruction or algorithm for genetic table interpretation; (c) the interpretation would be the probability of responding to 6-thiopurine treatment.

This invention also discloses the methods and kit for flow cytometric tests. These methods and kits may contain an immunostaining kit and instruction manual: (a) Reagents and instructions for immunostaining of blood leucocytes (b) Instructions for gating and enumeration of educated NK cells (c) A table of ranges of educated NK cells tieh the probability of responding to 6-thiopurine treatment.

Definitions

As used herein "chronic inflammatory disorder" or a "chronic inflammatory disease" may be defined herein as a disorder wherein at least one of the symptoms is chronic inflammation or wherein the disorder is caused at least in part by chronic inflammation. Chronic inflammation leads to a progressive shift in the type of cells which are present at the site of inflammation and involves destruction of the tissue from the inflammatory process.

Non-limiting examples of chronic inflammatory diseases include chronic gingivitis; chronic periodontitis; chronic autoimmune gastritis; ileitis, including Crohn's disease; inflammatory bowel disease, including colitis and ulcerative colitis; interstitial cystitis; psoriasis; forms of arthritis, including rheumatoid arthritis, ankylosing spondylitis and osteoarthritis; tendinitis or tenosynovitis; carpel tunnel syndrome and other cumulative trauma disorders; Type 1 diabetes; chronic discoid or systemic lupus erythematosus; pneumoconiosis due to inhalation of asbestos particles (asbestosis), inhalation of stone dust or quartz (silicosis) or inhalation of other causitive agents such as graphite, coal dust, particles produced by metal grinding, talc or corn dust; chronic obstructive pulmonary disease; inflammatory myopathies; inflammatory neuropathies; myasthenia gravis; neuromyelitis optica; multiple sclerosis; systemic sclerosis; organ transplant rejection; epilepsy; inflammatory site edema; post-event ischemia and reperfusion symptomology resulting from acute central nervous system trauma, including stroke and spinal cord trauma; post-event consequences of kidney ischemia and reperfusion; and post-event consequences of reperfusion subsequent to myocardial infarction.

In specific embodiments, the term "chronic inflammatory disease" refers to multiple sclerosis, Crohn's disease, ulcerative colitis, rheumatoid arthritis, organ transplant rejection, neuromyelitis optica, myasthenia gravis, psoriasis, systemic sclerosis, and Type 1 diabetes.

As used herein, the term "licensed" or "licensing" or "educate" or "educated" refers to functionally competent NK cells. As described herein, an NK cell is licensed when the KIR2DL2/3 KIR receptor (encoded by the KIR2dL2/3 gene) on the NK cell interacts with an HLA antigen, specifically the HLA-C1 antigen. Upon licensing of the NK cell, CD4+ cell activation and $T_H17$ cell differentiation is promoted.

As used herein, "AA haplotype" refers to individuals with the KIR genotype consisting of the presences of KIR2DL3, KIR2DL1, KIR2DL4, KIR3DL1, KIR3DL2, KIR3DL3, KIR2DS4, KIR2DP1, KIR3DP1, and absent of KIR2DL5, KIR3DL3, KIR2DS1, KIR2DS2, KIR2DS3, DIR2DS4, KIR2DS5, KIR3DS1.

As used herein, "non-AA haplotype" refers to individuals with any KIR genotype other than the AA haplotype KIR genotype.

Figure 21:
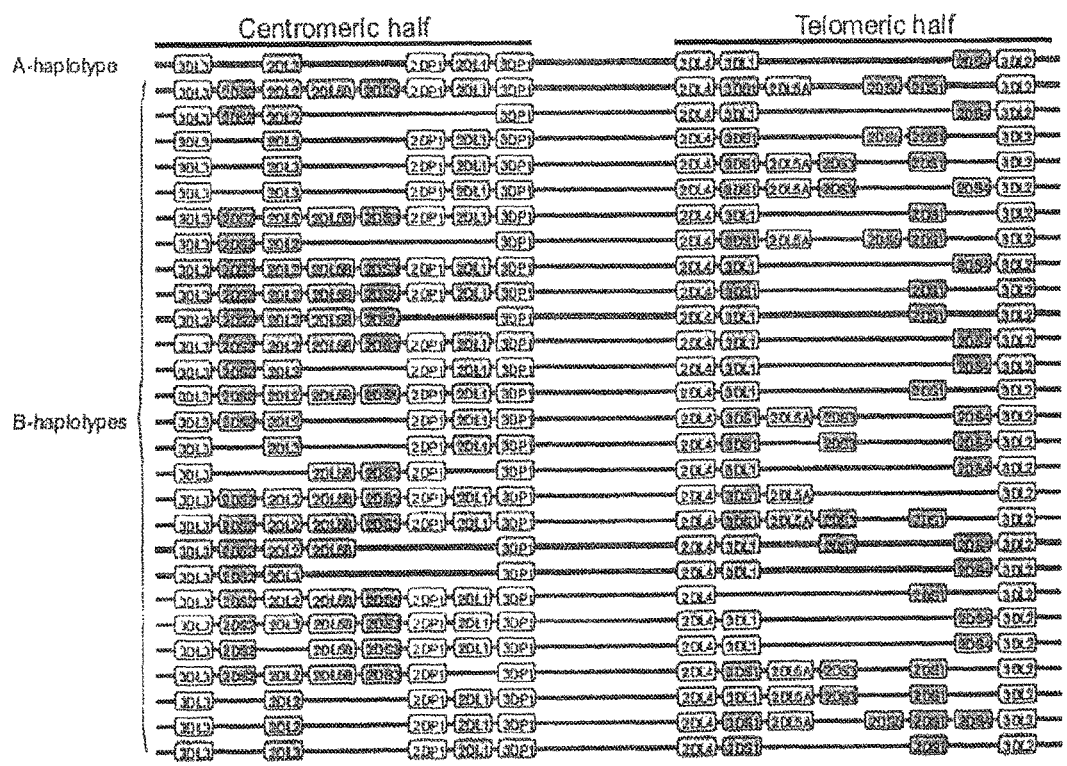
FIG. 21 depicts the complex genetics of KIR. (A) depicts the A and B halotypes and (B) depicts the A halotype alone.
Figure 22:
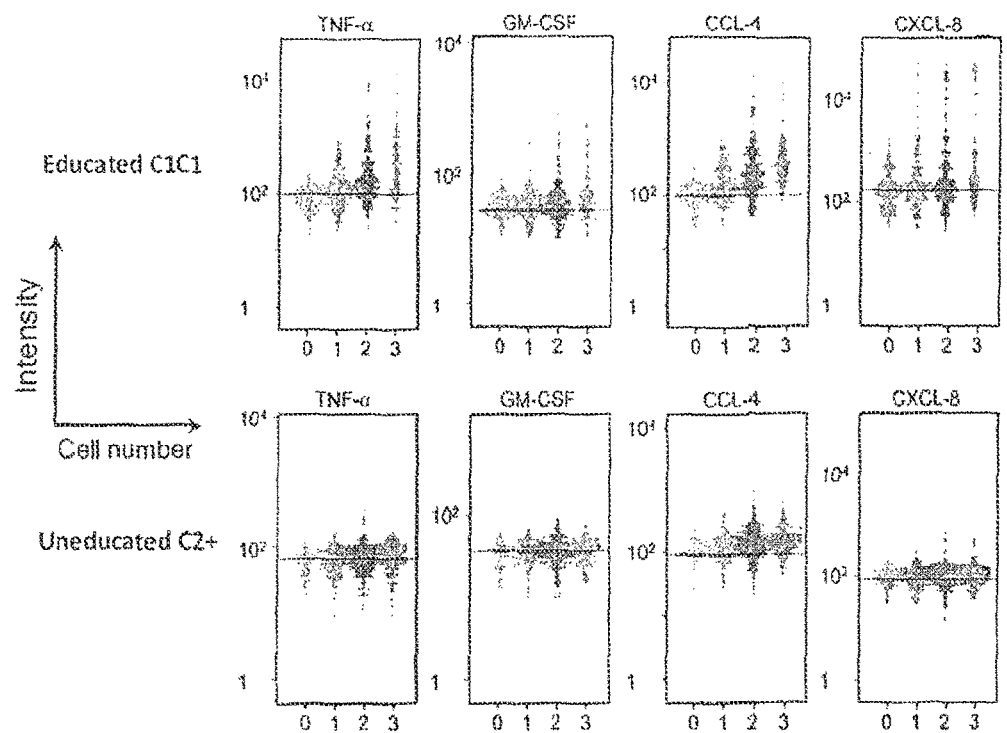
FIGS. 22 (A) and (B) show that licensed NK cells secrete a wide array of cytokines whereas unlicensed NK cells do not.
Figure 22:
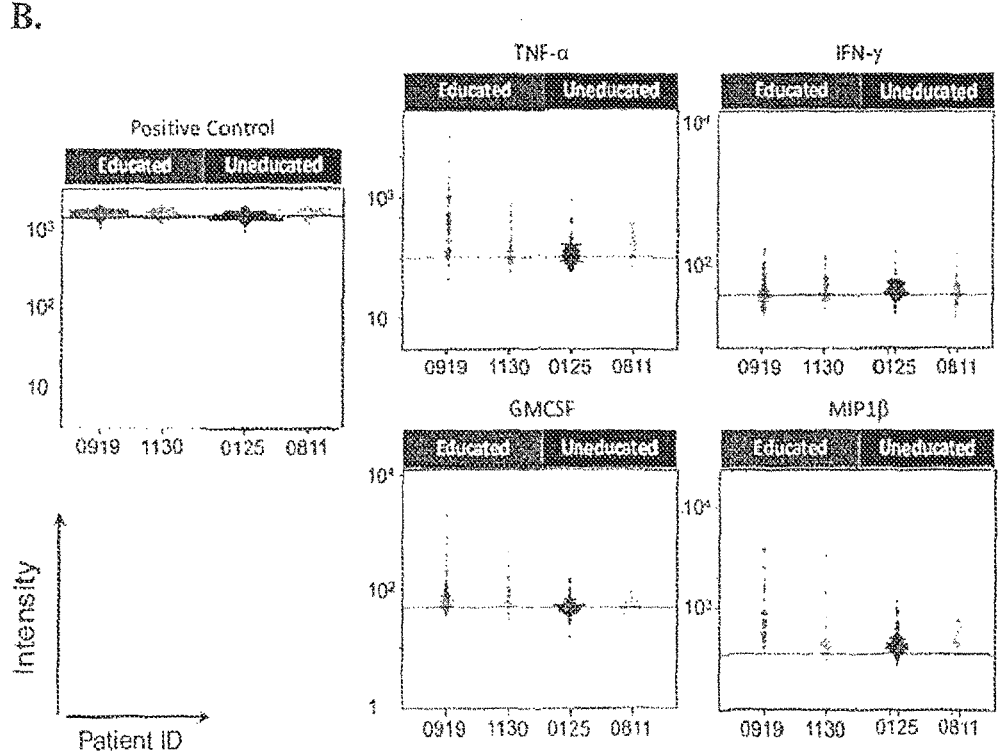
Figure 23:
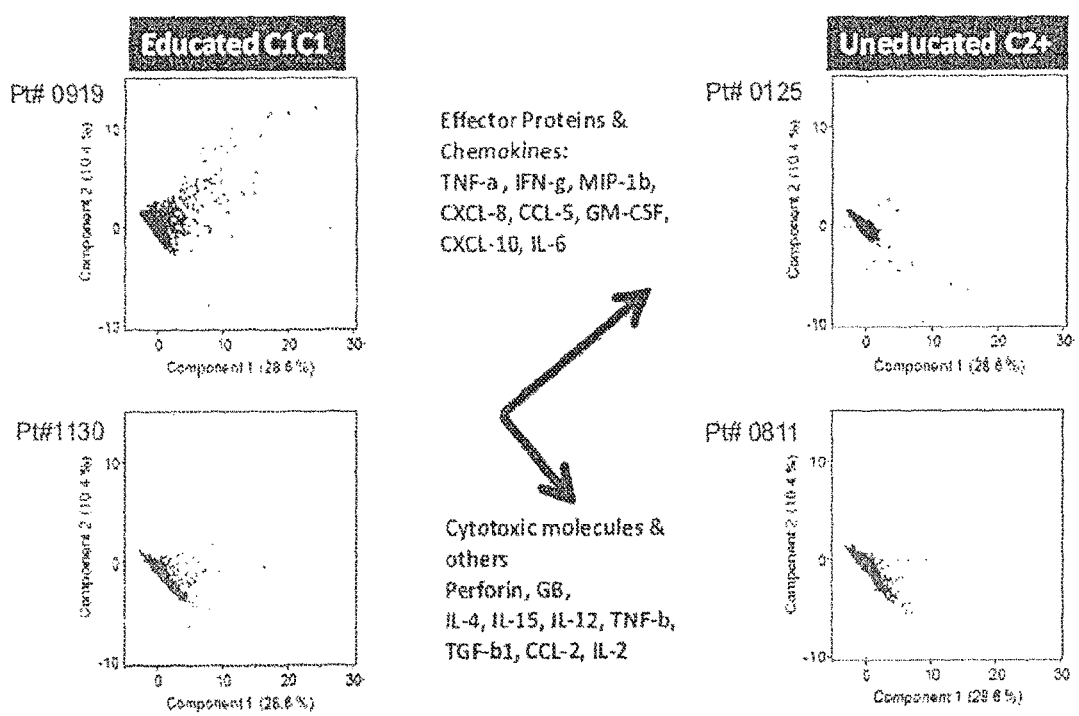
FIG. 23 shows that licensed NK cells show stronger production of effector proteins and chemokines than unlicensed NK cells.
Figure 24:
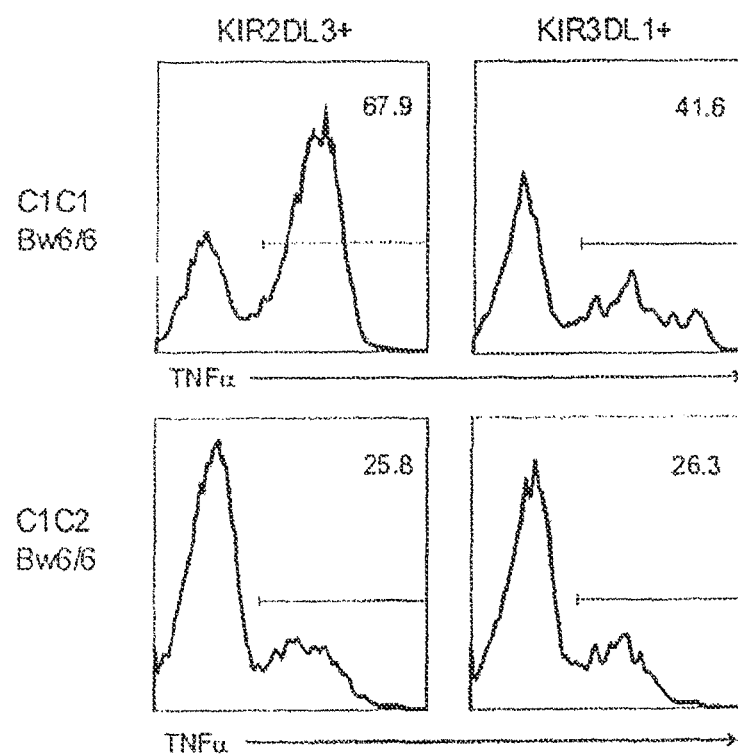
FIG. 24 shows that licensed NK subsets as well as licensed individual NK cells are stronger TNFα producers in healthy cohorts.
Figure 25:
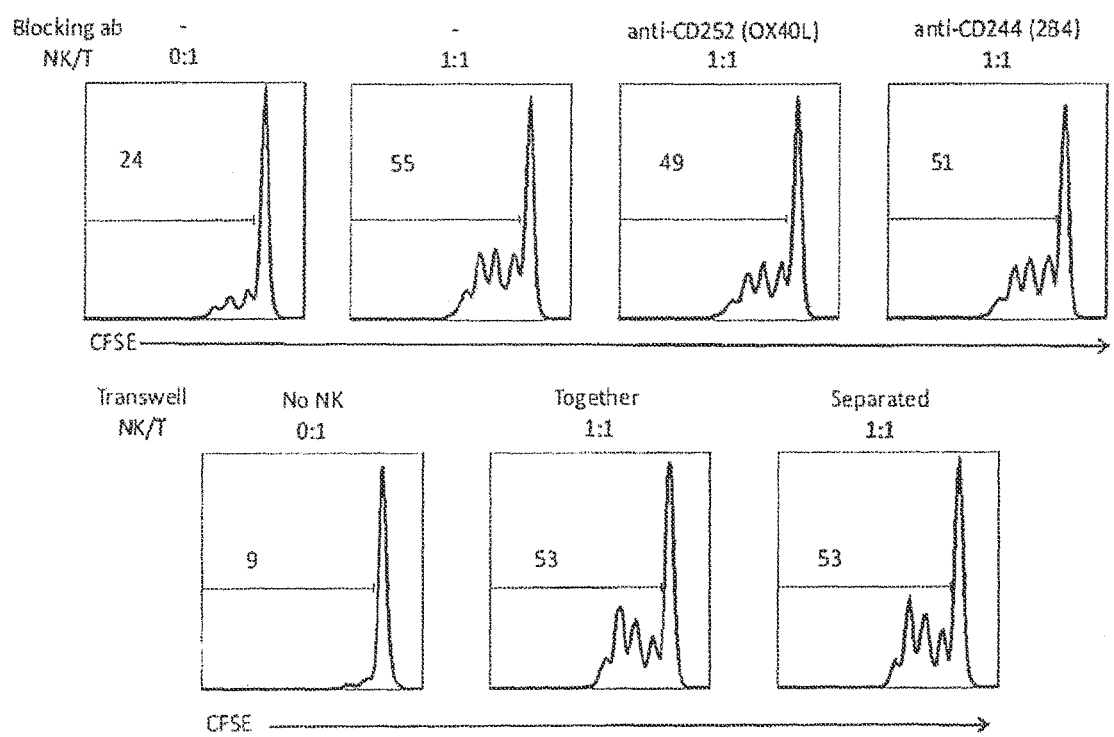
FIG. 25 shows that NK cell helper activity is contact-independent.

As used herein, "KIR/HLA haplotype" refers to KIR and HLA genotype of a patient. For example, FIG. 21 depicts the complex genetics of the KIR haplotypes and FIG. 15 depicts the HLA allotype distribution. Furthermore, examples of KIR/HLA haplotypes include: KIR2DL1 recognizes HLA-C2 allotypes, KIR2DL2 and KIR2DL3 recognize HLA-C1 allotypes, and KIR3DL1 recognizes HLA-B allotypes with the serologically defined Bw4 motif. Furthermore, KIR/HLA haplotypes are provided in Table 3.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "therapy," "therapeutic," "treating," "treat," "treatment," "treatment regimen," or "treatment regime" can be used interchangeably and refer broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and reducing or eliminating existing signs and/or symptoms. Therapy includes treating chronic disease ("maintenance") and acute disease. For example, treatment includes treating or preventing relapses or the recurrence of signs and/or symptoms (e.g., inflammation, pain).

Treatments include anti-inflammatory drugs (e.g., sufasalazine, mesalamine, NSAIDs, ImSAIDs, and corticosteroids), immune system suppressors (e.g., azathioprine, mercaptopurine, infliximab, adalimumab, certolizumab pegol, methodtrexate, cyclosporine, and natalizumab), antibiotics (e.g., metronidazol and ciprofloxacin), anti-diarrheals, laxatives, pain relievers, iron supplements, nutritional plan, vitamin B-12 shots, 6-thiopurine therapy, and surgery.

In certain embodiments the treatment regimen can include one or more of the above described treatments. In certain embodiments, the treatment regimen includes 1 or 2 or 3 or 4 or 5 or 6 or 7 or 8 or 9 or 10 or more of the above described treatments.

In certain embodiments, the treatment regimen can be modified based on a patient's genotype. Specifically, the treatment regimen can be modified based on whether a patient has the genetic predisposition for developing a chronic inflammatory disease based on NK cell licensing as described herein.

As used herein, "symptoms" of a disease refers broadly to any morbid phenomenon or departure from the normal in structure, function, or sensation, experienced by the patient and indicative of disease.

As used herein, "likelihood of responding" or "likely to respond" or "level of response" refers to the likelihood a patient will respond to treatment based on the strength of NK cell education or NK cell licensing (Table 3). For example, as described herein, cytokine signatures and KIR/HLA haplotypes can be used to determine the likelihood of a patient responding to therapy.

As used herein, "solid support," "support," and "substrate" refer broadly to any material that provides a solid or semi-solid structure with which another material can be attached including but not limited to smooth supports (e.g., metal, glass, plastic, silicon, and ceramic surfaces) as well as textured and porous materials.

As used herein "diagnostic" refers broadly to identifying the presence or nature of a pathologic condition. Diagnostic methods differ in their sensitivity and specificity. The "sensitivity" of a diagnostic assay is the percentage of diseased individuals who test positive (percent of "true positives"). While a particular diagnostic method may not provide a definitive diagnosis of a condition, it suffices if the method provides a positive indication that aids in diagnosis.

As used herein, "diagnosing" refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, "predisposition" or "predispose" refers to the increased likelihood or susceptibility of a patient acquiring or developing a disease. For example, it is known in the art that a patient with irritable bowel syndrome is predisposed to eventually developing Crohn's disease. Similarly, as disclosed herein, AA haplotype patients may have an increased likelihood of developing a chronic inflammatory disease and may accordingly be predisposed to chronic inflammatory disease symptoms based on that haplotype.

As used herein, "immunoassay" refers broadly to an assay that uses an antibody to specifically bind an antigen. The immunoassay may be characterized by the use of specific binding properties of a particular antibody to isolate, target, and/or quantify the antigen. A non-limiting example of an immunoassay described herein is an ELISA.

As used herein, "patient" or "subject" refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient." In preferred embodiments, a patient is a human.

As used herein, "6-thiopurine therapy" and "6-thioguanine therapy" refers to the family of thiopurine and thioguanine drugs. These terms can be used interchangeably within this disclosure to encompass a broad class of drugs that kill NK cells. Thiopurine drugs are purine antimetabolites which are routinely used in the treatment of autoimmune disorders such as Crohn's disease and rheumatoid arthritis. 6-thioguanine (6-TG), mercaptopurine, and azathioprine also belong to the family of thiopurine drugs. As used herein, 6-thiopurine, 6-TG, mercaptopurine, and azathiprine therapies can be used interchangeably.

Pro-Inflammatory Role of NK Cells on Adaptive Immunity

The genetic presence of strong NK licensing KIR/ligand pairs (KIR2DL3/HLA-C1 or KIR3DL1/HLA-Bw4) affects several important chronic inflammatory diseases: elevated susceptibility to CD, Celiac disease, spondyloarthropathy, psoriatic arthritis; enhanced resolution of Hepatitis C virus (HCV) infection, and slower progression in HIV-1 infection (M. P. Martin et al., Cutting edge: susceptibility to psoriatic arthritis: influence of activating killer Ig-like receptor genes in the absence of specific HLA-C alleles. *J Immunol* 169, 2818 (Sep. 15, 2002); S. J. Moodie et al., Analysis of candidate genes on chromosome 19 in coeliac disease: an association study of the KIR and LILR gene clusters. *Eur J Immunogenet* 29, 287 (August, 2002); A. T. Chan, S. D. Kollnberger, L. R. Wedderburn, P. Bowness, Expansion and enhanced survival of natural killer cells expressing the killer immunoglobulin-like receptor KIR3DL2 in spondylarthritis. *Arthritis Rheum* 52, 3586 (November, 2005); P. Brodin, T. Lakshmikanth, K. Karre, P. Hoglund, Skewing of the NK Cell Repertoire by MHC Class I via Quantitatively Controlled Enrichment and Contraction of Specific Ly49 Subsets. *J Immunol* 188, 2218 (Mar. 1, 2012); D. Zhi et al., Killer cell immunoglobulin-like receptor along with HLA-C ligand genes are associated with type 1 diabetes in Chinese Han population. *Diabetes Metab Res Rev* 27, 872 (November, 2011); K. L. Mehers et al., An increased frequency of NK cell receptor and HLA-C group 1 combinations in early-onset type 1 diabetes. *Diabetologia* 54, 3062 (December, 2011); A. Shastry et al., Combination of KIR 2DL2 and HLA-C1 (Asn 80) confers susceptibility to type 1 diabetes in Latvians. *International journal of immunogenetics* 35, 439 (December, 2008)).

Understanding the nature of KIR contribution to disease susceptibility or protection is crucial for developing diagnostic and treatment strategies. However, biologic study of KIR-mediated disease association has been challenging due to two levels of complexity.

First, it is difficult to dissect the conflicting roles of KIRs in NK cell licensing and in target-induced inhibitory signaling. As disclosed herein, NK cell function was studied independent of target cell interaction, to exclude the role of KIR-mediated inhibitory signaling and thereby focus solely on KIR-mediated NK licensing.

Second, polymorphic composition and functions of KIR haplotypes, and the independent assortment of their cognate HLA class I ligands, confound the biologic study of NK licensing by individual KIRs. By focusing on the simplified AA haplotype, this invention identifies KIR-mediated licensing as a major mechanism to reprogram NK cell cytokine capacity. It is further shown herein that, in accord with the distinct cytokines produced by licensed NK cells, NK cells have the capacity to augment $CD4^+$ T cell activation and TH17 differentiation, which provide a mechanistic basis for their genetic association to chronic inflammatory diseases.

Figure 11:
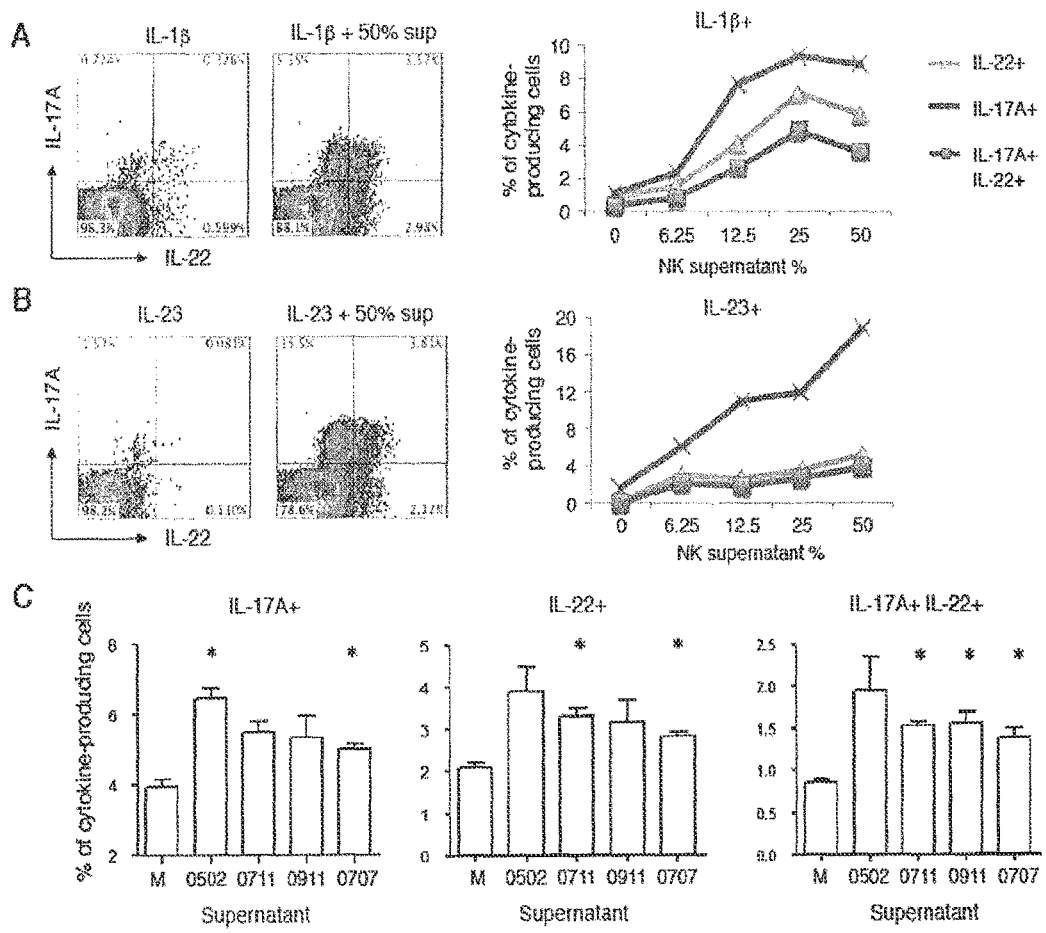
FIG. 11 depicts the supernatant of licensed NK cells drives human TH17 cells differentiation in vitro. Freshly isolated CD4$^+$ T cells from healthy subjects were stimulated with 1 ug mL$^{-1}$ immobilized anti-CD3 and 0.2 ug mL$^{-1}$ soluble anti-CD28, cultured in the presence of indicated cytokine with or without licensed NK cell three-day culture supernatant for 6-7 days. CD4$^+$ T cells were expanded for another 6-7 days in 2 ng mL$^{-1}$ (26 I.U) IL-2 with the same condition provided for priming. (A and B) Left panel: 2D scatter plot of IL-17A and IL-22 intracellular production under the conditions indicated. Numbers in each quadrant represents the percentage of cell in that quadrant. (A and B) Right panel: Line plot of the abundances of IL-22$^+$ (green triangle), IL-17A$^+$ (purple cross), and IL-17A$^+$IL-22$^+$ (red square) populations at different amounts of NK supernatant. This result is representative of three independent experiments. (C) Bar plot of the percentages of IL-17A$^+$ (left panel), IL-22$^+$ (middle panel), and IL-17A$^+$IL-22$^+$ (right panel) CD4$^+$ T cells after differentiating with 50% NK cell supernatants from four different licensed healthy donors. M stands for media with the same amount of IL-2 used for NK three-day culture. All assays have been supplemented with 50 ng mL$^{-1}$ IL-23. (n=2, two-tailed student t test, *p<0.05)
Figure 13:
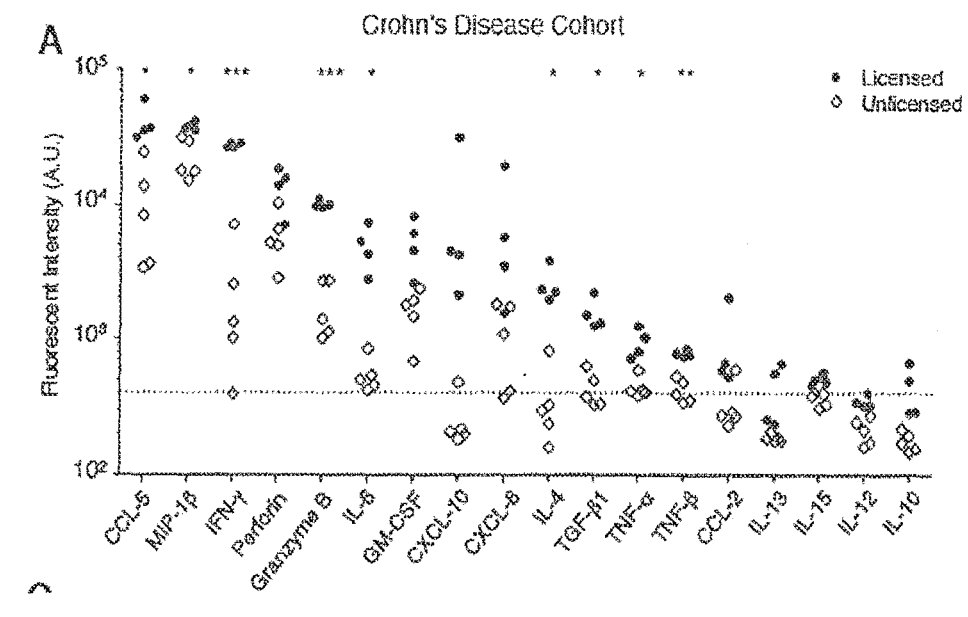
FIG. 13 depicts NK cells from genetically licensed patients have distinct cytokine secretion patterns compared to those from unlicensed patients in bulk culture. (A) Univariate comparison of cytokine production level of bulk culture NK cells from C1C1 (Licensed, solid dot) and C2+ (Unlicensed, open Square) CD patients. The vertical axis shows the fluorescence intensity. (n=4 to 5, P values are calculated using two tailed student t test, adjusted for multiple comparison by FDR, *p<0.05; p<0.005; *p<0.0005). The dash-line indicates the detection threshold. Secretion profiles were measured by multiplex ELISA. (B) Hierarchical clustering of the bulk cytokine production profile of NK cells from C1C1 (red) and C2+ (blue) CD patients. Each row represents one protein indicated on the right, and each column represents one patient. (n=4 to 5). (C) Univariate comparison of cytokine production from licensed (all C1C1 and all Bw4/Bw4, red solid dot) and unlicensed (all other genotype, open square) MS patients. (n=8 to 19, P values are calculated using two tailed student t test, adjusted for multiple comparison by FDR, *p<0.05; **p<0.005). The dash line shows the detection threshold.
Figure 13:
Figure 13:
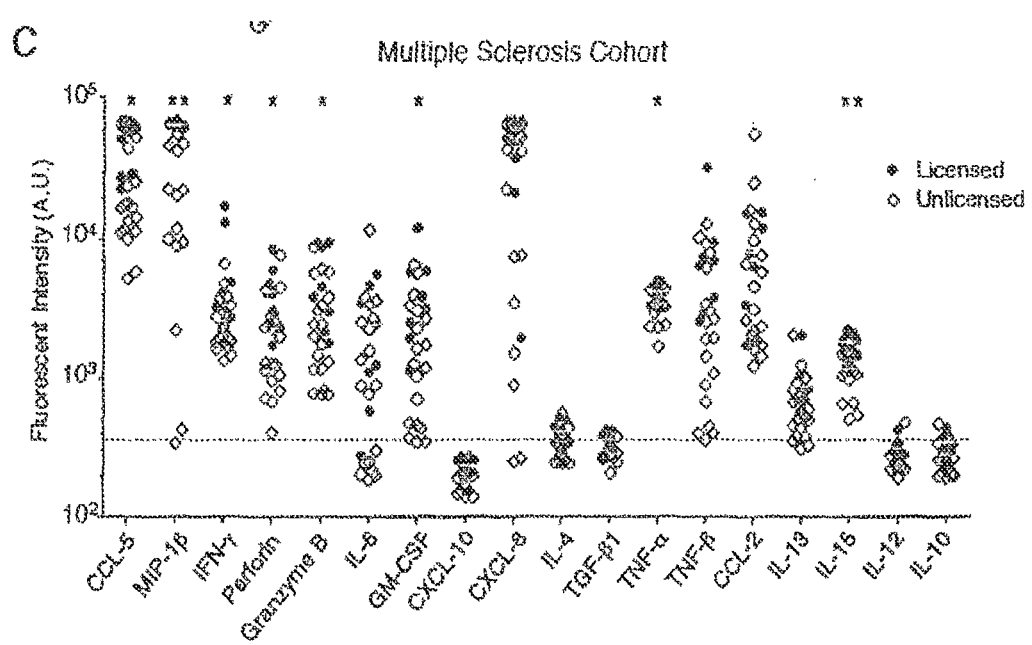

The distinct NK cytokine program induced by KIR licensing appears to be a genetic trait independent of disease status. Thus, NK cell licensing was preserved in two independent patient cohorts, CD and MS (FIGS. 13A and 13B); and functionally, licensed NK cell cytokines from both CD and healthy subjects comparably augmented $CD4^+$ T cell polarization (FIG. 11). While the licensing-associated cytokine program was preserved among all cohorts, it is notable that there were significant differences in the detailed NK cell cytokine production in the CD and MS cohorts: GM-CSF, perforin, and IL-15 in the MS cohort; IL-6, IL-4, and TNF-13 in the CD cohort. These differences may be due to the impact of non-A haplotype KIR genes included in the MS cohort (A. K. Moesta, P. Parham, Diverse functionality among human NK cell receptors for the C1 epitope of HLA-C: KIR2DS2, KIR2DL2, and KIR2DL3. *Front Immunol* 3, 336 (2012); M. Yawata et al., Roles for HLA and KIR polymorphisms in natural killer cell repertoire selection and modulation of effector function. *J Exp Med* 203, 633 (Mar. 20, 2006)); the larger size of the MS cohort; and, disease- or treatment-related effects on the NK cell population.

A striking finding of this invention is the selective capacity of licensed NK cell cytokines to efficiently drive IL-17A and IL-22 production, as well as populations co-expressing IL-17A and IL-22. This is in part attributable to IL-6, a cytokine produced by licensed NK cells known to be important in TH17 polarization. However, other NK-produced cytokines may be relevant, since in several culture conditions, TH17 polarization by NK cell supernatants exceeded that expected for IL-6 alone. Through IL-6 (and perhaps other cytokines), licensed NK cells synergize with IL-23 and IL-113 to facilitate TH17 differentiation, indicating that licensed NK cell secretions can collaborate with other cells in the local tissue compartment (dendritic cells or macrophages) to promote a more pro-inflammatory environment shaping $CD4^+$ or $CD8^+$ T cell responses (H. P. Raue, C. Beadling, J. Haun, M. K. Slifka, Cytokine-mediated programmed proliferation of virus-specific CD8(+) memory T cells. *Immunity* 38, 131 (Jan. 24, 2013); M. J. Richer, J. C. Nolz, J. T. Harty, Pathogen-specific inflammatory milieux tune the antigen sensitivity of CD8(+) T cells by enhancing T cell receptor signaling. *Immunity* 38, 140 (Jan. 24, 2013)).

The fundamental mechanism by which NK licensing yields a distinct NK cell cytokine program is still emerging. Recent work indicates that upon NK licensing, activating NK cell receptors become dynamically compartmentalized in membrane nanodomain that permits full signaling reactivity (S. Guia et al., Confinement of activating receptors at the plasma membrane controls natural killer cell tolerance. *Sci Signal* 4, ra21 (2011)). In mice and humans, licensed NK cells gain higher sensitivity to cytokine stimulation (A. A. Bashirova, R. Thomas, M. Carrington, HLA/KIR restraint of HIV: surviving the fittest. *Annu Rev Immunol* 29, 295 (2011); E. Vivier, E. Tomasello, M. Baratin, T. Walzer, S. Ugolini, Functions of natural killer cells. *Nat Immunol* 9, 503 (May, 2008); P. Brodin, T. Lakshmikanth, K. Karre, P. Hoglund, Skewing of the NK Cell Repertoire by MHC Class I via Quantitatively Controlled Enrichment and Contraction of Specific Ly49 Subsets. *J Immunol* 188, 2218 (Mar. 1, 2012)), but how the intracellular signaling network is rewired after NK licensing is unknown.

The inter- and intra-individual analysis of KIR-mediated licensing described herein indicates that this rewiring affects a remarkably broad range of cytokines, which poses further challenges and conditions to the underlying mechanism of NK licensing. The exceptional breadth and pro-inflammatory cytokine profile of licensed NK cell is an important finding of this study, as well as evidence that this cytokine production lowers the threshold for $CD4^+$ T cell activation. It is also conceivable that licensed NK cells, through their robust cytokine production, may contribute to the initiation of the pro-inflammatory process prior to the innate or immune activation of dendritic cells and macrophages (A. A. Bashirova, R. Thomas, M. Carrington, HLA/KIR restraint of HIV: surviving the fittest. *Annu Rev Immunol* 29, 295 (2011); N. Anfossi et al., Human NK cell education by inhibitory receptors for MHC class I. *Immunity* 25, 331 (August, 2006)). This pro-inflammatory role of NK cells on adaptive immunity offers a fresh biologic mechanism accounting for the impact of KIR-HLA genetics on chronic inflammatory disease and resistance to certain viral infection.

Natural Killer (NK) Cells

NK cells are large granular lymphocytes that participate in immune reactions. NK cells act as cytotoxic immune cells. Specifically, the cytotoxic activity mediated by NK cells naturally against target cells (e.g., cancer cells, virally infected cells) is generally expressed a being the result of a "balance" of positive and negative signals transmitted respectively by activating and inhibitory cell surface receptors.

NK cells represent a distinct population of lymphocytes in terms of both phenotype and function. NK cells have a large granular lymphocyte morphology and express characteristic NK cell surface receptors, and lack both TCR rearrangement and T cell, B cell, monocyte and/or macrophage cell surface markers.

NK cells can be identified by any number of known cell surface markers which vary between species (e.g., in humans CD56, CD16, NKp44, NKp46, and NKp30 are often used; in mice NK1.1, Ly49A-W, CD49b are often used). In an active state, NK cells are capable of killing certain autologous, allogeneic, and even xenogeneic tumor cells, virus-infected cells, certain bacteria (e.g., *Salmonella typhi*), and other target cells. NK cells appear to preferentially kill target cells that express little or no Major Histocompatibility Class I (MHCI or MHC-I) molecules on their surface. NK cells also kill target cells to which antibody molecules have attached, a mechanism known as antibody-dependent cellular cytotoxicity (ADCC). In action against target cells, NK cells can release pore-forming proteins called perforins, proteolytic enzymes called granzymes, and cytokines/chemokines (e.g., TNFα, IFNγ) that directly lead to target cell apoptosis or lysis, or that regulate other immune responses. Upon activation, NK cells also may express Fas ligand (FasL), enabling these cells to induce apoptosis in cells that express Fas.

Sufficient NK cell activity and NK cell count typically are both necessary to mounting an adequate NK cell-mediated immune response. NK cells may be present in normal numbers in an individual, but if not activated these cells will be ineffective in performing vital immune system functions, such as eliminating abnormal cells. Decreased NK cell activity is linked to the development and progression of many diseases. For example, research has demonstrated that low NK cell activity causes greater susceptibility to diseases such as chronic fatigue syndrome (CFS), viral infections, and the development of cancers.

NK cells kill by releasing small cytoplasmic granules of proteins (perforin and granzyme) that cause the target cell to die by apoptosis. NK cells possess mechanisms distinguishing between potential "target" cells and healthy cells via a multitude of inhibitory and activating receptors that engage MHC class I molecules, MHC class I-like molecules, and molecules unrelated to MHC (Caliguiri Blood 2008 112: 461-69). Inhibitory NK cell receptors include HLA-E (CD94/NKG2A); HLA-C (group 1 or 2), KIR2DL; KIR3DL (HLA-B Bw4) and HLA-A3 or A4+peptide. Activating NK cell receptors include HLA-E (CD94/NKG2C); KIR2DS (HLA-C) and KIR3DS (HLA-Bw4). Other receptors include the NK cell receptor protein-1 (termed NK1.1 in mice) and the low affinity receptor for the Fc portion of IgG (Fc.gamma.RIII; CD16).

"Activating" and "inhibitory" surface receptors control the NK cell's cytotoxic activity. Importantly for therapeutic considerations, NK cell inhibition is required to prevent destruction of normal host tissues by "activated" NK cells, but inhibitory signaling in NK cells appears to be stronger than the activating signals.

In certain embodiments, NK cells are obtained from peripheral blood mononuclear cells ("PMBCs") of the subject to be treated. In particular embodiments, the NK cells are expanded. The term "expanded" as used herein in the context of effector cells (i.e., NK cells) refers to effector cells that are cultured under conditions that promote (i) an increase in the total number of effector cells relative to the number in the starting culture and (ii) the activation of the effector cells. The terms "activate" or "activated" as used herein in relation to effector cells refer to inducing a change in their biologic state by which the cells express activation markers, produce cytokines, proliferate and/or become cytotoxic to target cells. Typically, NK cells are expanded and activated under the culturing conditions described herein.

In certain embodiments, PBMCs are cultured under conditions that promote an increase in the fraction of NK cells and a decrease in the fraction of T-cells and/or NKT cells relative to the starting culture. In some embodiments, PBMCs are cultured under conditions that promote an increase in the fraction of NK cells in the culture and no increase or decrease in the fraction of T-cells and/or NKT cells in the culture relative to the starting culture. In particular embodiments, PBMCs are cultured under conditions that promote expansion of NK cells so that NK cells are the largest fraction of cells in the culture.

Expansion and activation of NK cells can be accomplished by any method known in the art. (See e.g, Cho et al. (2009) Korean J. Lab. Med. 29:89 and U.S. Patent Publication No. 2006/0093605, each of which is incorporated herein by reference in its entirety). In some embodiments, NK cells, e.g., in PBMCs, are cultured in the presence of stimulatory cytokines. Such cytokines include, but are not limited to, IL-2, IL-4, IL-7, IL-12 and IL-15, either alone or in combination. In other embodiments, NK cells are expanded and activated by culturing the cells in the presence of stimulatory molecules such as an anti-CD3 antibody and IL-2.

In certain embodiments expansion and activation of NK cells can also be accomplished by co-culturing the cells with accessory cells. In certain embodiments, such accessory cells include, but are not limited to, monocytes, B-lymphblastoid cells, HFWT cells (a Wilms tumor-derived cell line), allogeneic mononuclear cells, autologous lymphocytes, mitogen activated lymphocytes and umbilical cord mesenchymal cells. In various embodiments, the accessory cells are K562 cells, a cell line derived from a patient with myeloid blast crisis of chronic myelogenous leukemia and bearing the BCR-ABL1 translocation. In certain embodiments, NK cells are co-cultured with accessory cells alone or in the presence of one or more cytokines. In certain embodiments, the cytokines are added to the culture medium. In other embodiments, the cytokines are expressed on the surface of the accessory cells.

In some embodiments, a solid support may be used to expand and activate NK cells instead of accessory cells expressing stimulatory molecules on the cell surface. In certain embodiments, such supports will have attached on the surface one or more molecules capable of binding to NK cells and inducing activation or a proliferative response. In some embodiments, the supports are designed to bind one or more molecules that induce activation of NK cells or a proliferative response when NK cells are passed over the solid support and bind to the one or more molecules. Molecules that induce activation of or a proliferative response from NK cells include, but are not limited to CD137, IL-15, or fragments of either CD137 or IL-15 that retain the ability to induce the desired response. See U.S. Patent Publication No. 2006/0093605, which is incorporated herein by reference in its entirety.

NK cells can be divided into two general categories, "licensed" or "educated" NK cells and "non-licensed" NK cells. Genetic methods and flow cytometric measurements can be used to identify individuals distinguished by the presence of licensed NK cells. These same methods can be used to identify a subset of individuals at elevated risk for Crohn's disease as described herein.

Specifically, this invention describes the novel discovery that patients with licensed NK cells represent the patient subset most likely to benefit from therapy that targets and kills NK cells.

As described herein, 'licensing' of NK cells by specific genetic combinations of KIR and HLA genes results in their functional reprogramming, and permits them to promote CD4$^+$ T cell activation and TH17 differentiation ex vivo. Multiplexed bulk and single cell analysis of cytokine profile established that genetically licensed NK cells had a distinct cytokine profile from unlicensed NK cells, including polarized production of interferon (IFN)-γ, tumor necrosis factor (TNF)-α, chemokine (C—C motif) ligand (CCL)-5, and macrophage inflammatory protein (MIP)-1β. These functional attributes of licensed NK cells were genetically rather than disease-defined, as they were observed in genetically licensed cohorts of healthy subjects, CD patients, and multiple sclerosis (MS) patients. Licensed NK cytokines augmented $CD4^+$ T cell proliferation and interleukin (IL)-17A/IL-22 production. Antibody blocking indicated a primary role for IFN-y, TNF-α, and IL-6 in the augmented T cell proliferative response. In conclusion, NK licensing mediated by KIR2DL2/3 and HLA-C1 elicits a novel NK cytokine program that activates and induces pro-inflammatory $CD4^+$ T cells, thereby providing a biological mechanism for KIR-associated susceptibility to CD and other chronic inflammatory diseases.

Killer Cell Immunoglobulin-Like Receptor (KIR)

KIRs are cell surface glycoproteins, comprising one to three extracellular immunoglobulin-like domains, which are expressed by some T cells as well as most human NK cells. A number of KIRs are well characterized (See, e.g., Carrington and Norman, The KIR Gene Cluster, May 28, 2003, available through the National Center for Biotechnology Information (NCBI) web site). Human KIRs include KIR2DL and KIR3DL. KIRs may also be referred to by various other names such as CD158e1, CD158k, CD158z, p58 KIR CD158e1 (p70), and CD244 (U.S. Patent Application Publication No. 2004/0038894; Radaev et al., Annu. Rev. Biophys. Biomol. Struct., 32:93-114 (2003); Cerweknka et al., Nat. Rev. Immunol. 1:41-49 (2001); Farag et al., Expert Opin. Biol. Ther., 3(2):237-250 (2003); Biassoni et al., J. Cell. Mol. Med., 7(4):376-387 (2003); and Warren et al., British J. Haematology, 121:793-804 (2003)). The structure of a number of KIRs has been elucidated and reveals remarkable structural similarity between these proteins.

KIRs can be classified structurally as well as functionally. For example, most KIRs have either two Ig domains (58 kDa KIR2D KIRs), whereas others have three Ig domains (70 kDa KIR3D KIRs) (sometimes respectively referred to as p58 and p70 molecules). KIRs vary also in cytoplasmic tail length. Typically, KIRs with a relatively long cytoplasmic tail (L) deliver an inhibitory signal, whereas KIR with a short cytoplasmic tail (S) can activate NK or T cell responses. Nomenclature for KIRs accordingly can be based upon the number of extracellular domains (KIR2D or KIR3D) and whether the cytoplasmic tail is long (KIR2DL or KIR3DL) or short (KIR2DS or KIR3DS).

KIRs can bind MHC-I molecules (e.g., certain HLA class I allotypes), typically resulting in the transmission of a negative signal that counteracts, and may override stimulatory, activating signal(s) to the NK cell, thereby preventing the NK cell from killing the associated potential target cell. Because viruses often suppress class I MHC expression in cells they infect, such virus-infected cells become susceptible to killing by NK cells. Because cancer cells also often have reduced or no class I MHC expression, these cells, too, can become susceptible to killing by NK cells. Infected cells can also change the proteins bound in the MHC in terms of glycosylation. If this occurs, the MHC-I:protein complex the cell expresses will be altered. If NK-associated KIRs cannot bind to these "foreign" complexes, no inhibitory signal can be generated, and lysis will proceed.

In humans, KIRs having two Ig domains (KIR2D) recognize HLA-C allotypes: KIR2DL2 (formerly designated p58.2) and the closely related gene product KIR2DL3 both recognize an epitope shared by group 1 HLA-C allotypes (Cw1, 3, 7, and 8), whereas KIR2DL1 (p58.1) recognizes an epitope shared by the reciprocal group 2 HLA-C allotypes (Cw2, 4, 5, and 6). One KIR with three Ig domains, KIR3DL1 (p70), recognizes an epitope shared by HLA-Bw4 alleles. Lastly, a homodimer of molecules with three Ig domains, KIR3DL2 (p140), recognizes HLA-A3 and -A11.

Individual MHC-1-specific NK cell receptors of either type (activating or inhibitory) typically do not interact with all MHC class I molecules, but specifically bind to certain allotypes (proteins encoded by different variants of a single genetic locus). Also, an individual NK cell may express several different inhibitory and/or activating receptors which function independently of each other. For example, in humans the presence or absence of a given KIR is variable from one NK cell to another within a single individual. There also is relatively high level of polymorphism of KIRs in humans, with certain KIR molecules being present in some, but not all individuals. Although KIRs and other MHC-recognizing inhibitory receptors may be co-expressed by NK cells, in any given individual's NK repertoire there are typically cells that express a single KIR; accordingly, the corresponding NK cell activity in this latter type of NK cells is inhibited only by cells expressing a specific MHC-I allele group. In fact, recent estimates of the extent of KIR genotype diversity within the population suggest that <0.24% of unrelated individuals can expect to have identical genotypes.

Autoimmune Disease

In certain embodiments described herein, the methods and kits of this invention can be used to diagnose, treat, and prevent an autoimmune disease.

An autoimmune disorder is a condition that occurs when the immune system mistakenly attacks and destroys healthy body tissue. There are more than 80 different types of autoimmune disorders. Normally the immune system's white blood cells help protect the body from harmful substances, called antigens. Examples of antigens include bacteria, viruses, toxins, cancer cells, and blood or tissues from another person or species. The immune system produces antibodies that destroy these harmful substances.

However, in patients with an autoimmune disorder, the immune system cannot distinguish between self and non-self (e.g., healthy tissue and foreign antigens). The result is an immune response that destroys normal body tissues. This response is a hypersensitivity reaction similar to the response in allergic conditions.

In allergies, the immune system reacts to an outside substance that it normally would ignore. With autoimmune disorders, the immune system reacts to normal body tissues that it would normally ignore.

An autoimmune disorder may result in the destruction of one or more types of body tissue, abnormal growth of an organ, and changes in organ function. An autoimmune disorder may affect one or more organ or tissue types. Organs and tissues commonly affected by autoimmune disorders include blood vessels, connective tissues, endocrine glands (e.g., thyroid or pancreas), joints, muscles, red blood cells, and skin. A person may have more than one autoimmune disorder at the same time.

Symptoms of an autoimmune disease vary based on the disease and location of the abnormal immune response. Common symptoms that often occur with autoimmune diseases include fatigue, fever, and a general ill-feeling (malaise). Tests that may be done to diagnose an autoimmune disorder may include: antinuclear antibody tests, autoantibody tests, CBC, C-reactive protein (CRP), and erythrocyte sedimentation rate (ESR).

Medicines are often prescribed to control or reduce the immune system's response. They are often called immunosuppressive medicines. Such medicines may include corticosteroids (such as prednisone) and nonsteroid drugs such as azathioprine, cyclophosphamide, mycophenolate, sirolimus, or tacrolimus.

Complications are common and depend on the disease. Side effects of medications used to suppress the immune system can be severe, such as infections that can be hard to control.

Inflammatory Diseases

In certain embodiments described herein, the methods and kits of this invention can be used to diagnose, treat, and prevent an inflammatory disease.

Inflammation is part of the complex biological response of vascular tissues to harmful stimuli, such as pathogens, damaged cells, or irritants. Inflammation is a protective attempt by the organism to remove the injurious stimuli and to initiate the healing process. Without inflammation, wounds and infections would never heal. Similarly, progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

T-cells are involved in the promulgation of inflammation. Differentiation of naive T cells leads to the generation of T-cell subsets, each possessing distinct cytokine expression profiles for serving different immune functions. Through the activation of separate signaling pathways, this process results in both differentiated helper T (Th) cells, termed Th1, Th2 and Th17, and induced regulatory T cells, which suppress Th cells. These different cells are important for combating infectious diseases and cancers; however, when aberrant, they can be responsible for chronic inflammatory diseases. One such disease is inflammatory bowel disease (IBD), in which each T-cell subset can have a role in disease.

While NK cells have received a great deal of attention in the scientific literature for their potential contribution to anti-tumor and anti-viral responses, few studies have been directed to examining the role of NK cells in inflammation and autoimmunity, particularly the KIR2DL1, 2 and/or 3-expressing subsets. The approach toward these NK cells, if anything, has been to seek to eliminate or inhibit NK cells on the basis that they may contribute to inflammation and autoimmunity. The effect of KIR2DL1, 2 and/or 3-mediated potentiating of NK cell cytotoxicity in inflammatory settings has to date not been addressed.

Crohn's Disease

Crohn's disease is an inflammatory bowel disease (IBD). Crohn's disease causes inflammation of the lining of a patient's digestive tract. The inflammation caused by Crohn's disease can be located through the digestive tract and the precise location(s) of the inflammation are patient-specific. For example, the inflammation can occur in the small intestines (e.g., the ileum), the large intestines (e.g., the colon), or the bowel wall (e.g., resulting in stenosis or fistula). In some patients the inflammation is isolated to one area of the digestive tract while in other patients the inflammation is present in two or more areas of the digestive tract.

This inflammation caused by Crohn's disease leads to abdominal pain, diarrhea, bloody stool, ulcers, reduced appetite, weight loss, fever, fatigue, arthritis, eye inflammation, mouth sores, skin disorders, inflammation of the liver or bile ducts, delayed growth or sexual development in children, and malnutrition. While these symptoms may not be present when the disease is in periods of remission, when the disease is active the symptoms can become debilitating and even life-threatening when disease-associated complications arise.

Furthermore, there are multiple disease-related complications that occur in patients with Crohn's disease. For example, because Crohn's disease affects the thickness of the intestinal wall and overtime the bowel can thicken, narrow, and eventually cause a bowel instruction. The chronic inflammation of Crohn's disease may also lead to ulcers throughout the digestive tract. Fistulas can also form when ulcers extend completely through the intestinal wall which can become infected and abscess. Perianal and anal fissures can also occur as a result of the chronic inflammation of Crohn's disease. Malnutrition and anemia can also be caused by diarrhea, loss of appetite, and inability to absorb nutrients. Furthermore, the chronic inflammation to the colon can increase the risk of a patient developing colon cancer.

In addition, Crohn's disease can also cause complications outside of the digestive tract. For example, Crohn's disease may cause arthritis, inflammation of the eyes or skin, clubbing of the fingernails, kidney stones, gallstones, inflammation of the bile ducts, and osteoporosis.

Risk factors for Crohn's disease may include age, ethnicity, family history, cigarette smoking, and environmental factors (e.g., pollution and diets high in fat or refined foods). Most patients who develop Crohn's disease are diagnosed as children or young adults, i.e., before they are 30 years old. Furthermore, because there is a genetic component and predisposition to Crohn's disease as described herein, patients are at an increased risk of developing the disease if they have a family member who is also afflicted with the condition.

There is no cure for Crohn's disease and treatment efficacy is patient dependent. The goal of treatment is to reduce the inflammation that triggers the symptoms, limit disease-related complications, and improve long-term prognosis. Because treatment regimes vary based on an individual patient's responsiveness, treatment plans often include anti-inflammatory drugs (e.g., sufasalazine, mesalamine, and corticosteroids), immune system suppressors (e.g., azathioprine, mercaptopurine, infliximab, adalimumab, certolizumab pegol, methodtrexate, cyclosporine, and natalizumab), antibiotics (e.g., metronidazol and ciprofloxacin), anti-diarrheals, laxatives, pain relievers, iron supplements, nutritional plan, vitamin B-12 shots, 6-thiopurine therapy, and surgery. However, many of these treatment regimes have their own side effects. For example, immune system suppressors are associated with an increased risk of developing cancer such as lymphoma.

Accordingly, because Crohn's disease is a lifelong, chronic disease that often presents symptoms in adolescents, there is a need to develop targeted therapies to treat the disease and minimize or eliminate unnecessary therapies that have detrimental side effects.

Thiopurine and Thioguanine Therapy

Thiopurine and thioguanine therapy is effective for the treatment of some individuals with chronic inflammatory diseases, including inflammatory bowel disease (e.g., Crohn's disease), psoriasis, rheumatoid arthritis and transplant rejection. In certain embodiments, the therapy is 6-thiopurine therapy, 6-thiguanine therapy, mercaptopurine therapy, or azathioprine therapy. While this class of drugs are effective at treating the symptoms of chronic inflammation, they also have serious side effects. For example, thiopurine therapy may cause leukopenia, neutropenia, thrombocytopenia, anemia, anorexia, nausea, and hepatotoxicity. Accordingly, the therapeutic challenge is to identify which individuals may benefit from this therapy, since these agents have toxicity, and their use supplant other treatment choices until their efficacy or lack thereof is established clinically.

While 6-thioguanine is an effective therapy for a variety of chronic inflammatory diseases in some patients, other patients do not respond to the therapy (E. Prefontaine, J. K. Macdonald, L. R. Sutherland, Azathioprine or 6-mercaptopurine for induction of remission in Crohn's disease. Cochrane Database Syst Rev, CD000545 (2010)). Since the cellular target of 6-thioguanine therapy has been uncertain, measurements to assess the suitability of patients for this relatively toxic therapy are unavailable. The molecular target of 6-thioguanine is the small G protein Rac1 in various lymphocyte cell types (I. Tiede et al., CD28-dependent Rac1 activation is the molecular target of azathioprine in primary human CD4+ T lymphocytes. J. Clin. Invest 111, 1133 (2003)). Among these cell types, a prominent candidate is NK cells; which compared to other lymphoid cell types, are quickly and profoundly depleted by 6-thioguanine therapy (M. Brogan et al., The effect of 6-mercaptopurine on natural killer-cell activities in Crohn's disease. J Clin Immunol 5, 204 (May, 1985)). However, levels of NK cells or their depletion by 6-thioguanine do not predict clinical responsiveness. Moreover, the literature provides minimal and conflicting guidance on the role of NK cells in chronic inflammatory diseases (P. Parham, MHC class I molecules and KIRs in human history, health and survival. Nat Rev Immunol 5, 201 (March, 2005); O. Yamaji et al., The Development of Colitogenic CD4+ T Cells Is Regulated by IL-7 in Collaboration with NK Cell Function in a Murine Model of Colitis. J Immunol 188, 2524 (Mar. 15, 2012); M. M. Fort, M. W. Leach, D. M. Rennick, A role for NK cells as regulators of CD4+ T cells in a transfer model of colitis. J Immunol 161, 3256 (1998)).

Genetic polymorphism in thiopurine methyltransferase (TPMT), an enzyme that methylates 6-thiopurine agents (6-mercaptopurine and azathioprine, control metabolic clearance of 6-thiopurines, and predicts the dosing level required for safe and therapeutically effective levels of 6-thiopurine agents. Both genetic testing and enzymatic assays are widely used as clinical laboratory tests to decide on optimal dosing regimens for patients selected for 6-thiopurine therapy. While these tests are useful for safe dosing of these agents, they do not predict if a patient will benefit from 6-thiopurine therapy.

The cellular target of 6-thioguanine therapy is unclear, so measurements to assess suitability of this therapy are unavailable. One potential target is the NK cell, due to its exquisite sensitivity to 6-thioguanine and 6-thiopurine therapy.

Furthermore, 6-thioguanine and 6-thiopurine therapy profoundly affect NK cells, causing NK cell death. Accordingly, methods disclosed herein can be used to identify patients who are predisposed to chronic inflammatory diseases due to NK cell licensing and treatment regimes that may include a 6-thioguanine or 6-thiopurine therapy to kill the NK cells and prevent the CD4+ cell activation and $T_H17$ differentiation through the NK cell licensing pathway. Furthermore, because drugs that kill NK cells such as 6-thioguanine and 6-thiopurine therapy have undesired side effects, methods disclosed herein can determine if the a patient's chronic inflammation is due to NK cell licensing and, where the inflammation is not due to NK cell licensing, treatment can be adjusted accordingly. For example, if a patient's chronic inflammation is not due to NK cell licensing, a treatment regimen can be adjusted to not include drugs targeted to kill NK cells such as 6-thioguanine and 6-thiopurine.

Kits

Also within the scope of the invention are kits.

In certain embodiments, the kits contain necessary reagents and the method for diagnosis, monitoring or assessing chronic inflammatory disease (e.g., Crohn's disease) using an immunoassay such as an ELISA, a western blot, a protein array, a reverse phase protein array, a single cell barcode chip, flow cytometry, a single cell cytokine analysis assay, immunofluorescent staining, or any other means of detecting cytokine expression in cells known to one of skill in the art.

In certain embodiments the kit comprises probe(s), wherein the probe(s) are attached to a solid support. This solid support preferably comprises beads (more preferably, immunobeads), a gel (e.g., agarose or polyacylamide gel), or any array-type solid matrix such as a slide made of distinct materials, such as glass with or without a gold-covered surface.

As described herein, the kits may include instructions, directions, labels, marketing information, warnings, or information pamphlets.

In another preferred embodiment, the probes are antibodies used to recognize the protein of the present invention, or a fragment thereof. The antibodies can be monoclonal or polyclonal.

In another preferred embodiment, the probes are used to recognize IFN-γ, TNF-α, and IL-6.

Materials and Methods

Clinical Samples.

Figure 14:
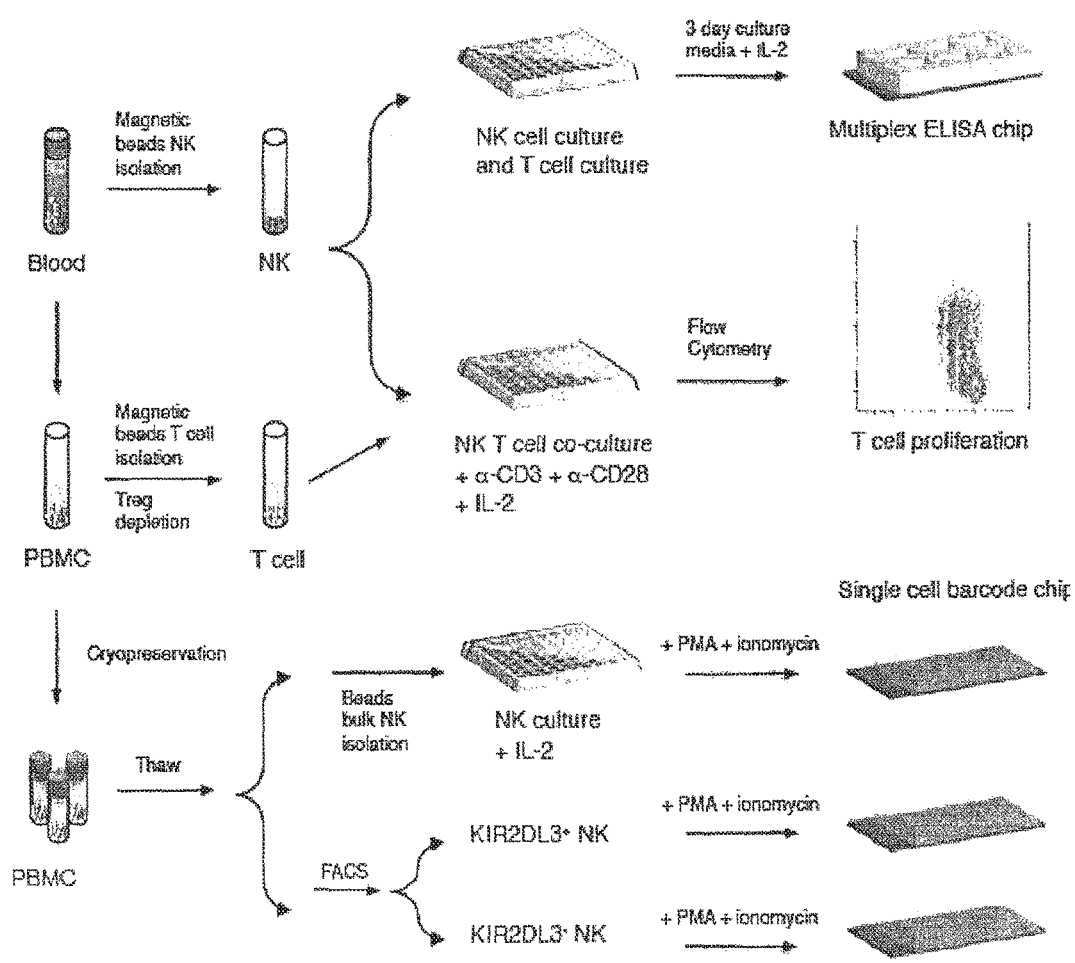
FIG. 14 depicts the CD patient blood sample processing pipeline and immune monitoring technologies utilized. Whole blood samples were used for direct isolation of CD56+NK cells and PBMC, followed by T cell isolation with depletion of Tregs. NK cells and Treg-depleted T cells were put in cocultured or separately, with 2 ng mL$^{-1}$(26 I.U.) IL-2 and antigenic stimulation for T cells as indicated. CD4+ T cell proliferation was subsequently analyzed by flow cytometry. NK and T cell supernatant were analyzed using multiplex ELISA chip within one batch. Aliquots of PBMC were cryo-presevered, and thawed for SCBC analysis with or without presorting.
Figure 16:
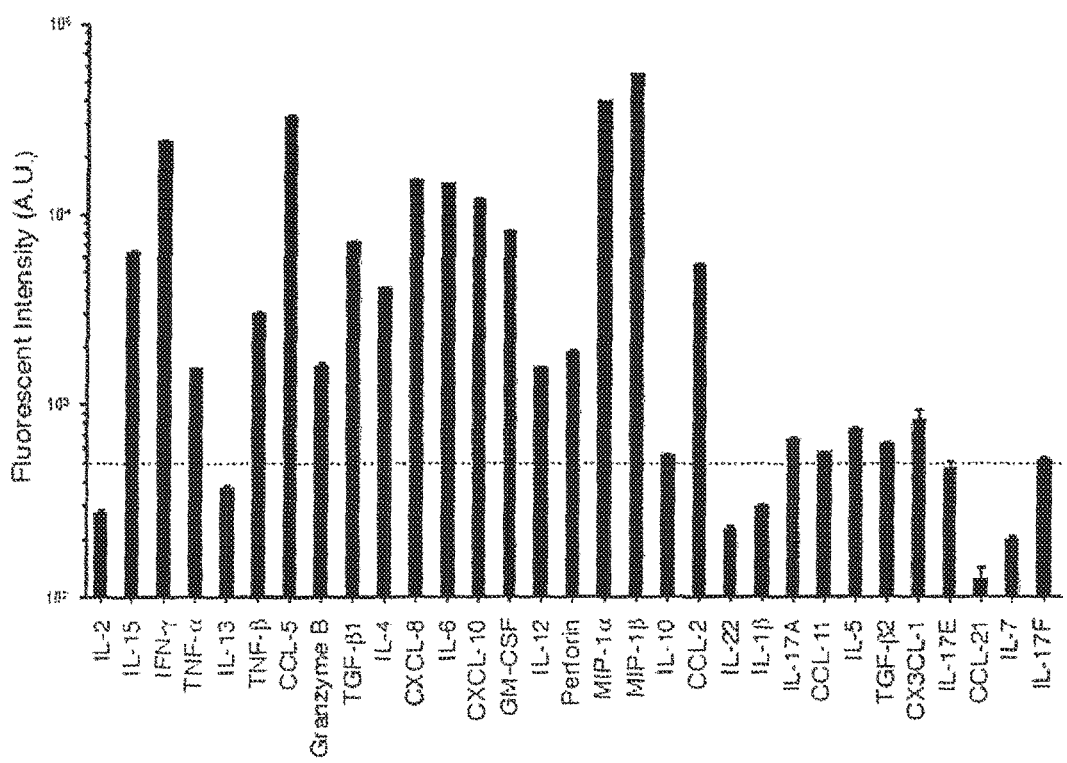
FIG. 16 depicts the screening of NK protein secretion profile using multiplex ELISA chip. Barplot of florescence intensity (Mean±s.e.m, A.U. arbitrary unit) of an initial panel of 31 protein markers from three-day NK culture media, n=8. The dash line shows the detection threshold at 500 A.U.
Figure 17:
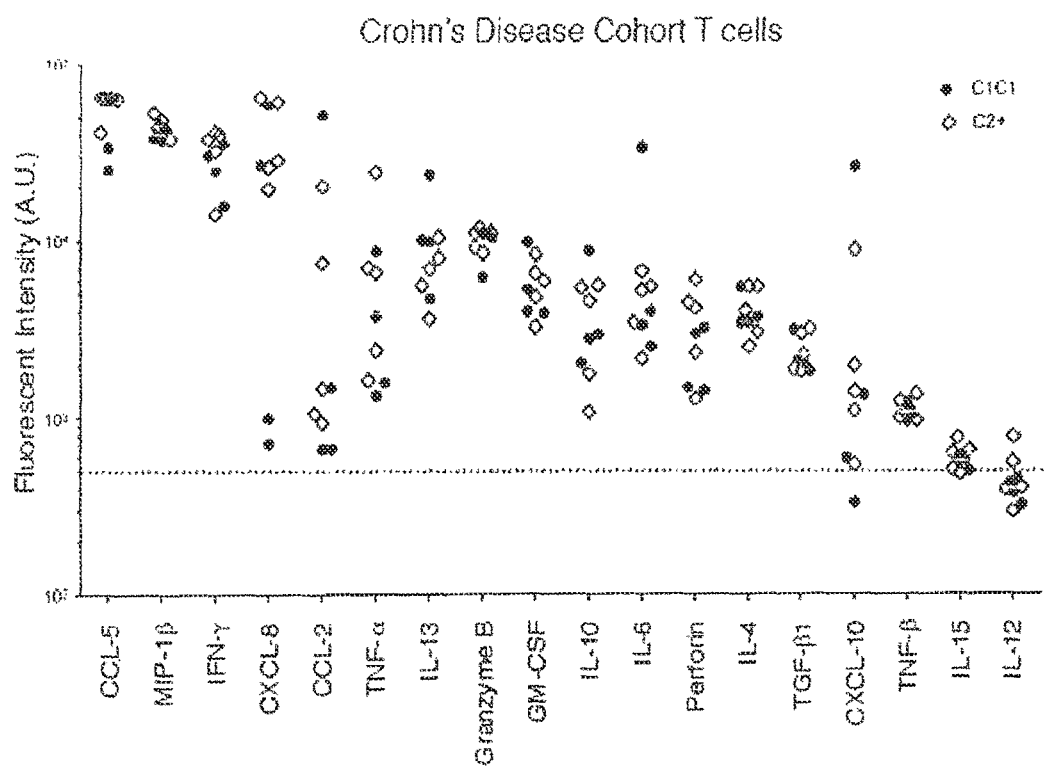
FIG. 17 depicts the AA haplotype C1C1 CD patient T cells have similar cytokine production levels as C2+ patient. T cells were stimulated with 1.5 ug/mL immobilized anti-CD3/CD28, and 2 ng/ml IL-2 for three days. Y axis shows the fluorescence intensity of each cytokine from T cell supernatant. n=4 to 5. Solid dot: C1C1, Open Square: C2+. The dash line shows the detection threshold at 500 A.U.
Figure 18:
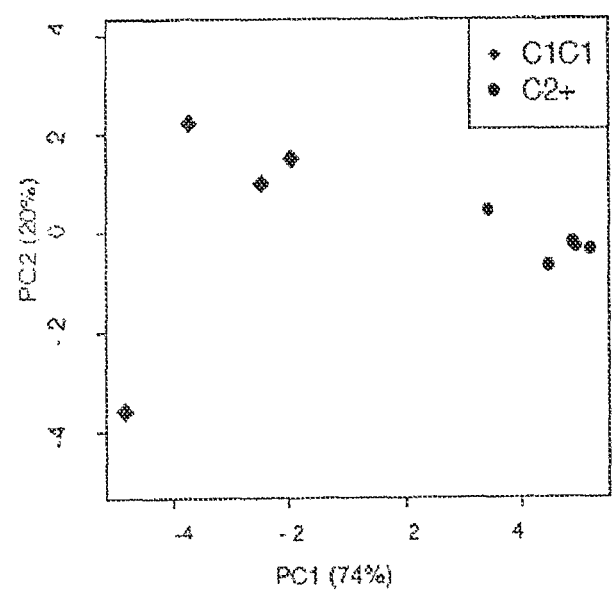
FIG. 18 depicts the distinct secretion profiles of C1C1 and C2+NK cells from AA haplotype CD cohort. Principal Component Analysis of normalized C1C1 and C2+NK three-day culture supernatant secretion profiles, represented by the first two components. The percent of variation explained by each components were shown in parentheses. n=4 to 5, C1C1 (red square), C2+(blue dot).
Figure 19:
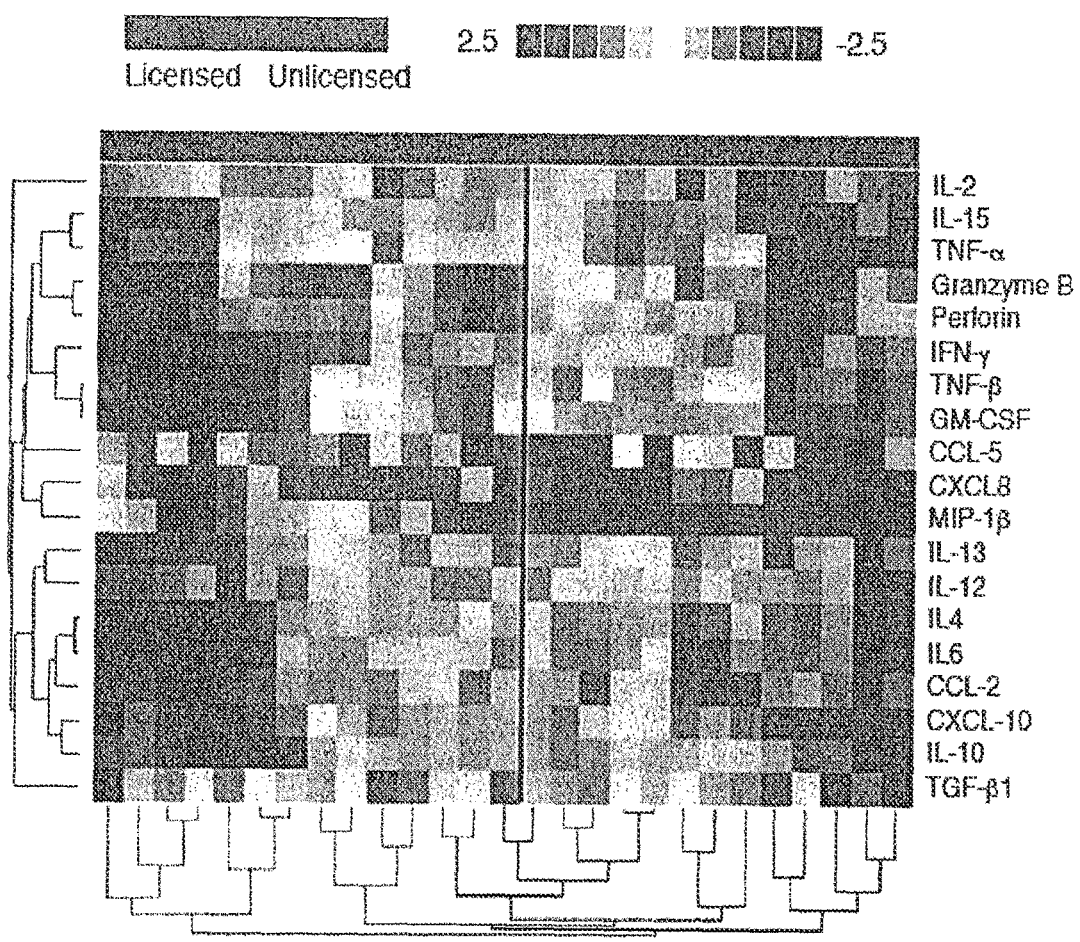
FIG. 19 depicts the heatmap analysis of MS cohort licensed and unlicensed NK cell secretion profiles. Clustering of normalized licensed and unlicensed NK cell three-day culture in 2 ng ml$^{-1}$ IL-2 supernatant secretion profiles. Horizontal color bars on top of the heatmap represents licensed (red bar) and unlicensed (blue bar) patients. Each row represents on cytokine, each column represents one patient. n=8 to 19.
Figure 20:
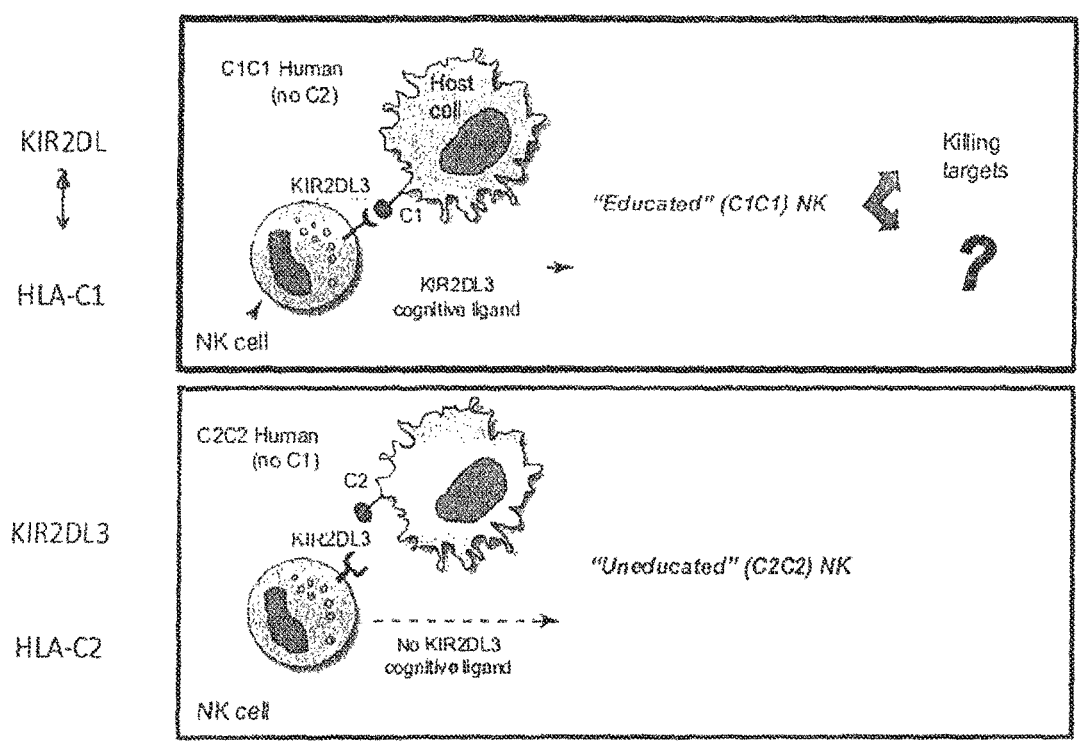
FIG. 20 is a schematic of how NK cell licensing (i.e., "education") depends on the interaction of KIR and HLA I ligands.

Clinical samples used in the experiments presented herein were collected according to protocols approved by the institutional review committee of Cedars Sinai Medical Center (CSMC) and of UCLA. CD patient, previously genotyped for HLA and KIR (J. A. Hollenbach et al., Susceptibility to Crohn's disease is mediated by KIR2DL2/KIR2DL3 heterozygosity and the HLA-C ligand. *Immunogenetics* 61, 663 (Sep. 30, 2009)), were consented and called back by CSMC. 455 out of 1306 CD patients are AA haplotype, 28 were consented for call-back blood donation, and 20 samples were collected. Healthy donors were recruited at UCLA Clinical & Translational Research Laboratory, and genotyped by the UCLA Immunogenetics Center. The multiple sclerosis (MS) cohort of 50 frozen PBMC samples were provided by Immune Tolerance Network (ITN), and KIR and HLA typing were performed by Children's Hospital Oakland Research Institute (CHORI). A complete clinical sample process and assay pipeline is provided (FIG. 14).

Cell Isolation.

PBMCs were isolated by Ficoll-Plaque (GE Healthcare, Chalfont St Giles, England) density gradient centrifugation. Human NK cells were purified either from whole blood using the RosetteSep Human NK cell enrichment Cocktail, or from PBMC using Human NK cell negative selection kit (StemCell Technologies, Vancouver, BC, Canada). Human Treg depleted T cells were purified from PBMC using Human T cell enrichment kit and CD25 positive selection kit, total CD4 T cells were purified from PBMC using Human T cell enrichment kit and CD4 positive selection kit (StemCell Technologies, Vancouver, BC, Canada). The purity of isolated NK cells and T cells were checked to be above 90%.

NK-T Cell Co-Culture and Blocking Assays.

Before co-culture, round bottom 96-well plates were coated with anti-CD3/CD28 antibody (R&D Systems, Minneapolis, Minn.) in PBS at 1.5 ug ml$^{-1}$ at room temperature for 2 hours, or at 0.5 ug ml$^{-1}$ at 4° C. overnight. T cells were stained with 0.2 uM CFSE (Invitrogen, Carlsbad, Calif.), and co-cultured with NT (cells for 3 days in 96-well plates at 1×10$^6$ cells ml$^{-1}$ in presence of 2 ng ml$^{-1}$(26 I.U) IL-2 with complete RPMI 1640 medium (recipe provided above). Blocking antibodies for OX40 ligand and 2B4 (CD 252 and CD244, R&D Systems, Minneapolis, Minn.) were added to the co-culture at concentration of 10 ug ml$^{-1}$. Neutralizing antibodies, for IL-6, IFN-γ, TNF-α, and isotype control mouse IgG1k (ebioscience, San Diego, Calif.), and their combinations were added to the co-culture at 1.25 ug ml$^{-1}$. The recombinant cytokines IL-6, IFN-y, and TNF-α (R&D Systems, Minneapolis, Minn.) was each added to a final concentration of 20 ng ml$^{-1}$, comparable to the concentration measured for these cytokines in NT (cell three-day culture media analyzed by multiplex ELISA chip. For transwell assay, 24-well plates were used; NT (cells were placed on the filter side of a 1.0 um pore-sized transwell (BD Falcon, San Jose, Calif.), and CFSE-stained T cells were placed on the plate side of the transwell.

TH17 Differentiation Assay.

Before culturing, round bottom 96-well plates were coated with 1 ug ml$^{-1}$ anti-CD3 (R&D Systems, Minneapolis, Minn.) in PBS for 2 hours at room temperature, and washed with 5% human AB Serum RPMI media (Lonza, Rockland, Me.). Total CD4$^+$ T cells were purified and stimulated with 0.2 ug ml$^{-1}$ soluble anti-CD28, primed with different percentages of NT (supernatants, and in the presence or absence of various cytokine combinations. At Day 6 or 7, CD4$^+$ T cells were re-suspended, washed once with media, and expanded with 2 ng ml$^{-1}$(26 I.U) IL-2 plus the same conditions provided for priming. At Day 14, the cells were stimulated with PMA/Ionomycin and Brefeldin A at 1 uL per well for 5 hours. Cells were then surface stained with anti-CD3, intracellularly stained with anti-IFN-y, anti-IL-22, and anti-IL-17A, followed by flow using LSRII (BD Biosciences, San Jose, Calif.).

Multiplex Cytokine ELISA Assay.

Figure 2:
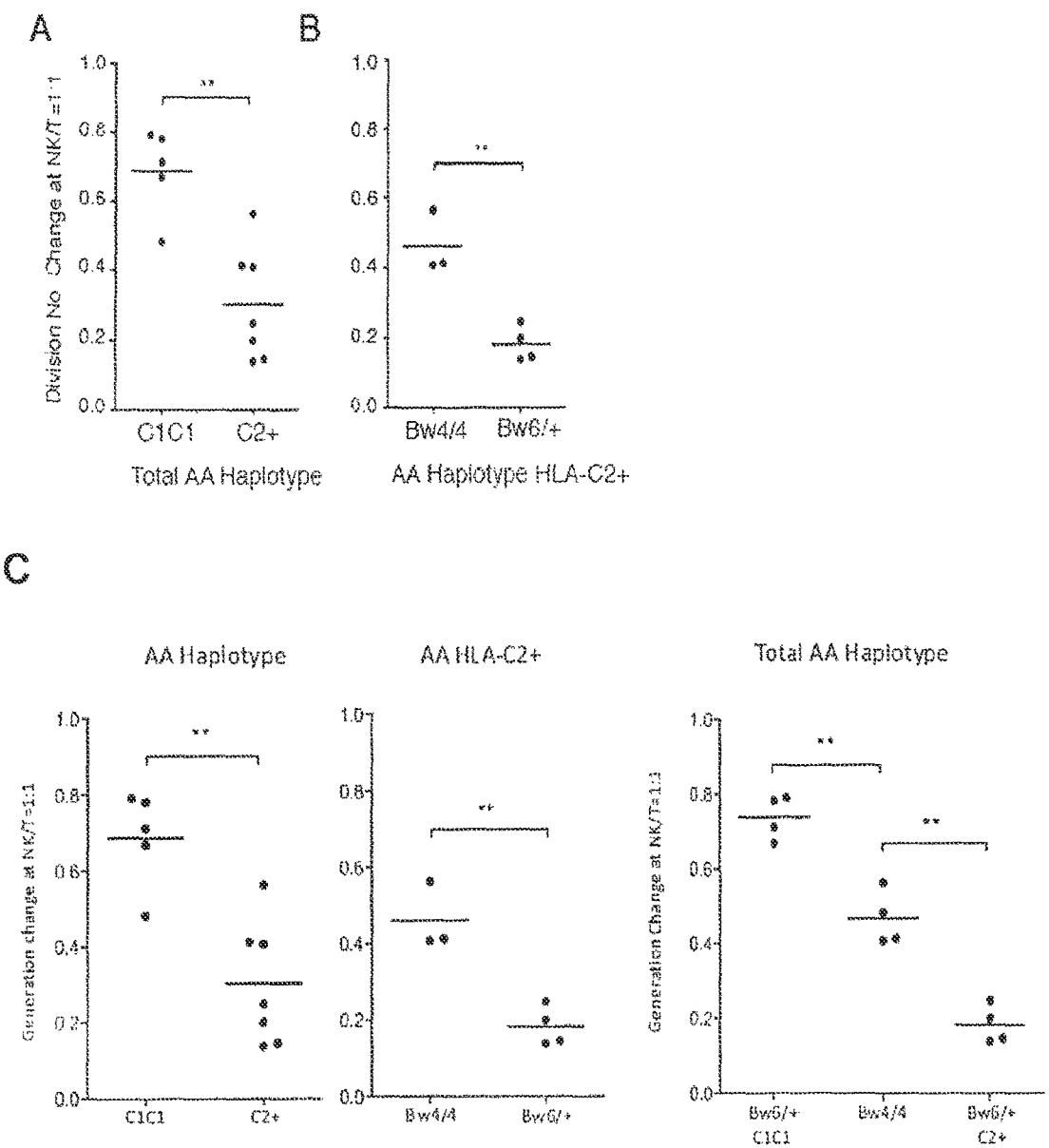
FIG. 2 depicts NK cells from genetically licensed patients have distinct cytokine secretion patterns compared to those from unlicensed patients in bulk culture. (A) Univariate comparison of cytokine production level of bulk culture NK cells from C1C1 (Licensed, solid dot) and C2$^+$ (Unlicensed, open Square) CD patients. The vertical axis shows the fluorescence intensity. (n=4 to 5, P values are calculated using two tailed student t test, adjusted for multiple comparison by FDR, *p<0.05; p<0.005; *p<0.0005). The dash-line indicates the detection threshold. Secretion profiles were measured by multiplex ELISA. (B) Hierarchical clustering of the bulk cytokine production profile of NK cells from C1C1 (red) and C2$^+$ (blue) CD patients. Each row represents one protein indicated on the right, and each column represents one patient. (n=4 to 5). (C) Univariate comparison of cytokine production from licensed (all C1C1 and all Bw4/Bw4, red solid dot) and unlicensed (all other genotype, open square) MS patients. (n=8 to 19, P values are calculated using two tailed student t test, adjusted for multiple comparison by FDR, *p<0.05; **p<0.005). The dash line shows the detection threshold.

CD and MS frozen PBMCs were thawed and recovered overnight, and NK cells were isolated using Human NK cell negative selection kit (StemCell Technologies, Vancouver, BC, Canada). NK cells were cultured for 3 days in round-bottom 96-well plate at 1×10$^6$ cells ml$^{-1}$ in 2 ng ml$^{-1}$ (26 I.U) IL-2 with complete RPMI 1640 medium, containing 10% Fetal Bovine Serum (FBS), 100 I.U ml$^{-1}$ penicillin 100 ug ml$^{-1}$ streptomycin, 10 mM HEPES buffer, 2 mM glutamine (Cellgro, Manassas, Va.), and 5×10$^{-5}$ M 2-mercaptoethanol (Sigma, St. Louis, Mo.). Then CD media samples were collected, stored at −80° C. Before analysis, samples were thawed, concentrated 4 times, and assayed as one batch. The initial protein panel was chosen to incorporate immune function markers, consisting primarily of cytokines and chemokines that could be secreted by NK cells. The final NK secretion antibody panel was chosen to incorporate non-redundant secretions detectable at NK three-day culture. (FIG. 2)

Single Cell Multiplex Cytokine Analysis.

Frozen aliquots of PBMC were thawed and recovered overnight. Bulk NK cells were purified using human NK cell enrichment kit; CD3$^-$ CD56$^{dim}$KIR2DL3$^+$ KIR3DL1$^-$ KIR2DL1$^-$ and CD3$^-$CD56$^{dim}$KIR2DL3$^-$ NK subsets sorted by FACS. All cells were prepared on ice, and immediately analyzed by a single cell microchip. Briefly, the microchip proteomics platform is based upon isolating individual or a small number of cells into thousands of ~600 picoliter volume microchambers, with each chamber equipped with a miniaturized antibody array. The chips used here permitted the simultaneous measurement of 19 protein markers in each microchamber (Table 1). After loading onto the SCBC, the cells were stimulated with 5 ng ml$^{-1}$ PMA and 500 ng ml$^{-1}$ Ionomycin for 12 hours at 37° C., and the microchip was imaged to count cell numbers within each microchambers. After cells were washed off, the fluorescence readouts were generated by an ELISA immunoassay and were quantified using a GenePix 4400A array scanner and custom-built software algorithms.

TABLE 1

Media protein biomarker and single cell function cytokine panel

| Antibody | Manufacturer | Initial biomarker panel | Finalized biomarker panel | Single cell panel |
|---|---|---|---|---|
| IFN-y | R&D | + | + | + |
| TNFα | eBioscience | + | + | + |
| Granzyme B | R&D | + | + | + |
| Perforin | Abcam | + | + | + |
| TNF13 | R&D | + | + | + |
| TGF131 | R&D | + | + | + |
| IL-2 | R&D | + | + | + |
| IL-4 | eBioscience | + | + | + |
| IL-6 | R&D | + | + | + |
| IL-10 | R&D | + | + | + |
| IL-12 | R&D | + | + | + |
| IL-13 | R&D | + | + | + |
| IL-15 | R&D | + | + | + |
| CCL5 | R&D | + | + | + |
| GMCSF | eBioscience | + | + | + |
| MIP-113 | R&D | + | + | + |
| CCL2 | R&D | + | + | + |
| CXCL8 | R&D | + | + | + |
| CXCL10 | R&D | + | + | + |
| IL113 | eBioscience | + | − | − |
| IL-5 | R&D | + | − | − |
| IL7 | R&D | + | − | − |
| IL-17A | eBioscience | + | − | − |
| IL-17E | R&D | + | − | − |
| IL-17F | R&D | + | − | − |
| IL-22 | R&D | + | − | − |
| TGF-132 | R&D | + | − | − |
| CCL-11 | R&D | + | − | − |
| CXC-L3 | R&D | + | − | − |
| CCL-21 | R&D | + | − | − |
| MIP1α | R&D | + | − | − |

The single cell barcode chip can address 19 cytokine analytes. Among the 31 cytokine initially assessed for NK production, 24 were detected above threshold, although the detectable number of cytokines was lower in any single individual. To select the cytokines for the final panel: (a) we excluded MIP-1alpha (its production was highly concordant with MIP-1beta; (b) we included IL-2 and IL-1β, which were readily detectable in many individuals and of substantial IBD immunologic interest; and, (c) we excluded several because they were infrequently above detection (IL-1b, IL-5, IL-7, IL-17 (A, E, F), IL-22, CCL-11, CCL-21, CXCL-1, TGFβ2).

Antibodies.

The following antibodies and cell tracer were used staining for flow analysis: FITC-conjugated anti-CD158b (BD Biosciences, San Jose, Calif.), anti-IFN-y (ebioscience, San Diego, Calif.); CFSE; PE-conjugated anti-IFN-y (BD Biosciences, San Jose, Calif.), anti-TNF-α, anti-IL-22, anti-Granzyme B (ebioscience, San Diego, Calif.), anti-GM-CSF (R&D Systems, Minneapolis, Minn.); PerCP-conjugated anti-CD3 (BD Biosciences, San Jose, Calif.); APC-conjugated anti-CD158a (Miltenyi Biotec, Bergisch Gladbach, Germany), anti-CD4 (BD Biosciences, San Jose, Calif.), anti-IL-17A (ebioscience, San Diego, Calif.); strepavidin-PerCP; PE-Cy7-conjugated anti-CD56, anti-CD14 (BD Biosciences, San Jose, Calif.), Vioblue-conjugated anti-3DL1 (Miltenyi Biotec, Bergisch Gladbach, Germany), eFluor 650NC-conjugated anti-CD3 (ebioscience, San Diego, Calif.). anti-mouse IgG K/Negative Control Compensation Particles. The use of antibody for staining was performed as per the manufacturer's instructions with proper titrations. Antibodies used for cytokine assays are IL-2, IL-6, IL-10, IL-15, IL-1β, CCL-4 (MIP-113), CCL-5, CXCL-10, CCL-2, CXCL-8, IFN-y, TNF-α, TNF-β, granzyme B, TGF-β1 (R&D Systems, Minneapolis, Minn.), IL-4, IL-12, GM-CSF, perforin (eBiosciences, San Diego, Calif.).

Flow Cytometry and Cell Sorting.

Phenotypic analysis of PBMC was performed using flow cytometry after staining of cells with fluorescence dye-conjugated antibodies. Labeled cells were analyzed with a FACSCalibur flow cytometer using CellQuest software, or LSR II (BD Biosciences, San Jose, Calif.) using FACSDiva software (BD Biosciences, San Jose, Calif.) at UCLA Flow Cytometry Core, and data analysis was performed using FlowJo (Tree Star Inc., Ashland, Oreg.) Cells were sorted for $CD3^-CD56^{dim}KIR2DL3^+$ $KIR3DL1^-$ $KIR2DL1^-$ and $CD3^-CD56^{dim}$ $KIR2DL3^-$, using Aria I equipped with FACSDiva software (BD Biosciences, San Jose, Calif.).

Statistical Analysis and Data Access.

Student's two-tailed unpaired t test was used; P values of less than 0.05 were regarded as significant. Association analyses were performed using contingency table testing and a standard chi-square measure. All cytokine data were normalized before biostatistical analysis. GraphPad Prism (San Diego, Calif.) was used for statistical analysis and graphing. Principal Component Analysis (PCA), Hierarchical Clustering (HC), box-plot and scatter-plot analysis were performed in R package using custom-written codes. Microchip data from this study is available at the Heath Group lab webpage on CalTech's website.

EXAMPLES

Example 1: Coexistence of KIR2DL3 and HLA-C1 Genes Predisposes AA Patients for Susceptibility to Crohn's Disease Mechanistic studies of human NK licensing are challenging due to the complex composition of KIR-HLA combinations (5), and the conflicting roles inhibitory and activating KIRs play in licensing. Therefore, individuals homozygous for the KIR A haplotype (Table 2), a common genotype (~30% worldwide) which contains inhibitory KIRs for three key HLA class I ligands (HLA-C1, HLA-C2 and HLA-Bw4) but only one single activating KIR were studied (Z. Du, D. W. Gjertson, E. F. Reed, R. Rajalingam, Receptor-ligand analyses define minimal killer cell Ig-like receptor (KIR) in humans. *Immunogenetics* 59, 1 (January, 2007); J. A. Hollenbach, I. Nocedal, M. B. Ladner, R. M. Single, E. A. Trachtenberg, Killer cell immunoglobulin-like receptor (KIR) gene content variation in the HGDP-CEPH populations. *Immunogenetics* 64, 719 (October, 2012)).

TABLE 2

Healthy Donor and Crohn's Patient Demographics

| | | Total | Healthy | Crohn's Patients |
|---|---|---|---|---|
| Total healthy donors | | 30 | 10 | 20 |
| Gender | Female | 18 | 6 | 12 |
| | Male | 12 | 4 | 8 |
| Age (average ± SD) | | 39 ± 9.8 | 30 ± 9.1 | 49.5 ± 9.3 |
| KIR genotype | Non AA | 7 | 7 | 0 |
| | AA | 23 | 4 | 20 |
| HLA-C | C1C1 | 13 | 3 | 10 |
| | C1C2 | 7 | 1 | 6 |
| | C2C2 | 4 | 0 | 4 |
| HLA-Bw | Bw6/6 | 9 | 3 | 6 |
| | Bw4/6 | 9 | 0 | 9 |
| | Bw4/4 | 5 | 0 | 5 |

Specifically, Table 2 describes the AA genotypes of the patients in this study. Carriers of two A haplotypes contain a fixed number of nine KIR genes (3DL3-2DL3-2DP1-2DL1-3DP1-2DL4-3DL1-2DS4-3DL2). Carriers of non-AA genotype comprise carriers of A and B halotypes or carriers of two B haplotypes, which contains one or more B haplotype-specific genes (2DL2, 2DL5, 2DS1, 2DS2, 2DS3, 2DS5 and 3DS1).

Different inhibitory KIR-HLA class I ligand pairs confer various levels of strength for NK licensing (Table 3) (M. Yawata et al., MHC class I-specific inhibitory receptors and their ligands structure diverse human NK-cell repertoires toward a balance of missing self-response. *Blood* 112, 2369 (Sep. 15, 2008)). The most potent pair is KIR2DL3/HLA-C1, and the second strongest pair is KIR3DL1/HLA-Bw4. Accordingly, it is hypothesized that strong NK licensing confers a trait that enables NK cells to induce CD pathogenesis.

TABLE 3

Hierarchy in the strength of NK cell education (adapted from J. H. Cho, P. K. Gregersen, Genomics and the multifactorial nature of human autoimmune disease. *N Engl J Med* 365, 1612 (Oct. 27, 2011))

| KIR | HLA | Level of Response |
|---|---|---|
| 2DL3 | Cw*07 (C1) | ++++ |
| $3DL1^{High}$ | $Bw4^{Strong}$ | ++++ |
| 2DL3 | Cw*12 | +++ |
| 2DL3 | C1 + B*46 | +++ |
| 2DL1 non*004 | Cw2*02,4,5,6,15 (C2) | ++ |
| 3DL1*007 | $Bw4^{Strong}$ | ++ |
| NKG2A | HLA-E | ++ |
| 2DL1*004 | Cw2*02,4,5,6,15 (C2) | + |
| 2DL3 | Cw*01,3,8 (C1), 1404 | + |
| $3DL1^{High}$ | B*27 | + |
| $3DL1^{High}$ | A*24 | + |
| 2DL1 | Cw*01,3,8, (C1), 1404 | − |
| 2DL3 | Cw*1402 | − |
| 2DL3 | Cw2*02,4,5,6,15 (C2) | − |
| $3DL1^{High}$ | B*13 | − |
| $3DL1^{High}$ | B*37 | − |
| 3DS1 | $Bw4^{Strong}$ | − |
| 3DL2 | A*3,11 | − |

To determine if KIR2DL3/HLA-C1 is genetically associated with increased susceptibility to CD in AA haplotype individuals, the distribution of C1/C2 and Bw4/Bw6 allotypes in an AA haplotype subpopulation of our CD cohort was analyzed (J. A. Hollenbach et al., Susceptibility to Crohn's disease is mediated by KIR2DL2/KIR2DL3 heterozygosity and the HLA-C ligand. *Immunogenetics* 61, 663 (Sep. 30, 2009)).

Among the 455 KIR haplotype AA CD patients studied, the distribution of C1C1, C1C2, and C2C2 in Bw6/Bw6 was significantly disproportionate to that in Bw4/Bw6 and Bw4/Bw4 patients (Chi square test: 'K'K'K p<0.0005 in Table 4). Hence, there was an enrichment of C1C1 in Bw6/Bw6; and vice versa, Bw6/Bw6 was enriched in C1C1. This analysis indicated that the C1C1 Bw6/Bw6 genotype predicted genetic predisposition to CD in AA haplotype individuals.

TABLE 4

HLA allotype distribution and $Chi^2$ test of AA haplotype CD Patients
(Values are % of patients or (absolute number of patients)

| % (No.) | C1C1 | C1C2 | C2C2 | $Chi^2$ Test |
|---|---|---|---|---|
| Bw6/6 | 15.8 (72) | 11.9 (54) | 3.7 (17) | *** P < 0.0005 |
| Bw4/6 | 12.7 (58) | 27.7 (126) | 11.4 (52) | |
| Bw4/4 | 4.0 (18) | 8.4 (38) | 4.4 (20) | |

Example 2: Licensed NK Cells Strongly Promote the Proliferation of Autologous CD4$^+$ T Cells Pro-inflammatory CD4$^+$ helper T cells are the main effectors in induction and perpetuation of intestinal inflammation (M. F. Neurath, S. Finotto, L. H. Glimcher, The role of Th1/Th2 polarization in mucosal immunity. *Nat Med* 8, 567 (June, 2002); G. Bouma, W. Strober, The immunological and genetic basis of inflammatory bowel disease. *Nat Rev Immunol* 3, 521 (July, 2003)). As a major cellular component of innate immunity, NK cells demonstrably cross-talk with the adaptive immunity arm (J. A. Hollenbach, I. Nocedal, M. B. Ladner, R. M. Single, E. A. Trachtenberg, Killer cell immunoglobulin-like receptor (KIR) gene content variation in the HGDP-CEPH populations. *Immunogenetics* 64, 719 (October, 2012); S. Kim et al., HLA alleles determine differences in human natural killer cell responsiveness and potency. *Proc Natl Acad Sci USA* 105, 3053 (Feb. 26, 2008); F. D. Shi, L. Van Kaer, Reciprocal regulation between natural killer cells and autoreactive T cells. *Nat Rev Immunol* 6, 751 (October, 2006); E. Narni-Mancinelli et al., Tuning of natural killer cell reactivity by NKp46 and Helios calibrates T cell responses. *Science* 335, 344 (Jan. 20, 2012); E. Vivier, E. Tomasello, M. Baratin, T. Walzer, S. Ugolini, Functions of natural killer cells. *Nat Immunol* 9, 503 (May, 2008)).

Since NK cells can stimulate or inhibit T cell activation via multiple mechanisms (A. Martin-Fontecha et al., Induced recruitment of NK cells to lymph nodes provides IFN-gamma for T(H)1 priming. *Nat Immunol* 5, 1260 (December, 2004); E. Assarsson et al., NK cells stimulate proliferation of T and NK cells through 2B4/CD48 interactions. *J Immunol* 173, 174 (Jul. 1, 2004); A. Zingoni et al., Cross-talk between activated human NK cells and CD4+ T cells via OX40-OX40 ligand interactions. *J Immunol* 173, 3716 (Sep. 15, 2004); J. Hanna et al., Novel APC-like properties of human NK cells directly regulate T cell activation. *J Clin Invest* 114, 1612 (December, 2004)), this experiment was designed to determine if strongly and weakly licensed NK cells from CD patients could differentially modulate T cell proliferation in in vitro co-cultures.

Peripheral blood NK cells and autologous T cells were isolated from CD patients and co-cultured in the presence of immobilized anti-CD3/CD28 and IL-2 at 2 ng mL$^{-1}$ (26 I.U.). At day 3, CD4$^+$ cell proliferation was measured via CFSE dilution. It was determined that CD4$^+$ cell proliferation was augmented in a linearly with the number of licensed NK cells present (FIG. 1A, B, $R^2$=0.996, when proliferation is measured by the increase in the average division number at each NK:T ratio compared to that of T cell alone). This indicated that licensed NK cells augmented CD4$^+$ cell proliferation in a dose-dependent manner.

Using linearity ($R^2$>0.85) as a quality control criterion, 12 patient assays were selected for genetic correlation analysis. At a NK:T ratio of 1:1, C1C1 NK cells were significantly more potent than C2$^+$ NK cells in all AA haplotype patients, and Bw4/Bw4 NK cells were significantly more potent than Bw6$^+$ NK cells within the C2$^+$ subset of patients (FIG. 2). Thus, three distinct levels of NK function were observed: C1C1 Bw6$^+$>Bw4/Bw4>Bw6/$^+$ C2$^+$ (FIG. 1C), and this order conforms to KIR licensing strength (Table 2) (M. Yawata et al., MHC class I-specific inhibitory receptors and their ligands structure diverse human NK-cell repertoires toward a balance of missing self-response. *Blood* 112, 2369 (Sep. 15, 2008)).

To assess the mechanism of CD4+ T cell proliferation augmentation, we considered that NK cell interaction might involve their expression of co-stimulatory molecules, such as 2B4 and OX40 ligand (E. Assarsson et al., NK cells stimulate proliferation of T and NK cells through 2B4/CD48 interactions. *J Immunol* 173, 174 (Jul. 1, 2004); A. Zingoni et al., Cross-talk between activated human NK cells and CD4+ T cells via OX40-OX40 ligand interactions. *J Immunol* 173, 3716 (Sep. 15, 2004); J. Hanna et al., Novel APC-like properties of human NK cells directly regulate T cell activation. *J Clin Invest* 114, 1612 (December, 2004)). However, augmentation was preserved when these surface molecules were blocked with neutralizing antibodies (FIG. 1D), indicating that the NK augmentation of CD4$^+$ cell proliferation does not depend on the expression of 2B4 and OX40. To determine if the NK effect was contact-dependent at all, we separated NK cells from T cells using 1.0 μm pore transwells, which allows cellular communication only through soluble factors. To our surprise, augmentation was fully preserved (FIG. 1E). These results strongly suggested that the NK augmentation of CD4$^+$ cell proliferation was mainly mediated by soluble molecules secreted by licensed NK cells.

Example 3: Licensed NK Cells are Polyfunctional in Pro-Inflammatory Cytokine Production at the Single-Cell Level This experiment was designed to determine whether KIR licensing results in a mosaic of NK cells devoted to individual cytokines, or conversely, single cells expressing a polyfunctional cytokine program. To assess the cytokine secretion profile of individual NK cells, single cell barcode chips (SCBCs) were used on a high-throughput microfluidics platform (C. Ma et al., A clinical microchip for evaluation of single immune cells reveals high functional heterogeneity in phenotypically similar T cells. *Nat Med* 17, 738 (June, 2011)).

With SCBCs, single cells or a small number of cells were separated into thousands of microchambers on chip, where the production of 19 cytokines was simultaneously and independently measured during a 12-hour period. This technology has previously been extensively validated, and its utility in studying immune cell response has been demonstrated (C. Ma et al., A clinical microchip for evaluation of single immune cells reveals high functional heterogeneity in phenotypically similar T cells. Nat Med 17, 738 (June, 2011)).

Figure 3:
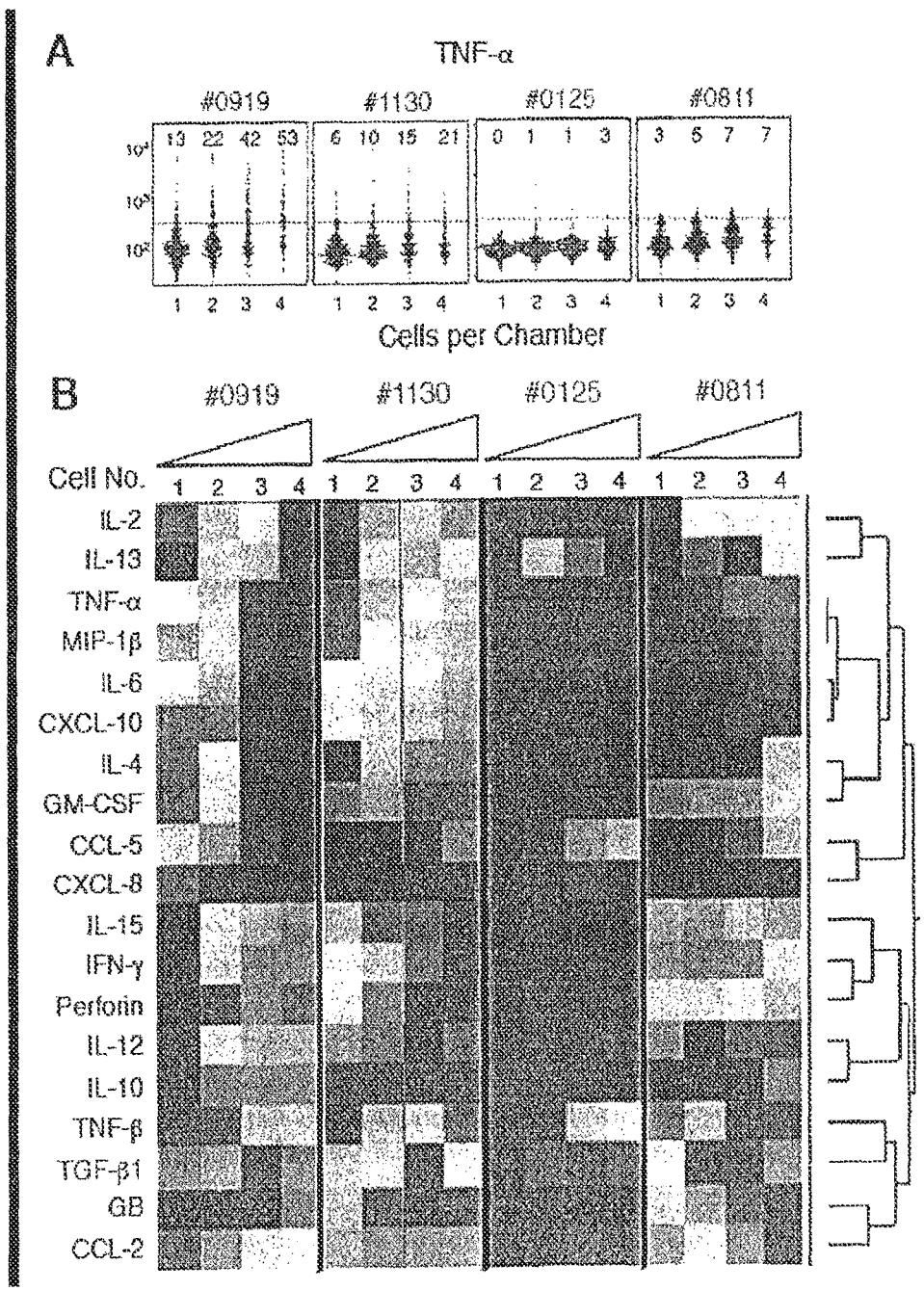
FIG. 3 depicts NK cells from genetically licensed CD patients produce multiple cytokines at high amounts compared to those from unlicensed CD patients at a single cell level. (A) Univariate comparison of TNF-α production of NK cells from licensed (#0919, #1130, red) and unlicensed (#0125, #811, blue) CD patients. The number in each graph indicates the percentage of microchambers with different number of cells that are positive for TNF-α signals. (B) Heatmap of cytokine secretion capacity for all cytokines and all patients analyzed. Each row represents one cytokine, and each column represents the percentage of microchambers containing different number of NK cells from each patient that have positive cytokine signals. The color scale shows the difference in standard deviation. (C) PCA single NK cell measurements from the four CD patients. Percentage of variation explained by each component is shown in parentheses for each axis. The composition for each component is indicated on the left of the plot. (D) Bar graph of NK cell polyfunctionality. The percentage of single NK cells producing 1, 2, 3, 4, 5, and >5 cytokines for the four patients studied is showed by a different color.
Figure 3:
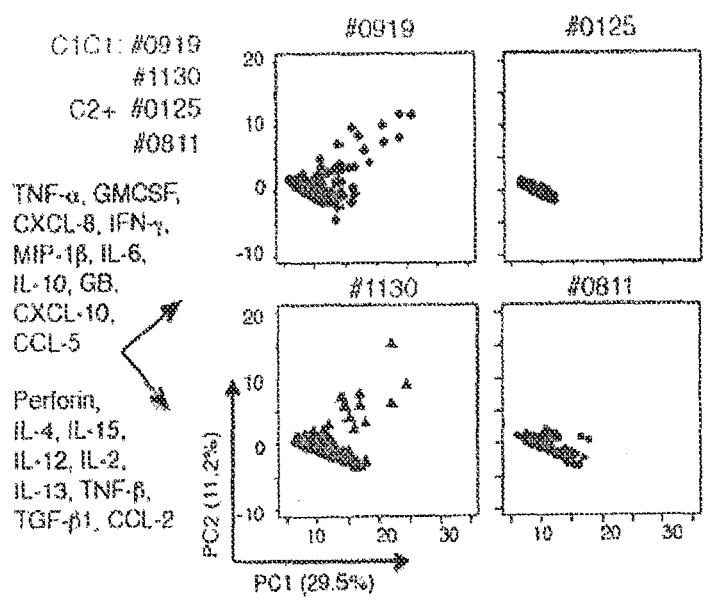
Figure 3:
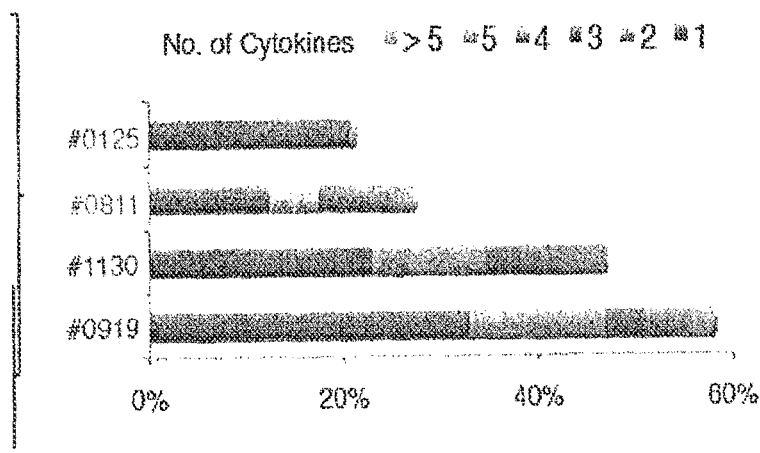
Figure 4:
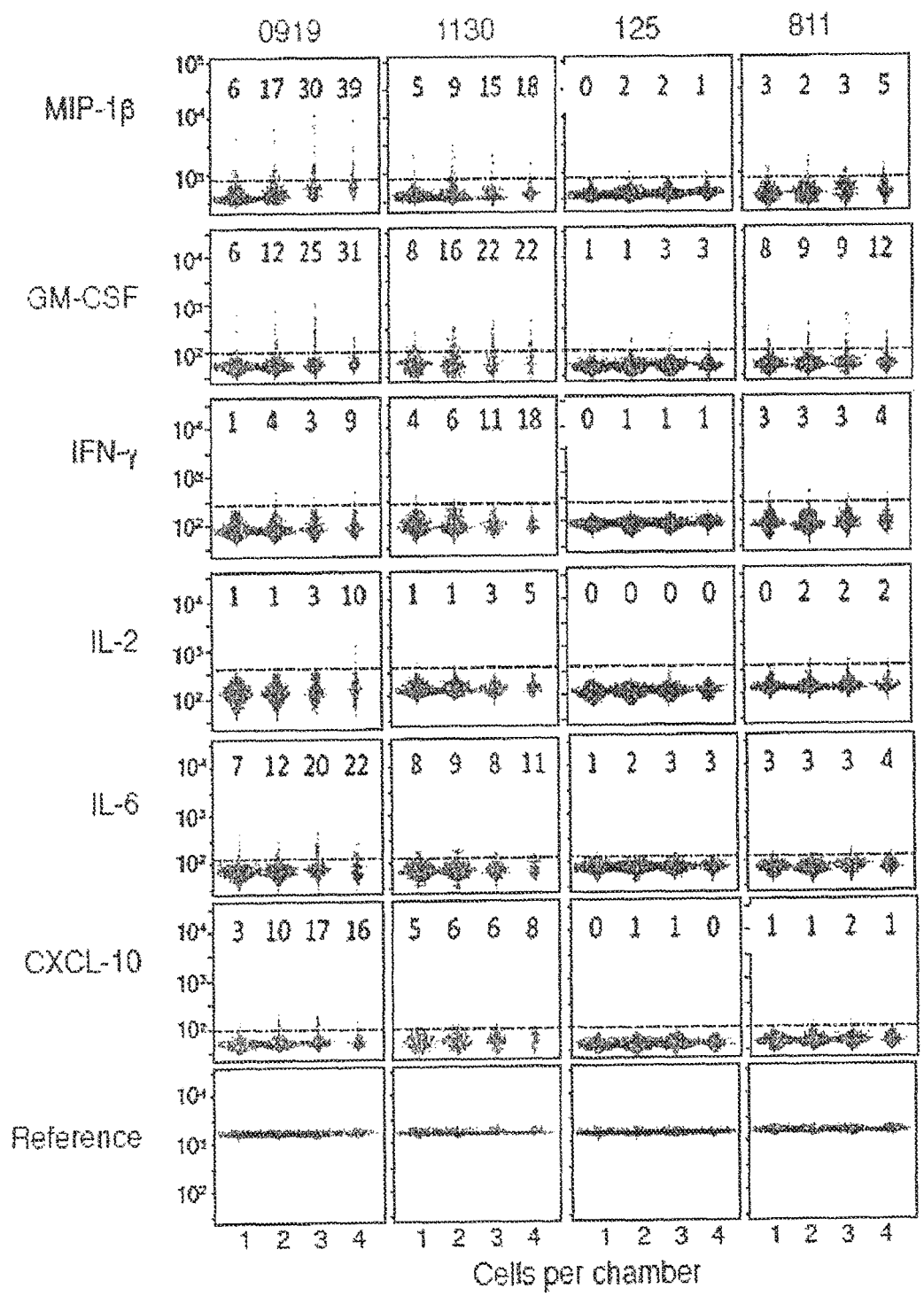
FIG. 4 depicts the univariate comparison of secretions between C1C1 and C2+CD patient NK cells using SCBC. MIP-1β, GM-CSF, IFN-γ, IL-2, IL-6, CXCL-10, and reference signals from 1-4 cell SCBC microchambers from C1C1 (#0919, #1130, red) and C2 (#0125, #811, blue) CD patients.
Figure 5:
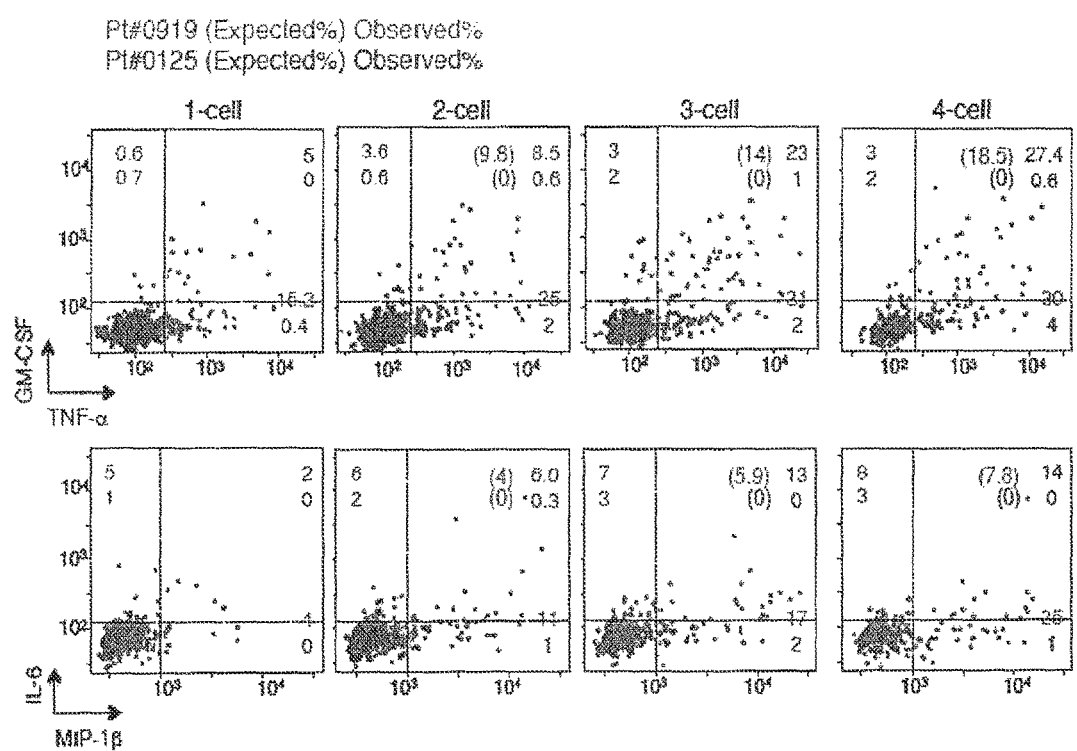
FIG. 5 depicts a comparison of secretion profiles between C1C1 and C2$^+$ CD patient NK cells. 2-D scatter plot of cytokine signals of licensed (#0919, red) and unlicensed (#0125, blue) patient NK cells from SCBC 1-4 cell microchamber. Numbers in each quadrant indicated the percentage of signals in that quadrant. Numbers in parentheses indicated the expected frequencies of signals if cells were acting independently, calculated from 1-cell signals.

Single NK cell cytokine secretion between 2 C1/C1 Bw6/Bw6 and 2 C2$^+$ Bw4$^+$ CD patients was compared. When SCBC microchambers containing 1 to 4 cells was analyzed, licensed NK cells exhibited a higher output of multiple cytokines, including TNF-α, MIP-113, GM-CSF, IFN-y, IL-2, IL-6, and CXCL-10 (see scatterplots and heatmap, FIG. 3A, FIG. 3B, and FIG. 4). PCA analysis of the single cell data from four CD patients with a licensing genotype showed that their NK cells contained a subset that produced effector proteins (CCL-5, TNF-α, IFN-y, MIP-113, and IL-6), which in contrast were barely detected in NK cells from patients without a licensing genotype (FIG. 3C). When the co-expression of certain highly expressed cytokines, namely TNF-β and GM-CSF, or IL-6 and MIP-113 was analyzed, the prevalence of double-positive signals in multi-cell chambers was higher than the expected frequencies if the cells were acting independently (FIG. 5). This suggests functional cross-talk between co-cultured NK cells, and deserves further study.

The composition of cells producing 1, 2, 3, 4, 5, and >5 cytokines were characterized and it was observed that a higher fraction (50-60% vs. 20-30%) of strongly licensed NK cells produced at least one cytokine, half of which secreted 2 or more cytokines (FIG. 3D), supporting a polyfunctional phenotype of licensed NK cells. These findings combined demonstrated that licensed CD patient NK cells were reprogrammed for enhanced production of cytokines contributing to a chronic inflammatory state in vivo.

Example 4: The NK Cell Subset Expressing Licensing KIRs Contributes to the Polyfunctional Cytokine Production of a Licensed Individual Within each individual, KIRs are stochastically expressed by NK cells, which result in a composite of licensed and unlicensed NK cells (N. M. Valiante et al., Functionally and structurally distinct NK cell receptor repertoires in the peripheral blood of two human donors. Immunity 7, 739 (December, 1997)). For example, in an AA haplotype healthy subject (who bears both KIR2DL3 and KIR3DL1 genes), the NK population includes cells that are single-positive, double-positive, or double-negative for these receptors. Accordingly, when such a subject is HLA-C1C1 (C1, ligand for KIR2DL3) and HLA-Bw6/Bw6 (Bw6, non-ligand for KIR3DL1), the KIR2DL3$^+$ NK cells are licensed, and the KIR2DL3$^-$NK cells are unlicensed.

Accordingly, this experiment was designed to determine if the licensing-associated polyfunctional cytokine production is a selective feature of the NK cell subset expressing licensing KIRs. Licensed subsets (CD3$^-$CD56$^{dim}$KIR2DL3$^-$KIR3DL1$^-$KIR2DL1$^-$) and unlicensed (CD3$^-$CD56$^{dim}$KIR2DL3$^-$) were sorted, achieving a high purity after sorting acquisition (>95%). These subpopulations were then evaluated for their single cell cytokine production capacity (C. Ma et al., A clinical microchip for evaluation of single immune cells reveals high functional heterogeneity in phenotypically similar T cells. Nat Med 17, 738 (June, 2011)).

77% of the KIR2DL3$^+$NK cells co-expressed a large amount of CCL-5 and MIP-113 upon stimulation, whereas virtually no (1%) KIR2DL3$^-$NK cells co-expressed these proteins. MIP-113$^+$KIR2DL3$^+$ NK cells also co-expressed IFN-y, with a considerable fraction being IFN-y/TNF-α double-producers, whereas KIR2DL3$^-$ NK cells were low for MIP-113 and silent for IFN-y and TNF-α. Interestingly, more than 50% of MIP-113$^+$ KIR2DL3$^-$ NK cells co-expressed TGF-β1, a regulatory cytokine rarely produced by MIP-113$^+$ KIR2DL3$^+$ NK cells (FIG. 6A).

In KIR2DL3$^-$ NK cells, 65% were silent for all cytokines; 22% expressed one cytokine, and only 13% secreted 2 or more cytokines. In sharp contrast, 99% of KIR2DL3$^+$ NK cells secreted at least one cytokine. Among them, 15% expressed one (CCL-5 or MIP-113); one third expressed two cytokines (typically CCL-5MIP-113$^+$), and another one third expressed three cytokines (mostly IFN-y$^+$MIP-113$^+$CCL-5$^+$); and, a substantial fraction (10%) produced four cytokines Due to the high purity of the sorted subpopulations, these findings could not be attributed to an artifact of contaminating cells, but instead reflect the intrinsic functional scope and heterogeneity within each of these NK cell subpopulations.

Figure 6:
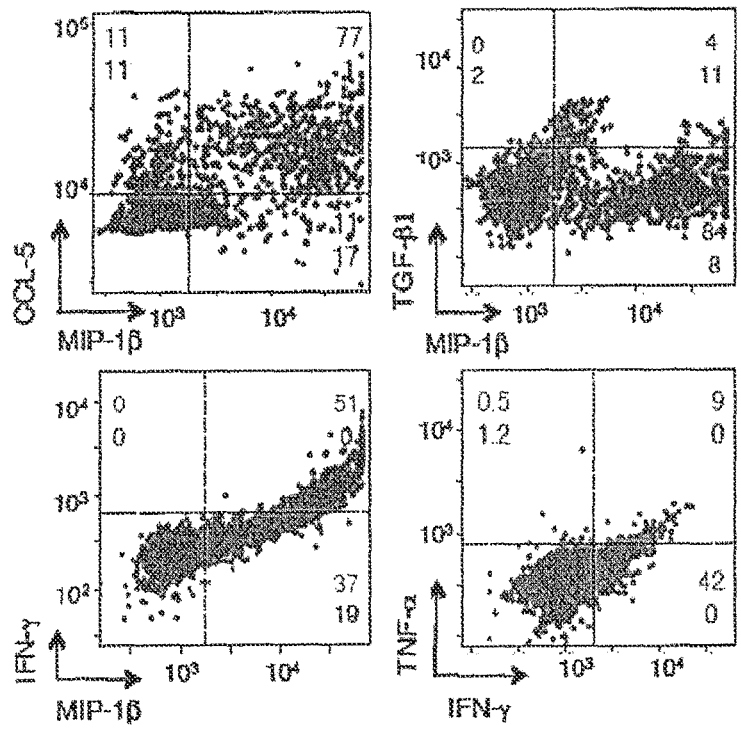
FIG. 6 depicts the licensed and unlicensed NK cell subsets have differentially polarized cytokine capacity within one patient. An AA healthy donor NK cells were sorted for KIR2DL3$^+$KIR3DL1$^-$ KIR2DL1$^-$ (licensed) and KIR2DL3$^-$ (unlicensed) NK subsets, stimulated with PMA/ION for 12 hours, and analyzed using SCBC. (A) 2-D scatter plot of representative cytokine production levels from licensed (red) and unlicensed (blue) NK cell subsets. Axis units are fluorescence intensity. A gate is determined for each cytokine. The number in each quadrant represents the percentage of cells in that quadrant. (B) Polyfunctionality plot showing the composition of NK subsets secreting 0, 1, 2, 3, 4, 5, and >5 cytokines in licensed (red) and unlicensed (blue) NK cells. The frequency for each category is shown. (C) Hierarchical cluttering of cytokine production profile from single licensed (red) and unlicensed (blue) NK cell subsets. Each column represents one single cell, and each row presents one cytokine. The color scale shows the difference in standard deviation.
Figure 6:
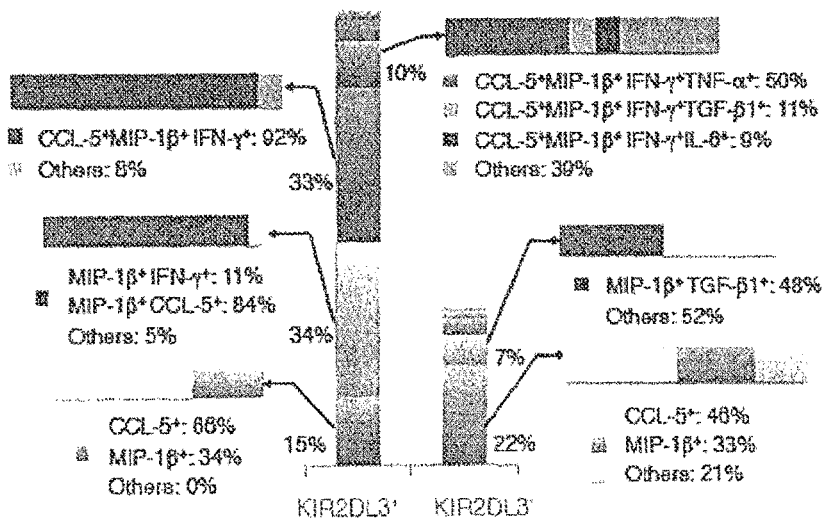
Figure 6:
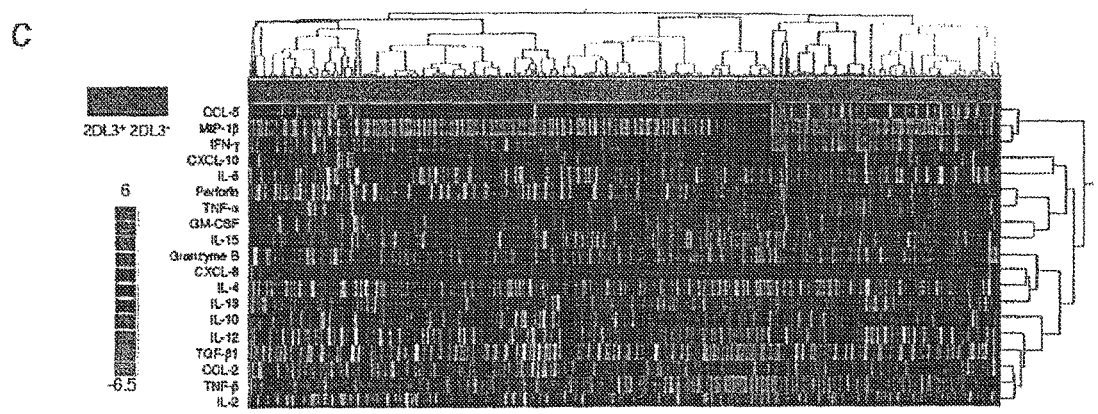

Accordingly, these studies indicate that licensed NK cells were able to produce a wide variety of cytokines, and were more polyfunctional than unlicensed NK cells (FIG. 6B). The reason for the functional heterogeneity observed in each subpopulation is uncertain, but is likely to reflect action of other cytokine and activating receptor interactions that contribute to maturational and educational plasticity of the NK population (B. N. Jaeger, E. Vivier, When NK cells overcome their lack of education. J Clin Invest 122, 3053 (Sep. 4, 2012); C. Sola et al., Genetic and antibody-mediated reprogramming of natural killer cell missing-self recognition in vivo. Proc Natl Acad Sci USA 106, 12879 (Aug. 4, 2009)).

Figure 7:
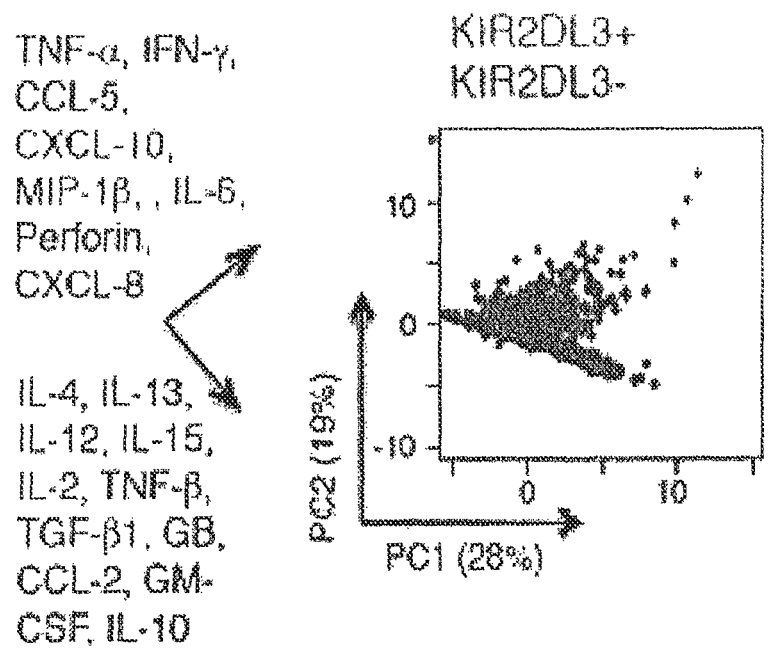
FIG. 7 depicts licensed NK cells from an AA haplotype individual display higher effector protein production capacity. PCA of secretion profiles from licensed (red) and unlicensed (blue) NK subsets. Percentage of variation explained by each component is shown in parentheses. The factors for each component are indicated left of the plot.

Analysis of ~1,500 KIR2DL3$^+$ and KIR2DL3$^-$ single NK cells primarily resolved into two clusters: one cluster primarily contains KIR2DL3$^+$ NK cells polarized towards a pro-inflammatory state (left cluster in FIG. 6C), and the second cluster primarily contains KIR2DL3$^-$NK cells polarized towards a more regulatory state, (right cluster of FIG. 6C, licensed and unlicensed NK cells are also indicated by the top red-blue row). Principal component analysis (PCA) showed that the two subsets have strikingly opposing characteristics, particularly distinguished in their production of effector proteins (such as TNF-α, IFN-y, and chemokines) shown in the second component (19% of variance, FIG. 7). It is important to emphasize that KIR2DL3$^-$NK cells were not cytokine silent, but instead polarized for a distinct program of cytokine production, including IL-12, TGF-β, and TNF-13. Taken together, these novel findings indicated that licensing mediated by KIR2DL3/HLA-C1 interaction conferred pro-inflammatory immune mediator production program in NK cells.

Figure 8:
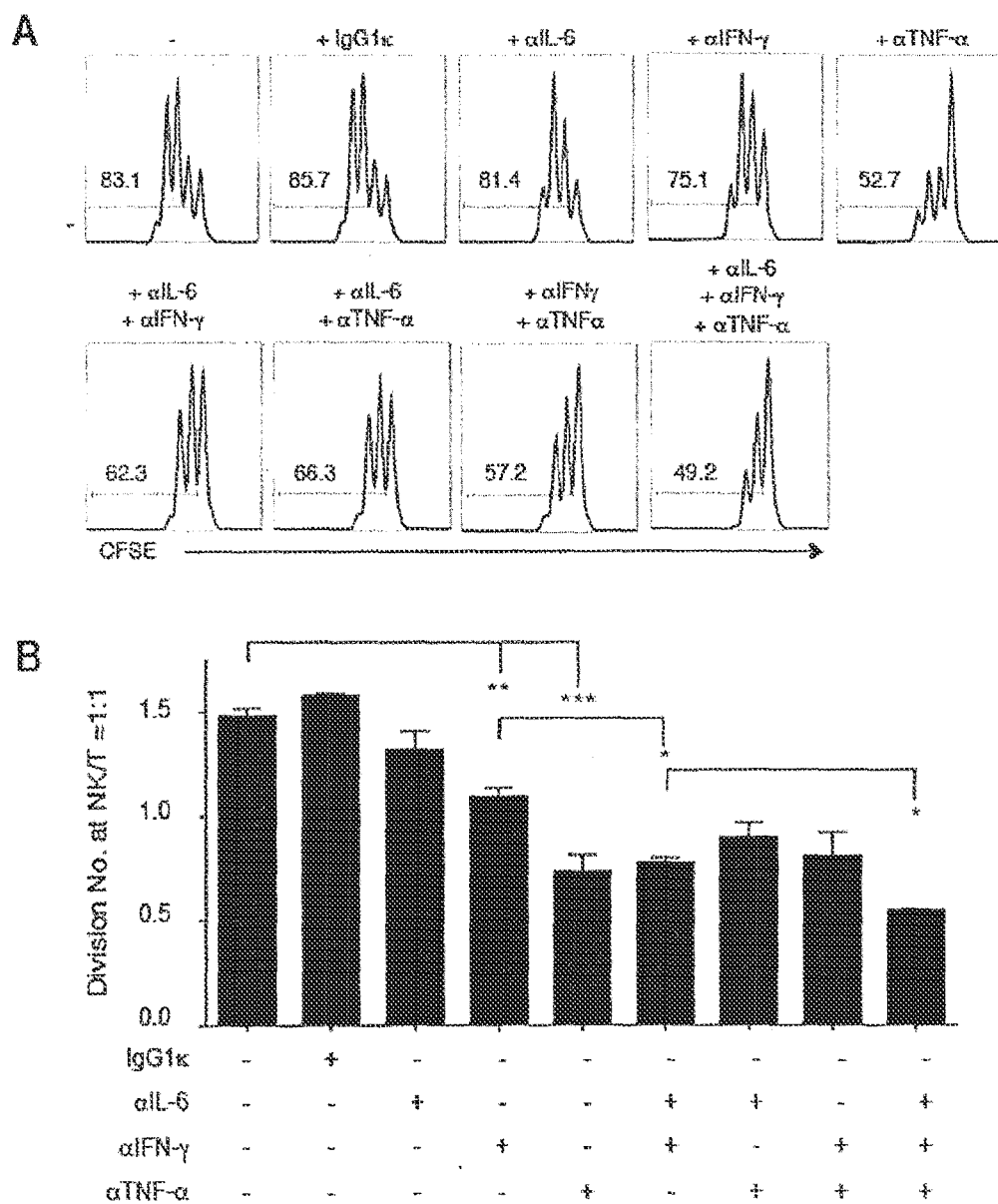
FIG. 8 depicts that neutralizing IFN-g, TNF-α, and IL-6 in NK-T cell co-culture ameliorated CD4$^+$ T cell proliferation. NK and autologous CD4$^+$ T were isolated from an AA haplotype licensed individual, stimulated with 1.5 ug mL$^{-1}$ immobilized anti-CD3 and anti-CD28, and co-cultured in 2 ng mL$^{-1}$ (26 I.U) IL-2 for 3 days. (A) Histograms of CD4$^+$ T cell CFSE dilution without or with the indicated neutralizing antibodies. The number in each histogram indicates the percentage of cells proliferated. (B) Bar plot of CD4$^+$ T cells division number at NK/T=1:1 from the AA haplotype healthy individual. (n=2 to 6, two-tailed student t test, *p<0.05; p<0.005; *p<0.0005). (C) Bar plot showing the depletion of licensed NK cell cytokines abrogates CD4$^+$ T cell proliferation.
Figure 8:
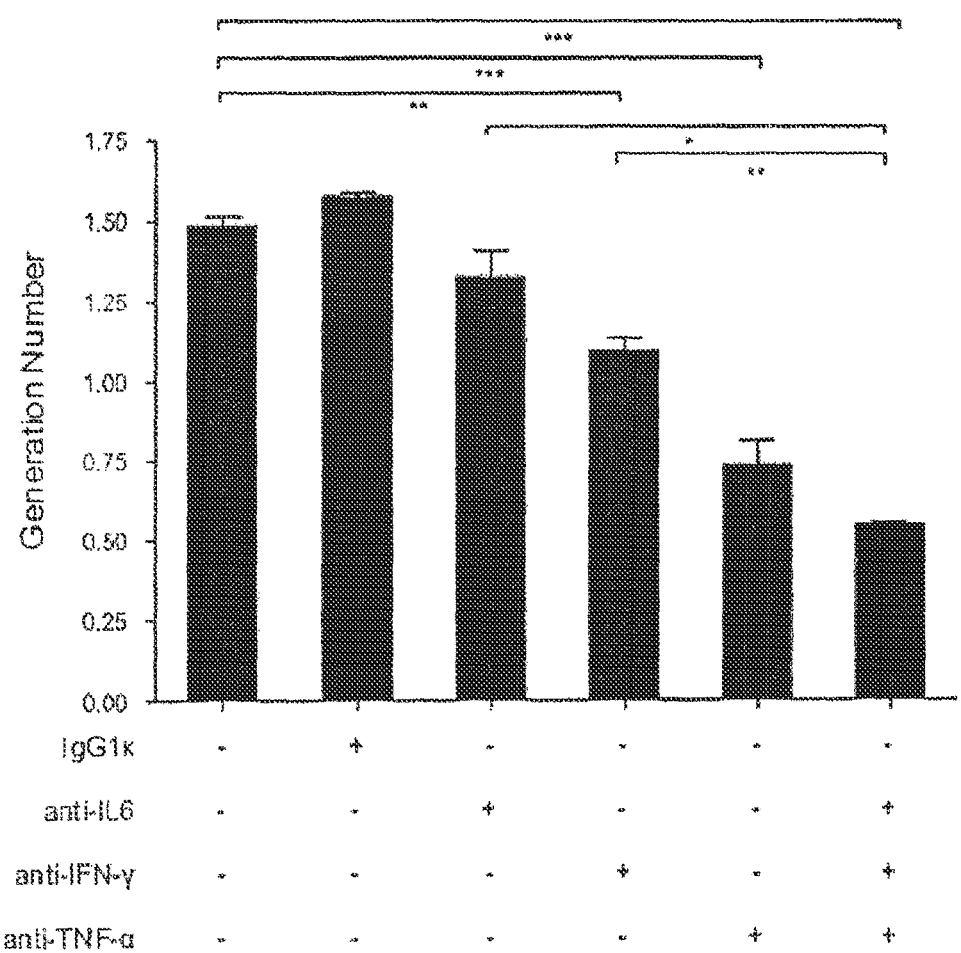

Example 5: IFN-y, TNF-α, and IL-6 Account for the Capacity of Licensed NK Cells to Augment CD4$^+$ T Cell Proliferation To evaluate whether the cytokines produced by licensed NK cells could indeed promote CD4$^+$ T cell proliferation, IL-6, IFN-y, TNF-ct, or their combinations in NK-T co-cultures were neutralized (FIGS. 8A and 8B).

Neutralization of TNF-ct alone had a great impact on CD4$^+$ T cell proliferation, and this effect was specific compared to IgG1κ isotype control.

Neutralization of IL-6 or IFN-y alone had measurable but modest effects, but their combination markedly reduced CD4+ T cell proliferation, suggesting synergistic interaction between them.

Figure 9:
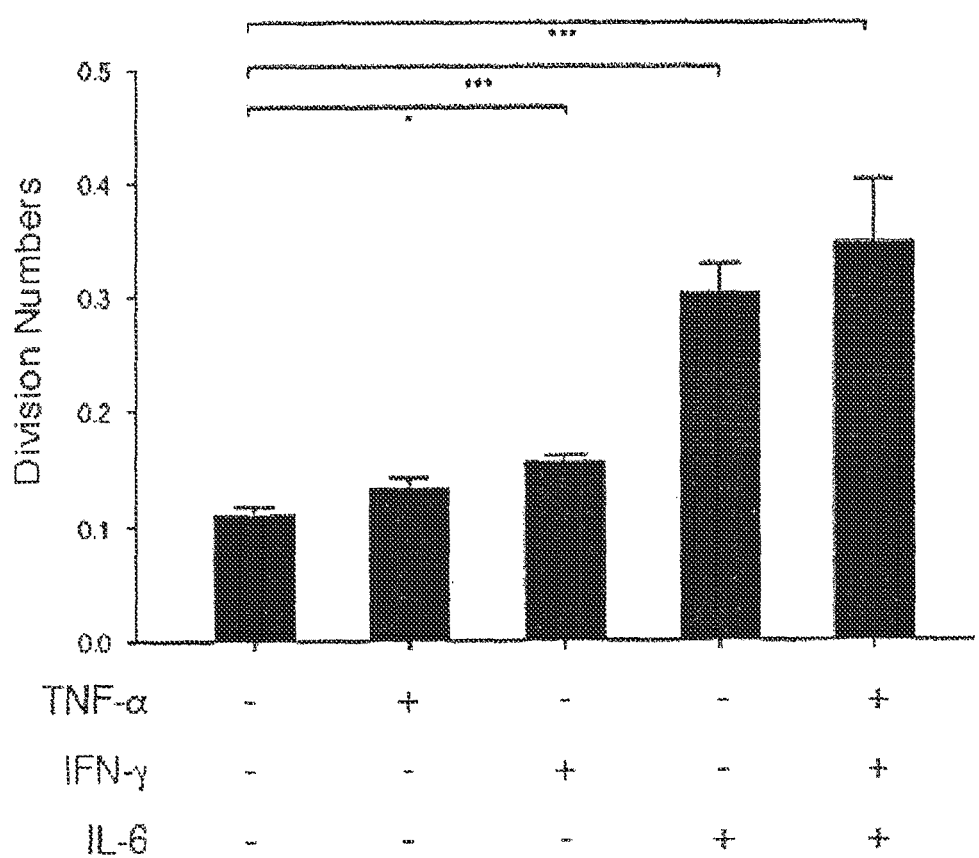
FIG. 9 depicts the addition of selected NK cytokines promoted CD4+ T cell proliferation. Barplot of CD4+ T cell proliferation in three-day co-culture with or without of the indicated cytokines at the concentration of 20 ng ml$^{-1}$. Division numbers were calculated as Log 2 (mean of overall CFSE intensity/mean of undiluted CFSE intensity). n=2 to 7, student t test, two-tailed, (*p<0.05, ***p<0.0001).

T cell proliferation was further evaluated in the absence of NK cells, in which exogenous cytokines were added at 20 ng mL$^{-1}$, comparable to that produced by licensed NK cells (FIG. 9). IFN-y or TNF-ct had marginal effects, but the addition of IL-6 or all three greatly facilitated CD4+ cell proliferation. This indicates that IL-6 might not be necessary to augment CD4+ cell proliferation in the presence of other cytokines produced by licensed NK cells, but it was sufficient to carry the proliferating effect alone. These cytokine depletion and addition results demonstrated that CD4+ cell proliferation mediated by NK cells does not rely solely on one particular cytokine, but rather depends on the balance of multiple key cytokines Example 6: Supernatant of NK Cells from Genetically Licensed Individuals Potently Promoted TH17 Differentiation T helper 17 (TH17) cells are crucial drivers for multiple chronic inflammatory diseases, including CD (M. J. McGeachy, D. J. Cua, Th17 cell differentiation: the long and winding road. *Immunity* 28, 445 (April, 2008); A. Franke et al., Genome-wide meta-analysis increases to 71 the number of confirmed Crohn's disease susceptibility loci. *Nat Genet* 42, 1118 (December, 2010)), but there is little information about if or how NK cells might affect TH17 formation or activity. The foregoing results indicated that licensed NK cells are robust producers of several cytokines, notably IL-6, important in TH17 differentiation (40, 42, 43). We therefore tested the effect of licensed NK cell cytokines on TH17 differentiation. While the conditions for murine TH17 differentiation have been well defined, a general agreement on the factors required for human TH17 cell differentiation remains to be established (M. J. McGeachy, D. J. Cua, Th17 cell differentiation: the long and winding road. *Immunity* 28, 445 (April, 2008); E. V. Acosta-Rodriguez, G. Napolitani, A. Lanzavecchia, F. Sallusto, Interleukins 1beta and 6 but not transforming growth factor-beta are essential for the differentiation of interleukin 17-producing human T helper cells. *Nat Immunol* 8, 942 (September, 2007); N. J. Wilson et al., Development, cytokine profile and function of human interleukin 17-producing helper T cells. *Nat Immunol* 8, 950 (September, 2007)).

Figure 10:
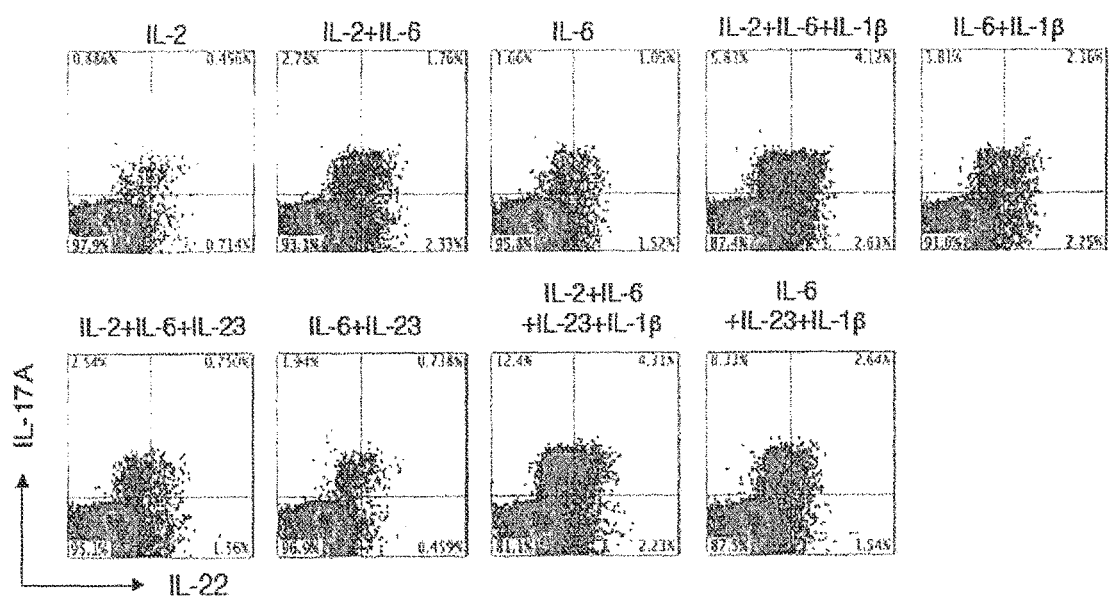
FIG. 10 depicts the in vitro Th17 differentiation in various cytokine combinations. Scatter plot of IL-17A and IFN-γ intracellular production from CD4+ T cells at D14 after differentiation with or without IL-2 at 2 ng mL$^{-1}$, in the presence or absence of IL-1β, IL-23, or IL-6, at 50 ng mL$^{-1}$, as indicated.

In a first series of studies, it was established that IL-17A and IL-22 producing TH17 cells can be successfully induced from total peripheral CD4+ T cells using a variety of cytokine combinations. The most effective were IL-23/IL-6/IL-1l3/IL-2, IL-23/IL-6/IL-1l3, and IL-6/IL-1l3/IL-2 (FIG. 10).

Figure 12:
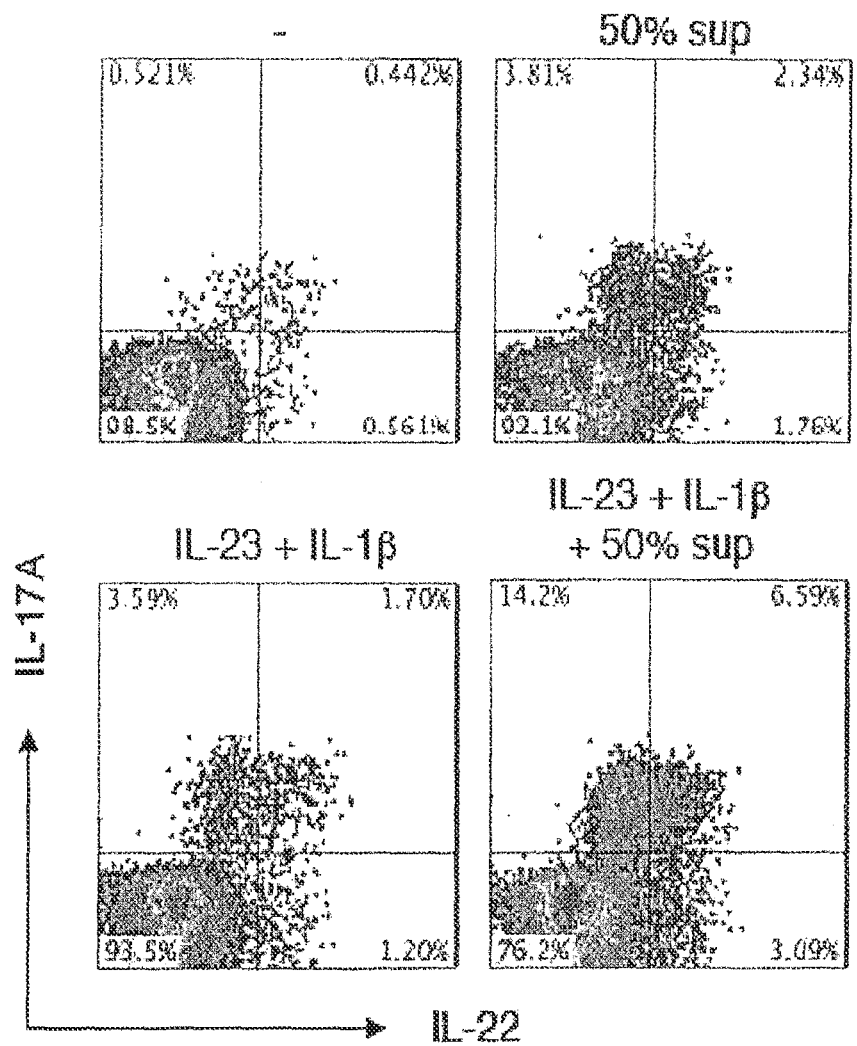
FIG. 12 shows that licensed NK cell supernatant facilitated in vitro Th17 differentiation alone or synergistically with IL-1β and IL-23. Scatter plot of IL-17A and IFN-γ intracellular production from CD4+ T cells at D14 after differentiation with IL-13 or IL-23 and IL-1b, at concentration of 50 ng mL$^{-1}$, with or without the addition of NK cell supernatant. Numbers in each quadrant represents the percentage of cell in that section.

To determine if licensed NK supernatant could promote TH17 differentiation in total CD4+ cells, NK supernatants from a licensed CD patient (AA KIR and C1C1 HLA) were titrated into CD4+ cell cultures for 6-7 days, the cultures were further propagated for another 6-7 days, and then the cultures were assessed for IL-17A and IL-22 producing cells by flow cytometry. Compared to CD4+ cells polarized with IL-1l3 or IL-23 alone, addition of 50% licensed NK cell supernatant dramatically increased the percentage of IL-17A+, IL-22+, and IL-17A+IL-22+ cells (FIGS. 11A and 11B). The same effects were also observed with licensed NK supernatants alone, or in combination with both IL-1l3 and IL-23 (FIG. 12).

Using the IL-23 plus NK supernatant condition, NK cell supernatants from four different healthy subjects with a licensing genotype (AA KIR, C1C1 HLA) were analyzed. All of them showed TH17 differentiation capacity, assessed from their higher percentages of IL-17A+, IL-22+, and IL-17A+IL-22+ cells (FIG. 11C).

These findings consistently demonstrated that licensed NK cells secret immune mediators that can strongly promote TH17 differentiation, either alone or synergistically with IL-23 and IL-1l3. They also demonstrate that comparable TH17-inducing cytokines are produced by licensed NK cells from healthy individuals.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A method for treating a patient having a chronic inflammatory disease, the method comprising administering a 6-thiopurine or 6-thioguanine treatment regimen to the patient having the chronic inflammatory disease,
    wherein the patient is determined have a KIR/HLA-haplotype of an AA haplotype, homozygous for HLA-C1 and present for Bw6; a non-AA haplotype, present for KIR2DL2 and homozygous for HLA-C1; a non-AA haplotype, present for KIR2DL2 and heterozygous for HLA-C1/HLA-C2; or a non-AA haplotype, absent for KIR2DL2 and homozygous for HLA-C1, based on a KIR/HLA haplotype determination of the patient, and
    wherein the KIR/HLA-haplotype of the patient is determined by:
    (a) providing a biological sample from the patient;
    (b) obtaining nucleic acid from the biological sample; and
    (c) hybridizing the nucleic acid, to:
        (i) a first solid support comprising synthetic capture probes selective for KIR2DL3, KIR2DL1, KIR2DL4, KIR3DL1, KIR3DL2, KIR3DL3, KIR2DS4, KIR2DP1, KIR3DP1, KIR2DL5, KIR2DS1, KIR2DS2, KIR2DS3, KIR2DS5, and KIR3DS1; and
        (ii) a second solid support comprising capture probes selective for HLA-C1, HLA-C2, HLA-Bw4 and HLA-Bw6.

2. The method of claim 1, wherein the biological sample is a blood sample.

3. The method of claim 1, wherein the patient is a human.

4. The method of claim 1, wherein the treatment regimen is a 6-thioguanine treatment regimen.

* * * * *